(12) United States Patent
Gliner et al.

(10) Patent No.: US 8,606,361 B2
(45) Date of Patent: Dec. 10, 2013

(54) SYSTEMS AND METHODS FOR ENHANCING OR AFFECTING NEURAL STIMULATION EFFICIENCY AND/OR EFFICACY

(75) Inventors: Bradford Evan Gliner, Sammamish, WA (US); Allen Wyler, Seattle, WA (US); Brad Fowler, Woodinville, WA (US); W. Douglas Sheffield, Seatac, WA (US); Richard Kuntz, Lakebay, WA (US); Kent Leyde, Redmond, WA (US); Leif R. Sloan, Seattle, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 338 days.

(21) Appl. No.: 13/179,133

(22) Filed: Jul. 8, 2011

(65) Prior Publication Data

US 2012/0041498 A1     Feb. 16, 2012

Related U.S. Application Data

(60) Continuation of application No. 12/327,711, filed on Dec. 3, 2008, now Pat. No. 7,983,762, and a division of application No. 11/182,713, filed on Jul. 15, 2005, now Pat. No. 7,483,747.

(60) Provisional application No. 60/588,406, filed on Jul. 15, 2004.

(51) Int. Cl.
*A61N 1/36*     (2006.01)

(52) U.S. Cl.
USPC ................................. 607/45; 607/3

(58) Field of Classification Search
USPC ................ 607/1–3, 45, 46, 48, 115, 116, 120
See application file for complete search history.

(56) References Cited

U.S. PATENT DOCUMENTS

| | | |
|---|---|---|
| 2,716,226 A | 8/1955 | Jonas |
| 2,721,316 A | 10/1955 | Shaw |
| 3,628,193 A | 12/1971 | Collins |

(Continued)

FOREIGN PATENT DOCUMENTS

| | | |
|---|---|---|
| DE | 19750043 | 5/1999 |
| EP | 0214527 | 3/1987 |

(Continued)

OTHER PUBLICATIONS

U.S. Appl. No. 10/583,630, filed Jun. 20, 2006—Lozano.

(Continued)

*Primary Examiner* — Brian T Gedeon

(57) ABSTRACT

Systems and methods for enhancing or affecting neural stimulation efficiency and/or efficacy are disclosed. In one embodiment, a system and/or method may apply electromagnetic stimulation to a patient's nervous system over a first time domain according to a first set of stimulation parameters, and over a second time domain according to a second set of stimulation parameters. The first and second time domains may be sequential, simultaneous, or nested. Stimulation parameters may vary in accordance with one or more types of duty cycle, amplitude, pulse repetition frequency, pulse width, spatiotemporal, and/or polarity variations. Stimulation may be applied at subthreshold, threshold, and/or suprathreshold levels in one or more periodic, aperiodic (e.g., chaotic), and/or pseudo-random manners. In some embodiments stimulation may comprise a burst pattern having an interburst frequency corresponding to an intrinsic brainwave frequency, and regular and/or varying intraburst stimulation parameters. Stimulation signals providing reduced power consumption with at least adequate symptomatic relief may be applied prior to moderate or significant power source depletion.

5 Claims, 29 Drawing Sheets

(56) References Cited

U.S. PATENT DOCUMENTS

| | | |
|---|---|---|
| 3,650,276 A | 3/1972 | Burghele et al. |
| 3,850,161 A | 11/1974 | Liss |
| 3,918,461 A | 11/1975 | Cooper |
| 4,019,518 A | 4/1977 | Maurer et al. |
| 4,030,509 A | 6/1977 | Heilman et al. |
| 4,125,116 A | 11/1978 | Fischell |
| 4,140,133 A | 2/1979 | Kastrubin et al. |
| 4,214,804 A | 7/1980 | Little |
| 4,245,645 A | 1/1981 | Arseneault et al. |
| 4,308,868 A | 1/1982 | Jhabvala |
| 4,328,813 A | 5/1982 | Ray |
| 4,340,038 A | 7/1982 | McKean |
| 4,390,023 A | 6/1983 | Rise |
| 4,431,000 A | 2/1984 | Butler et al. |
| 4,474,186 A | 10/1984 | Ledley et al. |
| 4,541,432 A | 9/1985 | Molina-Negro et al. |
| 4,542,752 A | 9/1985 | DeHaan et al. |
| 4,590,946 A | 5/1986 | Loeb |
| 4,607,639 A | 8/1986 | Tanagho et al. |
| 4,646,744 A | 3/1987 | Capel |
| 4,702,254 A | 10/1987 | Zabara |
| 4,817,634 A | 4/1989 | Holleman et al. |
| 4,844,075 A | 7/1989 | Liss et al. |
| 4,865,048 A | 9/1989 | Eckerson |
| 4,869,255 A | 9/1989 | Putz |
| 4,903,702 A | 2/1990 | Putz |
| 4,969,468 A | 11/1990 | Byers et al. |
| 5,002,053 A | 3/1991 | Garcia-Rill et al. |
| 5,024,226 A | 6/1991 | Tan |
| 5,031,618 A | 7/1991 | Mullett |
| 5,044,368 A | 9/1991 | Putz |
| 5,054,906 A | 10/1991 | Lyons |
| 5,063,932 A | 11/1991 | Dahl et al. |
| 5,092,835 A | 3/1992 | Schurig et al. |
| 5,121,754 A | 6/1992 | Mullett |
| 5,143,089 A | 9/1992 | Alt |
| 5,169,384 A | 12/1992 | Bosniak et al. |
| 5,184,620 A | 2/1993 | Cudahy et al. |
| 5,193,540 A | 3/1993 | Schulman et al. |
| 5,215,086 A | 6/1993 | Terry, Jr. et al. |
| 5,215,088 A | 6/1993 | Normann et al. |
| 5,224,491 A | 7/1993 | Mehra |
| 5,255,678 A | 10/1993 | Deslauriers et al. |
| 5,263,967 A | 11/1993 | Lyons, III et al. |
| 5,269,303 A | 12/1993 | Wernicke et al. |
| 5,271,417 A | 12/1993 | Swanson et al. |
| 5,282,468 A | 2/1994 | Klepinski |
| 5,299,569 A | 4/1994 | Wernicke et al. |
| 5,303,705 A | 4/1994 | Nenov |
| 5,304,206 A | 4/1994 | Baker, Jr. et al. |
| 5,314,458 A | 5/1994 | Najafi et al. |
| 5,358,513 A | 10/1994 | Powell, III et al. |
| 5,358,514 A | 10/1994 | Schulman et al. |
| 5,370,672 A | 12/1994 | Fowler et al. |
| 5,405,375 A | 4/1995 | Ayers et al. |
| 5,406,957 A | 4/1995 | Tansey |
| 5,411,540 A | 5/1995 | Edell et al. |
| 5,417,719 A | 5/1995 | Hull et al. |
| 5,423,864 A | 6/1995 | Ljungstroem |
| 5,441,528 A | 8/1995 | Chang et al. |
| 5,464,446 A | 11/1995 | Dreessen et al. |
| 5,520,190 A | 5/1996 | Benedict et al. |
| 5,522,864 A | 6/1996 | Wallace et al. |
| 5,537,512 A | 7/1996 | Hsia et al. |
| 5,540,734 A | 7/1996 | Zabara |
| 5,540,736 A | 7/1996 | Haimovish et al. |
| 5,549,655 A | 8/1996 | Erickson |
| 5,562,708 A | 10/1996 | Combs et al. |
| 5,575,813 A | 11/1996 | Edell et al. |
| 5,591,216 A | 1/1997 | Testerman et al. |
| 5,593,432 A | 1/1997 | Crowther et al. |
| 5,601,611 A | 2/1997 | Fayram et al. |
| 5,611,350 A | 3/1997 | John |
| 5,618,531 A | 4/1997 | Cherksey |
| 5,628,317 A | 5/1997 | Starkebaum et al. |
| 5,674,251 A | 10/1997 | Combs et al. |
| 5,674,264 A | 10/1997 | Carter et al. |
| 5,676,655 A | 10/1997 | Howard, III et al. |
| 5,683,422 A | 11/1997 | Rise |
| 5,702,429 A | 12/1997 | King |
| 5,707,334 A | 1/1998 | Young |
| 5,711,316 A | 1/1998 | Elsberry et al. |
| 5,713,922 A | 2/1998 | King |
| 5,713,923 A | 2/1998 | Ward et al. |
| 5,716,377 A | 2/1998 | Rise et al. |
| 5,722,401 A | 3/1998 | Pietroski et al. |
| 5,735,814 A | 4/1998 | Elsberry et al. |
| 5,750,376 A | 5/1998 | Weiss et al. |
| 5,752,979 A | 5/1998 | Benabid |
| 5,753,505 A | 5/1998 | Luskin |
| 5,769,778 A | 6/1998 | Abrams et al. |
| 5,772,591 A | 6/1998 | Cram |
| 5,782,798 A | 7/1998 | Rise |
| 5,782,873 A | 7/1998 | Collins |
| 5,792,186 A | 8/1998 | Rise |
| 5,797,970 A | 8/1998 | Pouvreau |
| 5,814,014 A | 9/1998 | Elsberry et al. |
| 5,814,092 A | 9/1998 | King |
| 5,824,021 A | 10/1998 | Rise |
| 5,824,030 A | 10/1998 | Yang et al. |
| 5,832,932 A | 11/1998 | Elsberry et al. |
| 5,833,603 A | 11/1998 | Kovacs et al. |
| 5,833,709 A | 11/1998 | Rise et al. |
| 5,843,148 A | 12/1998 | Gijsbers et al. |
| 5,843,150 A | 12/1998 | Dreessen et al. |
| 5,846,196 A | 12/1998 | Siekmeyer et al. |
| 5,865,842 A | 2/1999 | Knuth et al. |
| 5,871,517 A | 2/1999 | Abrams et al. |
| 5,885,976 A | 3/1999 | Sandyk |
| 5,886,769 A | 3/1999 | Zolten |
| 5,893,883 A | 4/1999 | Torgerson et al. |
| 5,904,916 A | 5/1999 | Hirsch |
| 5,913,882 A | 6/1999 | King |
| 5,916,171 A | 6/1999 | Mayevsky |
| 5,925,070 A | 7/1999 | King et al. |
| 5,928,144 A | 7/1999 | Real |
| 5,938,688 A | 8/1999 | Schiff |
| 5,938,689 A | 8/1999 | Fischell et al. |
| 5,941,902 A | 8/1999 | Holcomb |
| 5,941,906 A | 8/1999 | Barreras, Sr. et al. |
| 5,975,085 A | 11/1999 | Rise |
| 5,978,702 A | 11/1999 | Ward et al. |
| 5,983,140 A | 11/1999 | Smith et al. |
| 6,006,124 A | 12/1999 | Fischell et al. |
| 6,011,996 A | 1/2000 | Gielen et al. |
| 6,016,449 A | 1/2000 | Fischell et al. |
| 6,018,682 A | 1/2000 | Rise |
| 6,021,352 A | 2/2000 | Christopherson et al. |
| 6,024,702 A | 2/2000 | Iversen |
| 6,026,326 A | 2/2000 | Bardy |
| 6,035,236 A | 3/2000 | Jarding et al. |
| 6,038,480 A | 3/2000 | Hrdlicka et al. |
| 6,040,180 A | 3/2000 | Johe |
| 6,042,579 A | 3/2000 | Elsberry et al. |
| 6,052,624 A | 4/2000 | Mann |
| 6,055,456 A | 4/2000 | Gerber |
| 6,057,846 A | 5/2000 | Sever, Jr. |
| 6,057,847 A | 5/2000 | Jenkins |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,094,598 A | 7/2000 | Elsberry et al. |
| 6,095,148 A | 8/2000 | Shastri et al. |
| 6,104,956 A | 8/2000 | Naritoku et al. |
| 6,104,960 A | 8/2000 | Duysens et al. |
| 6,111,911 A | 8/2000 | Sanderford, Jr. et al. |
| 6,122,548 A | 9/2000 | Starkebaum et al. |
| 6,126,657 A | 10/2000 | Edwards et al. |
| 6,128,527 A | 10/2000 | Howard, III et al. |
| 6,128,537 A | 10/2000 | Rise |
| 6,128,538 A | 10/2000 | Fischell et al. |
| 6,134,474 A | 10/2000 | Fischell et al. |
| 6,149,612 A | 11/2000 | Schnapp et al. |

(56) References Cited

U.S. PATENT DOCUMENTS

| | | |
|---|---|---|
| 6,152,143 A | 11/2000 | Edwards |
| 6,161,044 A | 12/2000 | Silverstone |
| 6,161,045 A | 12/2000 | Fischell et al. |
| 6,161,047 A | 12/2000 | King et al. |
| 6,176,242 B1 | 1/2001 | Rise |
| 6,190,893 B1 | 2/2001 | Shastri et al. |
| 6,198,958 B1 | 3/2001 | Ives et al. |
| 6,205,360 B1 | 3/2001 | Carter et al. |
| 6,205,361 B1 | 3/2001 | Kuzma et al. |
| 6,210,417 B1 | 4/2001 | Baudino et al. |
| 6,221,908 B1 | 4/2001 | Kilgard et al. |
| 6,227,203 B1 | 5/2001 | Rise et al. |
| 6,230,049 B1 | 5/2001 | Fischell et al. |
| 6,236,892 B1 | 5/2001 | Feler |
| 6,246,912 B1 | 6/2001 | Sluijter et al. |
| 6,263,225 B1 | 7/2001 | Howard, III |
| 6,280,462 B1 | 8/2001 | Hauser et al. |
| 6,301,493 B1 | 10/2001 | Marro et al. |
| 6,304,787 B1 | 10/2001 | Kuzma et al. |
| 6,319,241 B1 | 11/2001 | King et al. |
| 6,339,725 B1 | 1/2002 | Naritoku et al. |
| 6,353,754 B1 | 3/2002 | Fischell et al. |
| 6,353,762 B1 | 3/2002 | Baudino et al. |
| 6,354,299 B1 | 3/2002 | Fischell et al. |
| 6,356,786 B1 | 3/2002 | Rezai et al. |
| 6,356,792 B1 | 3/2002 | Errico et al. |
| 6,360,122 B1 | 3/2002 | Fischell et al. |
| 6,366,813 B1 | 4/2002 | DiLorenzo |
| 6,375,666 B1 | 4/2002 | Mische |
| 6,381,496 B1 | 4/2002 | Meadows et al. |
| 6,393,319 B1 | 5/2002 | Bock et al. |
| 6,405,079 B1 | 6/2002 | Ansarinia |
| 6,418,344 B1 | 7/2002 | Rezai |
| 6,427,086 B1 | 7/2002 | Fischell et al. |
| 6,456,886 B1 | 9/2002 | Howard, III et al. |
| 6,459,936 B2 | 10/2002 | Fischell et al. |
| 6,463,328 B1 | 10/2002 | John |
| 6,464,356 B1 | 10/2002 | Sabel et al. |
| 6,466,822 B1 | 10/2002 | Pless |
| 6,473,639 B1 | 10/2002 | Fischell et al. |
| 6,480,743 B1 | 11/2002 | Kirkpatrick et al. |
| 6,484,059 B2 | 11/2002 | Gielen |
| 6,487,450 B1 | 11/2002 | Chen |
| 6,497,699 B1 | 12/2002 | Ludvig et al. |
| 6,499,488 B1 | 12/2002 | Hunter et al. |
| 6,505,075 B1 | 1/2003 | Weiner |
| 6,507,755 B1 | 1/2003 | Gozani et al. |
| 6,529,774 B1 | 3/2003 | Greene |
| 6,539,263 B1 | 3/2003 | Schiff et al. |
| 6,549,814 B1 | 4/2003 | Strutz et al. |
| 6,556,868 B2 | 4/2003 | Naritoku et al. |
| 6,569,654 B2 | 5/2003 | Shastri et al. |
| 6,591,138 B1 | 7/2003 | Fischell et al. |
| 6,597,954 B1 | 7/2003 | Pless et al. |
| 6,609,031 B1 | 8/2003 | Law et al. |
| 6,615,065 B1 | 9/2003 | Barrett et al. |
| 6,622,048 B1 | 9/2003 | Mann et al. |
| 6,631,295 B2 | 10/2003 | Rubinstein et al. |
| 6,633,780 B1 | 10/2003 | Berger |
| 6,647,296 B2 | 11/2003 | Fischell et al. |
| 6,658,299 B1 | 12/2003 | Dobelle |
| 6,665,562 B2 | 12/2003 | Gluckman et al. |
| 6,684,105 B2 | 1/2004 | Cohen et al. |
| 6,687,525 B2 | 2/2004 | Llinas et al. |
| 6,690,974 B2 | 2/2004 | Archer et al. |
| 6,708,064 B2 | 3/2004 | Rezai |
| 6,725,094 B2 | 4/2004 | Saberski |
| 6,764,498 B2 | 7/2004 | Mische |
| 6,782,292 B2 | 8/2004 | Whitehurst |
| 6,788,975 B1 | 9/2004 | Whitehurst et al. |
| 6,795,737 B2 | 9/2004 | Gielen et al. |
| 6,810,286 B2 | 10/2004 | Donovan et al. |
| 6,819,956 B2 | 11/2004 | DiLorenzo |
| 6,839,594 B2 | 1/2005 | Cohen et al. |
| 6,850,802 B2 | 2/2005 | Holsheimer |
| 6,873,872 B2 | 3/2005 | Gluckman et al. |
| 6,892,097 B2 | 5/2005 | Holsheimer |
| 6,895,280 B2 | 5/2005 | Meadows et al. |
| 6,898,464 B2 | 5/2005 | Edell et al. |
| 6,907,296 B1 | 6/2005 | Doan et al. |
| 6,934,580 B1 | 8/2005 | Osorio et al. |
| 6,944,497 B2 | 9/2005 | Stypulkowski |
| 6,944,501 B1 | 9/2005 | Pless |
| 6,949,081 B1 | 9/2005 | Chance |
| 6,959,215 B2 | 10/2005 | Gliner et al. |
| 6,990,377 B2 | 1/2006 | Gliner et al. |
| 7,006,859 B1 | 2/2006 | Osorio et al. |
| 7,015,816 B2 | 3/2006 | Wildman et al. |
| 7,024,247 B2 | 4/2006 | Gliner et al. |
| 7,050,856 B2 | 5/2006 | Stypulkowski |
| 7,065,412 B2 | 6/2006 | Swoyer et al. |
| 7,107,097 B2 | 9/2006 | Stern et al. |
| 7,110,820 B2 | 9/2006 | Tcheng et al. |
| 7,146,217 B2 | 12/2006 | Firlik |
| 7,184,840 B2 | 2/2007 | Stolz et al. |
| 7,187,968 B2 | 3/2007 | Wolf et al. |
| 2002/0077670 A1 | 6/2002 | Archer et al. |
| 2002/0087201 A1 | 7/2002 | Firlik et al. |
| 2002/0091419 A1 | 7/2002 | Firlik |
| 2002/0099295 A1 | 7/2002 | Gil et al. |
| 2002/0099412 A1 | 7/2002 | Fischell et al. |
| 2002/0138101 A1 | 9/2002 | Suda et al. |
| 2002/0169485 A1 | 11/2002 | Pless et al. |
| 2003/0067963 A1 | 4/2003 | Miller et al. |
| 2003/0074032 A1 | 4/2003 | Gliner |
| 2003/0078633 A1 | 4/2003 | Firlik et al. |
| 2003/0088274 A1 | 5/2003 | Gliner et al. |
| 2003/0097161 A1 | 5/2003 | Firlik et al. |
| 2003/0125772 A1 | 7/2003 | Olsen et al. |
| 2003/0125786 A1 | 7/2003 | Gliner et al. |
| 2003/0130706 A1 | 7/2003 | Sheffield et al. |
| 2003/0149457 A1 | 8/2003 | Tcheng et al. |
| 2003/0176901 A1 | 9/2003 | May |
| 2003/0187490 A1 | 10/2003 | Gliner |
| 2003/0187491 A1 | 10/2003 | Greenberg et al. |
| 2003/0195602 A1 | 10/2003 | Boling |
| 2003/0233137 A1 | 12/2003 | Paul |
| 2004/0073270 A1 | 4/2004 | Firlik et al. |
| 2004/0082847 A1 | 4/2004 | McDermott |
| 2004/0088021 A1 | 5/2004 | Cameron et al. |
| 2004/0088024 A1 | 5/2004 | Firlik et al. |
| 2004/0092809 A1 | 5/2004 | DeCharms |
| 2004/0095990 A1 | 5/2004 | Gossett et al. |
| 2004/0102828 A1 | 5/2004 | Lowry et al. |
| 2004/0111127 A1 | 6/2004 | Gliner |
| 2004/0138550 A1 | 7/2004 | Hartlep et al. |
| 2004/0158298 A1 | 8/2004 | Gliner et al. |
| 2004/0176831 A1 | 9/2004 | Gliner et al. |
| 2004/0181263 A1 | 9/2004 | Balzer et al. |
| 2004/0236388 A1 | 11/2004 | Gielen et al. |
| 2004/0243205 A1 | 12/2004 | Keravel et al. |
| 2004/0249422 A1 | 12/2004 | Gliner et al. |
| 2005/0004620 A1 | 1/2005 | Singhal et al. |
| 2005/0013310 A1 | 1/2005 | Banker et al. |
| 2005/0015129 A1 | 1/2005 | Mische |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0033378 A1 | 2/2005 | Sheffield et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0094718 A1 | 5/2005 | Pasternak et al. |
| 2005/0096701 A1 | 5/2005 | Donovan et al. |
| 2005/0113882 A1 | 5/2005 | Cameron et al. |
| 2005/0119712 A1 | 6/2005 | Shafer |
| 2005/0154425 A1 | 7/2005 | Boveja et al. |
| 2005/0154426 A1 | 7/2005 | Boveja et al. |
| 2005/0182453 A1 | 8/2005 | Whitehurst |
| 2005/0228451 A1 | 10/2005 | Jaax et al. |
| 2006/0004422 A1 | 1/2006 | De Ridder |
| 2006/0004423 A1 | 1/2006 | Boveja et al. |

(56) References Cited

U.S. PATENT DOCUMENTS

| | | |
|---|---|---|
| 2006/0015153 A1 | 1/2006 | Gliner et al. |
| 2006/0020297 A1 | 1/2006 | Gerber |
| 2006/0095088 A1 | 5/2006 | De Ridder |
| 2006/0106430 A1 | 5/2006 | Fowler et al. |
| 2006/0106431 A1 | 5/2006 | Wyler et al. |
| 2006/0129205 A1 | 6/2006 | Boveja et al. |
| 2006/0166681 A1 | 7/2006 | Lohbihler |
| 2006/0173522 A1 | 8/2006 | Osorio |
| 2006/0217782 A1 | 9/2006 | Boveja et al. |
| 2006/0241717 A1 | 10/2006 | Whitehurst et al. |
| 2007/0088403 A1 | 4/2007 | Wyler |
| 2007/0100398 A1 | 5/2007 | Sloan |
| 2007/0288072 A1 | 12/2007 | Pascual-Leone |

FOREIGN PATENT DOCUMENTS

| | | |
|---|---|---|
| EP | 0319844 | 6/1989 |
| EP | 0998958 | 5/2000 |
| EP | 1145736 | 10/2001 |
| EP | 1180056 | 11/2003 |
| WO | WO 87-007511 | 12/1987 |
| WO | WO 94-007564 | 4/1994 |
| WO | WO 95-021591 | 8/1995 |
| WO | WO 97-045160 | 12/1997 |
| WO | WO 98-006342 | 2/1998 |
| WO | WO 00-007494 | 2/2000 |
| WO | WO 01-097906 | 12/2001 |
| WO | WO 02-009811 | 2/2002 |
| WO | WO 02-036003 | 5/2002 |
| WO | WO 02-038031 | 5/2002 |
| WO | WO 02-038217 | 5/2002 |
| WO | WO 03-043690 | 5/2003 |
| WO | WO 03-082402 | 10/2003 |
| WO | WO 03-101532 | 12/2003 |

OTHER PUBLICATIONS

U.S. Appl. No. 11/254,060, filed Oct. 19, 2005—Wyler.
U.S. Appl. No. 11/255,187, filed Oct. 19, 2005—Firlik.
U.S. Appl. No. 11/344,453, filed Jan. 30, 2006—Gliner.
U.S. Appl. No. 11/518,139, filed Sep. 7, 2006—Weinand.
U.S. Appl. No. 11/638,326, filed Dec. 12, 2006—Gliner et al.
U.S. Appl. No. 11/697,694, filed Apr. 6, 2007—Fowler.
U.S. Appl. No. 11/697,696, filed Apr. 6, 2007—Pascual-Leone.
U.S. Appl. No. 11/697,703, filed Apr. 6, 2007—Gaw.
Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).
Behrens, T. et al., "Non-invasive mapping of connections between human thalamus and cortex using diffusion imaging," Nature neuroscience, vol. 6 No. 7, pp. 750-757 (Jul. 2003).
Bel, S. and Bauer, B.L., "Dorsal Column Stimulation (DCS): Cost to Benefit Analysis," Acta Neurochirurgica, Suppl. 52, pp. 121-123 (1991).
Benabid, A.L. et al., "Chronic electrical stimulation of the ventralis intermedius nucleus of the thalamus as a treatment of movement disorders," J. Neurosurg., Apr. 1997, 86(4); 737; http:--www.ncbi. nlm.nih.gov; [accessed Nov. 18, 2003].
Beveridge, J. A., "Use of Exogenous Electric Current in the Treatment of Delayed Lesions in Peripheral Nerves," Plastic and Reconstructive Surgery, Oct. 1988, vol. 82, No. 4, pp. 573-579.
Bezard et al., "Cortical Stimulation and Epileptic Seizure: A Study of the Potential Risk in Primates," Neurosurgery, vol. 45, No. 2, Aug. 1999, 346-350.
Binder, J. M.D., "Functional Magnetic Resonance Imaging: Language Mapping," Neurosurgery Clinics of North America, vol. 8, No. 3, Jul. 1997, pp. 383-392.
Bluestone, Avraham Y. et al., "Three-dimensional optical tomography of hemodynamics in the human head," Optics Express, vol. 9, No. 6, pp. 272-286 (Sep. 10, 2001).
Brain Electrical Stimulation to Enhance Recovery After Stroke, ClinicalTrials.gov, URL: http://www.clinicaltrials.gov/ct/show/NCT00085657?order=2 [Retrieved on Dec. 22, 2005].
Burnett, Mark G. et al., "Diffuse optical measurement of blood flow, blood oxygenation, and metabolism in a human brain during sensorimotor cortex activation," Optics Letters, vol. 29, No. 15, pp: 1766-1768 (Aug. 1, 2004).
Bury, Scott et al., "The Effects of Behavioral Demand on Motor Cortical and Cerebellar Structural Plasticity After Brain Injury in Adult Rats," http://www.mcmasterca-inabis98-schallert-bury0827-two.html#introduction, 2 pages [Retrieved on Mar. 1, 2003].
Butefisch et al., "Mechanisms of use-dependent plasticity in the human motor cortex," Proc. Natl. Acad. Sci. USA, vol. 97, No. 7, pp. 3661-3665 (Mar. 2000).
Canavero, S. and Paolotti, R., "Extradural Motor Cortex Stimulation for Advanced Parkinson's Disease: Case Report," Movement Disorders, Jan. 2000, 15(1):169-171.
Cao, Yue et al., "Cortical Language Activation in Stroke Patients Recovering From Aphasia With Functional MRI," Stroke, vol. 30, pp: 2331-2340, Nov. 1999.
Cheun et al., "Differentiation of a Stem Cell Line Toward a Neuronal Phenotype," Int. J. Devl. Neuroscience, vol. 9, No. 4, pp. 391-404 (1991).
Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.
Cincotta et al., "Reorganization of the motor cortex in a patient with congenital hemiparesis and mirror movements," Neurology, Jul. 12, 2000, 5+A535(1), pp. 129-131.
Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.
Classen et al., "Rapid Plasticity of Human Cortical Movement Representation Induced by Practice," The Journal of Neurophysiology, vol. 79, No. 2, pp. 1117-1123 (Feb. 1998).
CNN.com, Health, "Lab Zaps Strokes with Magnetic Pulses," http://www.cnn.com/2004/HEALTH/conditions/11/29/zapping.strokes. ap/, Nov. 29, 2004, 4 pages [Retrieved on Dec. 2, 2004].
Cohen et al., "Studies of Neuroplasticity With Transcranial Magnetic Stimulation," The Journal of Clinical Neurophysiology, vol. 15, No. 4 (1998).
Cramer et al., "Use of Functional MRI to Guide Decisions in a clinical Stroke Trial," Stroke, Journal of the American Heart Association, May 2005, pp. e50-e52, American Heart Association, Dallas TX.
Cramer, S.C. and Bastings, E.P., "Mapping clinically relevant plasticity after stroke," Neuropharmacology vol. 19, No. 5, pp. 842-851 (Apr. 2000).
Cytokines Web Clinical Significance, Cytokines Web, 2 pages, URL: http:--cmbi.bjmu.edu.cn-cmbidata-cgf-CGF__Database-cytweb-roles-index.html [Retrieved on Sep. 2, 2005].
Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).
De Ridder, Dirk et al., "Magnetic and electrical stimulation of the auditory cortex for intractable tinnitus," Journal Neurosurg., vol. 100, pp: 560-564, (Mar. 2004).
Di Lazzaro, V. et al., "Theta-burst repetitive transcranial magnetic stimulation suppresses specific excitatory circuits in the human motor cortex," Physiology in Press; published online on Apr. 21, 2005 as 10.1113-jphysiol.2005.087288.
Ding, Yuemin et al., "Neural Plasticity After Spinal Cord Injury," Current Pharmaceutical Design vol. 11, No. 11, pp. 1441-1450, Abstract Only, 1 page (Apr. 2005).
Duncan, Pamela W. et al., "Defining post-stroke recovery: implications for design and interpretation of drug trials," Neuropharmacology vol. 39, pp. 835-841 (2000).
Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam, NL.

(56) References Cited

OTHER PUBLICATIONS

Feys et al., "Value of somatosensory and motor evoked potentials in predicting arm recovery after a stroke," (Oct. 1999).
Foster et al., "Transmitter expression and morphological development of embryonic medullary and mesencephalic raphé neurones after transplantation to the adult rat central nervous system. III. Grafts to the striatum," Exp Brain Res, Apr. 1988, 70(2):225-41, Springer Berlin/Heidelber.
Franzini et al., "Reversal of thalamic hand syndrome by long-term motor cortex stimulation," Journal of Neurosurgery 93(5):873-875, Nov. 2000.
Fregni et al., "Antiepileptic Effects of Repetitive Transcranial Magnetic Stimulation in Patients with Cortical Malformations: An EEG and Clinical Study," ASSFN Proceedings 2004, Stereotactic and Functional Neurosurgery, 2005, 83:57-62.
Fregni, Felipe et al., "Anodal Transcranial Direct Current Stimulation of Prefrontal Cortex Enhances Working Memory," Experimental Brain Research vol. 166, No. 1, pp: 23-30 (Sep. 2005).
Gash, D. M. et al., "Amitotic Neuroblastoma Cells Used for Neural Implants in Monkeys," Science, Sep. 26, 1986, vol. 233, No. 4771, pp. 1420-1422, Copyright © 1986 by American Association for the Advancement of Science.
Gladstone et al., "Enhancing Recovery after Stroke with Noradrenergic Pharmacotherapy: A New Frontier?" Can J. Neurol. Sci., vol. 27, No. 2, May 2000, pp. 97-105.
Gordon et al., "Parameters for direct cortical electrical stimulation in the human: histopathologic confirmation," Electroencephalography and clinical Neurophysiology, vol. 75, pp. 371-377 (1990).
Gupta et al., "Differentiation Characteristics of Human Neuroblastoma Cells in the Presence of Growth Modulators and Antimitotic Drugs," Developmental Brain Research, 19(1985)21-29, Elsevier.
Hagemann, Georg et al., "Increased Long-Term Potentiation in the Surround of Experimentally Induced Focal Cortical Infarction," Annals of Neurology, vol. 44, No. 2, pp. 255-258 (Aug. 1998).
Haglund, Michael M. et al., "Optical imaging of epileptiform and functional activity in human cerebral cortex," Nature, Aug. 20, 1992, pp. 668-671, vol. 358, Nature Publishing Group.
Hayakawa, Toshiji et al., "Changes in Cerebral Oxygenation and Hemodynamics During Obstructive Sleep Apneas," Chest, vol. 109, pp. 916-921 (1996).
Hodge, Jr., C.J. and Boakye, M., "Biological Plasticity: The Future of Science in Neurosurgery," Neurosurgery, vol. 48, No. 1 (Jan. 2001).
Hoshi, Yoko et al., "Detection of dynamic changes in cerebral oxygenation coupled to neuronal function during mental work in a man," Neuroscience Letters, vol. 150, pp. 5-8 (1993).
Hoshino et al., "Application of multichannel near-infrared spectroscopic topography to physiological monitoring of the cortex during cortical mapping: technical case report," Surgical Neurology, vol. 64, pp. 272-275 (2005).
How Imagent™ Works. ISS Inc., http://www.iss.com-Products-imagent_fmri.html, 1 page [Retrieved on Oct. 14, 2005].
Huang, Ying-Zu et al., "Theta Burst Stimulation of the Human Motor Cortex," Neuron, vol. 45, pp. 201-206 (Jan. 20, 2005).
Hummel, Friedhelm et al., "Effects of non-invasive cortical stimulation on skilled motor function in chronic stroke," Brain Advance Access, pp. 1-10, (Jan. 5, 2005).
Imagent™ Functional Brain Imaging System, ISS, Inc., http://www.iss.com-Products-imagent.html, 2 pages [Retrieved on Oct. 14, 2005].
Imagent™ functional Near Infrared Imaging System (fNIRS) Brain Imaging Using Infrared Photons, ISS Inc., http://www.iss.com-products-imagent-Imagent.pdf, 8 pages [Retrieved on Oct. 14, 2005].
Ishibashi, Tomoko et al., "Astrocytes Promote Myelination in Response to Electrical Impulses," Neuron 49, pp. 823-832, (Mar. 16, 2006).
Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).
Kauhanen et al., "Domains and Determinants of Quality of Life After Stroke Caused by Brain Infarction," Arch. Phys. Med. Rehabil., vol. 81, pp. 1541-1546 (Dec. 2000).
Kelly-Spratt, K. "Transfection of PC-12 cells: a model system for primary neuronal cells," Qiagen News, Customer application article, www.qiagen.com, Issue 4, 1998, 2 pages.
Keyvani, Kathy et al., "Suppression of proteasome C2 contralateral to ischemic lesions in rat brain," Brain Research, vol. 858, pp. 386-392, 2000.
Kilgard, Michael et al., "Cortical Map Reorganization Enabled by Nucleus Basalis Activity," Science, vol. 279 pp. 1714-1717 (Mar. 13, 1998).
Kimura et al., "Electrically induced neurite outgrowth of PC12 cells on the electrode surface," Med. Biol. Eng. Comput., Jul. 1998, vol. 36, No. 4, pp. 493-498, Springer Berlin / Heidelberg.
Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.
Kopell et al., "The Continuing Evolution of Psychiatric Neurosurgery," CNS Spectrums, vol. 5, No. 10, pp. 20-31 (Oct. 2000).
Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.
Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.
Larson, John et al., "Reversal of LTP by theta frequency stimulation," Brain Research, 600: pp. 97-102 (1993).
Lazar, M. et al., "White Matter Tractography Using Diffusion Tensor Deflection," Human Brain Mapping, 18:306-321, (2003).
L-Dopa dyskinesias, BioChemistry of PD, http://www.mayo.edu-fdp-pd-info-dyskinesias.htm [Retrieved on Dec. 22, 2005].
Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).
Liepert et al., "Treatment-Induced Cortical Reorganization After Stroke in Humans," Stroke, Jun. 2000, 31(6):1210-1216.
Lutsep et al., "Safety of Cortical Stimulation in Patients with Hemiparetic Stroke," Oasis, Online Abstract Submission and Invitation System—Program Planner, International Stroke Conference 2005, 1 page, American Stroke Association.
Malenka, R.C. and Nicoll, R.A., "Long-Term Potenetiation—A Decade of Progress?," Neuroscience, vol. 285, No. 5435, Issue of Sep. 17, 1999, pp. 1870-1874.
Mansur, C.G. et al., "A sham stimulation-controlled trial of rTMS of the unaffected hemisphere in stroke patients," Neurology, vol. 64, pp. 1802-1804 (2005).
Martin et al., "Transcranial Magnetic Stimulation as a Complementary Treatment for Aphasia," Semin Speech Language, vol. 25, pp. 181-191 (2004) Abstract Only—1 page.
Martinez et al., "Motor hand recovery after stroke Prognostic yield of early transcranial magnetic stimulation," Electromyogr. Clin. Neurophysiol., Oct.-Dec. 1999, 39(7):405-410.
Mendonca et al., "Directly applied low intensity direct electric current enhances peripheral nerve regeneration in rats," J Neurosci Methods, Oct. 30, 2003, 129(2):183-90.
Meyerson, B.A. et al., "Motor Cortex Stimulation as Treatment of Trigeminal Neuropathic Pain", Acta Neurochirurgica Supplementum, vol. 58, pp. 150-153 (1993).
Misawa et al., "Low-frequency transcranial magnetic stimulation for epilepsia partialis continua due to cortical dysplasia," Journal of the Neurological Sciences, vol. 234, 2005, pp. 37-39.
Montgomery, "Thalamic Stimulation," Neuroscience Pathways, The Cleveland Clinic Foundation, 2 pages.

(56) References Cited

OTHER PUBLICATIONS

Motamedi et al., "Optimizing Parameters for Terminating Cortical Afterdischarges with Pulse Stimulation," Epilepsia 43(8):836-846, 2002, Blackwell Publishing, Inc.
Netz et al., "Reorganization of motor output in the non-affected hemisphere after stroke," Brain, 120, pp. 1579-1586 (1997).
Nitsche, M.A. and Paulus, W., "Excitability changes induced in the human motor cortex by weak transcranial direct current stimulation," The Journal of Physiology, Sep. 15, 2000, 527(3):633-9.
Nitsche, Michael A. et al. "Facilitation of Implicit Motor Learning by Weak Transcranial Direct Current Stimulation of the Primary Motor Cortex in the Human," Journal of Cognitive Neuroscience, May 2003, 15(4):619-26, Published by the MIT Press with the Cognitive Neuroscience Institute.
Nitsche, Michael A. et al., "Level of action of cathodal DC opographyn induced inhibition of the human motor cortex," Dec. 2, 2002, Clinical Neurophysiology 114 (2003) 600-604.
Nudo, Randolph J. et al., "Recovery after damage to motor cortical areas," Current Opinion in Neurobiology, vol. 9, Issue 6, pp. 740-747, Dec. 1, 1999.
Oliveri et al., "Paired transcranial magnetic stimulation protocols reveal a pattern of inhibition and facilitation in the human parietal cortex," The Journal of Physiology, Dec. 1, 2000, 529.2, pp. 461-468.
Panchanathan, Sethuraman et al., "Rehabilitation of patients with hemispatial neglect using visual-haptic feedback in Virtual reality environment," http://www.public.asu.edu~tmcdani-publications.htm, 5 pages [Retrieved on Dec. 22, 2005].
Pascual-Leone et al., "Study and Modulation of Human Cortical Excitability With Transcranial Magnetic Stimulation," Journal of Clinical Neurophysiology, Jul. 1998, 15(4):333-43, Published by Lippincott Williams & Wilkins.
Pascual-Leone et al., "Transcranial magnetic stimulation and neuroplasticity," Neuropshychologia, Feb. 1999, 37(2):207-17.
Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.
Paulus, Walter, "Toward Establishing a Therapeutic Window for rTMS by Theta Burst Stimulation," Neuron, vol. 45, pp. 181-183 (Jan. 20, 2005).
Penn, Michael, "Stemming Parkinson's," On Wisconsin Alumni Magazine, Summer 2003, http://www.uwalumni.com-onwisconsin-2003_summer-research.html, 1 page [Retrieved on Dec. 22, 2005].
Politis, M. J., "Mammalian Optic Nerve Regeneration Following the Application of Electric Fields," The Journal of Trauma, Nov. 1988, vol. 28, No. 11, pp. 1548-1552.
Price, J. et al., "Neurotransplantation in neurodegenerative disease: a survey of relevant issues in developmental neurobiology," Novartis Foundation Symposium 231, 2000, pp. 148-165, Wiley, Chichester, UK. [Published Online: Sep. 26, 2003].
Rezai, "Neurostimulation," Neurological Research, vol. 22, No. 3 pp. 235-273 (Apr. 2000).
Robinson, Kenneth R., "The Responses of Cells to Electrical Fields: A Review," The Journal of Cell Biology, vol. 101, pp. 2023-2027 (Dec. 1985).
Rossi et al., "Effects of Repetitive Transcranial Magnetic Stimulation on Movement-related Cortical Activity in Humans," Cerebral Cortex, vol. 10, No. 8, pp. 802-808 (Aug. 2000).
Roux et al., "Chronic Motor Cortex Stimulation for Phantom Limb Pain: A Functional Magnetic Resonance Imagining Study: Technical Cast Report," Neurosurgery, vol. 48, No. 3 (Mar. 2001).
Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).
Sandkuhler, "Learning and memory in pain pathways," Pain, Nov. 2000, 88(2):113-18, Elsevier/North-Holland.
Sanes, "The Relation between Human Brain Activity and Hand Movements," NeuroImage, May 2000, 11(5), pp. 370-374.
Sanes, J. and Donoghue, J.P., "Plasticity and Primary Motor Cortex," Annual Review of Neuroscience, 2000, 23:393-415.
Schaefer, Pamela W. et al., "Assessing Tissue Viability with MR Diffusion and Perfusion Imaging," AJNR, 24: pp. 436-443 (Mar. 2003).
Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).
Schiff et al., "A neuromodulation strategy for rational therapy of complex brain injury states," Neurological Research, vol. 22 pp. 267-272 (Apr. 2000).
Schulz et al., "Localization of Epileptic Auras Induced on Stimulation by Subdural Electrodes," Epilepsia, Dec. 1997, vol. 38, Issue 12, pp. 1321-1329.
SCIRun, Scientific Computing and Imaging Institute. http://www.software.sci.utah.edu-scirun.html, 2 pages [Retrieved on Jul. 24, 2005].
Shimizu et al., "Therapeutic efficacy of transcranial magnetic stimulation for hereditary spinocerebellar degeneration," Tohoku Journal of Experimental Medicine, 189(3):203-11 (Nov. 1999).
Siebner et al., "Lasting cortical activation after repetitive TMS of the motor cortex," Neurology 54, pp. 956-963 (Feb. 2000).
Sioutos et al. Continuous Regional Cerebral Cortical Blood Flow Monitoring in Head-injured Patients, Neurosurgery, vol. 36, No. 5, May 1995, pp. 943-949.
Stefan et al., "Induction of plasticity in the human motor cortex by paired associative stimulation," Brain, vol. 123, No. 3, pp. 572-584 (Mar. 2000).
Storer et al., "Microiontophoretic application of serotonin (5HT)1B/1D agonists inhibits trigeminal cell firing in the cat," Brain, 1997, vol. 120, Issue 12, pp. 2171-2177, Oxford University Press.
Strangman, Gary et al., "A Quantitative Comparison of Simultaneous BOLD fMRI and NIRS Recordings during Functional Brain Activation," NeuroImage, vol. 17, pp. 719-731 (2002).
Strangman, Gary et al., "Factors affecting the accuracy of near-infrared spectroscopy concentration calculations for focal changes in oxygenation parameters," NeuroImage, vol. 18, pp. 865-879 (2003).
Strangman, Gary et al., "Non-Invasive Neuroimaging Using Near-Infrared Light," Biological Psychiatry, vol. 52, pp. 679-693 (2002).
Strens, Lucy et al., "The Ipsilateral Human Motor Cortex Can Functionally Compensate for Acute Contralateral Motor Cortex Dysfunction," Current Biology, vol. 13, pp. 1201-1205 (Jul. 15, 2003).
Suzuki et al., "Selective Electrical Stimulation of Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.
Taga, Gentaro et al., "Brain imaging in awake infants by near-infrared optical topogrpahy," PNAS, vol. 100, No. 19, pp. 10722-10727 (Sep. 16, 2003).
Tang, Cha-Min et al., "Optical Coherence Tomography of the Human Basal Ganglion," Deep Brain Stimulation Consortium Meeting Program Book, Sep. 29-30, 2003, Washington DC.
The GES 250 for Dense-Array EEG Research, Electrical Geodesics, Inc., http://www.egi.com/ges250r_n.html, 3 pages [Retrieved on Aug. 25, 2005].
The INVOS Cerebral Oximeter, Somanetics, http://www.somanetics.net/invos.htm, 1 page [retrieved from the internet on Dec. 22, 2005].
The National Institutes of Health (NIH) Consensus Development Program, "Surgery for Epilepsy," National Institutes of Health Consensus Development conference Statement, Mar. 19-21, 1990, 16 pages.
Theoret, Hugo et al., "Exploring Paradoxical Functional Facilitation with TMS," Supplements to Clinical Neurophysiology, vol. 56, pp. 211-219 (2003).
Thomas, Carmen et al., "Do Children with aggressive behavior have temporal lobe changes?" Alasbimn Journal, Year 5, No. 19, 8 pages (Jan. 2003).
Timmermann, Lars et al., "The cerebral oscillatory network of parkinsonian resting tremor," Brain, vol. 126, pp. 199-212, (2003).

(56) References Cited

OTHER PUBLICATIONS

Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).
Tractography, Absolute Astronomy Reference, http://www.absoluteastronomy.com-encyclopedia-T-Tr-Tractography.htm, 2 pages [Retrieved on Jul. 24, 2005].
Tsubokawa, T. et al., "Chronic Motor Cortex Stimulation for the Treatment of Central Pain," Acta Neurochirurgica, Supplementum. vol. 52, pp. 137-139 (1991).
Tsubokawa, T. et al., "Chronic Motor Cortex Stimulation in Patients with Thalamic Pain," J. Neurosurg 78:393-401, (Mar. 1993).
Tsubokawa, T. et al., "Treatment of Thalamic Pain by Chronic Motor Cortex Stimulation", PACE, vol. 14, pp. 131-134 (Jan. 1991).
Tuch, D. et al., "Conductivity Tensor Mapping of the Human Brain Using Diffusion Tensor MRI," Neurobiology, vol. 98 No. 20, pp. 11697-11701 (Sep. 25, 2001).
Turton et al., "Contralateral and ipsilateral EMG responses to transcranial magnetic stimulation during recovery of arm and hand function after stroke," Electroencephalography and Clinical Neurophysiology, Aug. 1996, 101(4):316-28, Elsevier.
Turton, A. and Lemon, R.N., "The contribution of fast corticospinal input to the voluntary activation of proximal muscles in normal subjects and in stroke patients," Exp. Brain Res., Dec. 1999, 129(4):559-572, Springer Berlin / Heidelberg.
Van Der Lee et al., "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).
Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.
Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, May-Jun. 2000, 31(3):304-315, Elsevier Science, Inc.
Velasco et al., "Electrical Stimulation for Epilepsy: Stimulation of Hippocampal Foci," Proceedings of the 13th Meeting of the World Society for Stereotactic and Functional Neurosurgery, Sep. 11-14, 2001, Stereotactic and Functional Neurosurgery, vol. 77, No. 1-4, 2001, pp. 223-227.
Velasco et al., "Subacute and Chronic Electrical Stimulation of the Hippocampus on Intractable Temporal Lobe Seizures: Preliminary Report," Archives of Medical Research, May-Jun. 2000, 31(3):316-28, Elsevier Science.
Velasco et al., "Subacute Electrical Stimulation of the Hippocampus Blocks Intractable Temporal Lobe Seizures and Paroxysmal EEG Activities," Epilepsia, Feb. 2000, 41(2):158-169, Lippincott Williams & Wilkins, Philadelphia.
Walker-Batson et al., "Amphetamine Paired With Physical Therapy Accelerates Motor Recovery After Stroke," Stroke, vol. 26, No. 12, pp. 2254-2259 (1995).
Waxman et al., "The Interictal Behavior Syndrome of Temporal Lobe Epilepsy," Arch Gen Psychiatry, vol. 32, Dec. 1975, pp. 1580-1586.
Weinand et al., "Cerebral blood flow and temporal lobe epileptogenicity," J Neurosurg, vol. 86, Feb. 1997, pp. 226-232.
Weinand et al., "Cerebral blood flow and temporal lobe epileptogenicity," Neurosurgical Focus, Nov. 1996, vol. 1, No. 5, AANS.ORG, http://www.aans.org/education/journal/neurosurgical/nov96/1-5-3.asp, 17 pages.
Weinand et al., Long-term ictal monitoring with subdural strip electrodes: prognostic factors for selecting temporal lobectomy candidates, J Neurosurg, vol. 77, 1992, pp. 20-28.
Weinand et al., "Surface cortical cerebral blood flow monitoring and single photon emission computed tomography: prognostic factors for selecting temportal lobectormy candidates," Seizure, vol. 3, 1994, pp. 55-59.
Weinand et al., "Targeted Subthreshold Cortical Stimulation for Recovery of Motor Hand Function following Hemiparetic Stroke," Abstract: Apr. 18, 2005, AANS.org, http://www.aans.org/Library/Article.aspx?ArticleId=24934, 2 pages.
Weinand, Martin E. et al., "Cerebral blood flow and temporal lobe epileptogenicity," Retrieved from the Internet on Dec. 22, 2005, http://www.aans.org/education/journal/neurosurgical/nov96/1-5-3.asp, 13 pages.
Woodbury, D. et al., "Adult Rat and Human Bone Marrow Stromal Cells Differentiate Into Neurons," Journal of Neuroscience Research, Aug. 15, 2000, 61(4):364-70, ,Wiley Interscience, New York, NY.
Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.
Yokoh, Arika et al., "Intermittent versus continuous brain retraction," Journal of Neurosurgery, vol. 58, pp. 918-923 (Jun. 1983).
Ziemann et al., "Modulation of Plasticity in Human Motor Cortex after Forearm Ischemic Nerve Block," The Journal of Neuroscience 18(3):1115-1123 (Feb. 1998).

300

| Mode | Description |
|---|---|
| Random PW - K%, K=5, 10, or 20 | Disable selected pulse width (up to 300 microseconds) for the first 100 milliseconds in K% of the 1-second intervals on a 300 second pseudorandom schedule if PRF > 20 Hz<br><br>Disable selected pulse width (up to 300 microseconds) for the first 200 milliseconds in K% of the 1-second intervals on a 300 second pseudorandom schedule if PRF <= 20 Hz |
| Periodic PW - P min. repeat, P = 1, 5 | Double the selected pUlse width (up to 300 microseconds) on a cyclic basis for the first 100 milliseconds of every P minutes for PRF > than 20 Hz, or for the first 200 milliseconds for PRF <= 20 Hz |
| Random Short Cycle - Q%, Q = 10, 25, 50, 75 | Enable therapy output at selected parameters on a 300 second pseudorandom schedule for 1 second intervals; output active for Q% of intervals |
| Random Long Cycle - R%, R = 10, 25, 50, 75 | Enable therapy output at selected parameters on a 60 minute pseudorandom schedule for 12 second intervals; output active for R% of intervals |
| Periodic Duty Cycle - S%, S = 10, 25, 50, 75 | Enable therapy output at selected parameters on a cyclic basis; ON S% of 120 second interval |
| Random PRF - T%, T = 5,10 | Double selected PRF (up to 150 Hz) for the first 100 milliseconds in T% of the 1-second intervals on a 300 second pseudorandom schedule if PRF > 20 Hz<br><br>Double selected PRF (up to 150 Hz) for the first 100 milliseconds in T% of the 1-second intervals on a·300 second pseudorandom schedule if PRF <= 20 Hz |
| Random Polarity - Bipolar | Set output polarity to one of two bipolar configurations every second on a 300 second pseudorandom schedule |
| Random Polarity - Alt. Unipolar | Set output polarity to one of four single contact unipolar configurations every second on a 300 second pseudorandom schedule |
| Random Polarity - Rev. Unipolar | Set output polarity to one of two dual contact unipolar configurations every second on a 300 second pseudorandom schedule |

FIG. 16

SYSTEMS AND METHODS FOR ENHANCING OR AFFECTING NEURAL STIMULATION EFFICIENCY AND/OR EFFICACY

CROSS-REFERENCE TO RELATED APPLICATIONS

This application is a continuation of U.S. application Ser. No. 12/327,711, filed Dec. 3, 2008, now U.S. Pat. No. 7,983,762, which is a divisional of U.S. application Ser. No. 11/182,713, filed Jul. 15, 2005, now U.S. Pat. No. 7,483,747, which claims the benefit of U.S. Provisional Application No. 60/588,406, filed Jul. 15, 2004, the disclosures of which are incorporated herein by reference.

TECHNICAL FIELD

The present disclosure relates to adjusting time dependent device operation parameters, location dependent device operation parameters, and/or waveform delivery parameters to affect neural stimulation energy consumption and/or efficacy. More particularly, this disclosure relates to systems and methods directed toward altering device operation characteristics.

BACKGROUND

Neural activity in the brain can be influenced by electrical energy that is supplied from a waveform generator or other type of device. Various patient perceptions and/or neural functions can thus be promoted or disrupted by applying an electrical or magnetic signal to the brain. As a result, researchers have attempted to treat various neurological conditions using electrical or magnetic stimulation signals to control or affect brain functions. For example, Deep Brain Stimulation (DBS) has shown promising results for reducing some of the symptoms associated with Parkinson's Disease, which results in movement or muscle control problems and is debilitating to a great number of individuals worldwide.

Neural activity is governed by electrical impulses or "action potentials" generated in and propagated by neurons. While in a quiescent state, a neuron is negatively polarized, and exhibits a resting membrane potential that is typically between −70 and −60 mV. Through electrical or chemical connections known as synapses, any given neuron receives from other neurons excitatory and inhibitory input signals or stimuli. A neuron integrates the excitatory and inhibitory input signals it receives, and generates or fires a series of action potentials in the event that the integration exceeds a threshold potential. A neural firing threshold may be, for example, approximately −55 mV. Action potentials propagate to the neuron's synapses, where they are conveyed to other neurons to which the neuron is synaptically connected.

A neural stimulation system may comprise a pulse generator and an electrode assembly. One or more portions of a neural stimulation system may be implanted in a patient's body. For example, an implanted pulse generator may commonly be encased in a hermetically sealed housing and surgically implanted in a subclavicular location. An electrode assembly may be implanted to deliver stimulation signals to a stimulation site, and is electrically coupled to the pulse generator via biocompatibly sealed lead wires. A power source is contained within the housing of the pulse generator and is generally a battery.

Neural stimulation is generally delivered or applied to a patient in accordance with a treatment protocol. Typically, a treatment protocol specifies an optimal or best set of neural stimulation parameters directed toward maximally alleviating one or more patient symptoms through neural stimulation applied in a continuous, generally continuous, or nearly continuous manner. Unfortunately, under a conventional treatment protocol, neural stimulation efficacy may wane or degrade over time.

Since a battery has a finite charge storage capacity, a battery will expire or become depleted, thereby interrupting the patient's treatment. Various types of neural stimulation systems may include a nonrechargable battery that may last approximately two to three years. After an implanted battery is exhausted, another surgery is typically required to replace the pulse generator. As with any surgery, complications may arise, and subsequent incisions to the implanted site may prove troublesome due to scar tissue, implantation site sensitivities, and/or other conditions.

BRIEF DESCRIPTION OF THE DRAWINGS

FIG. 16 provides a list of representative types of stimulation signal parameter variation modes that may be programmably selected in association with an IPG programming session.

DETAILED DESCRIPTION

Introduction

Figure 1A:
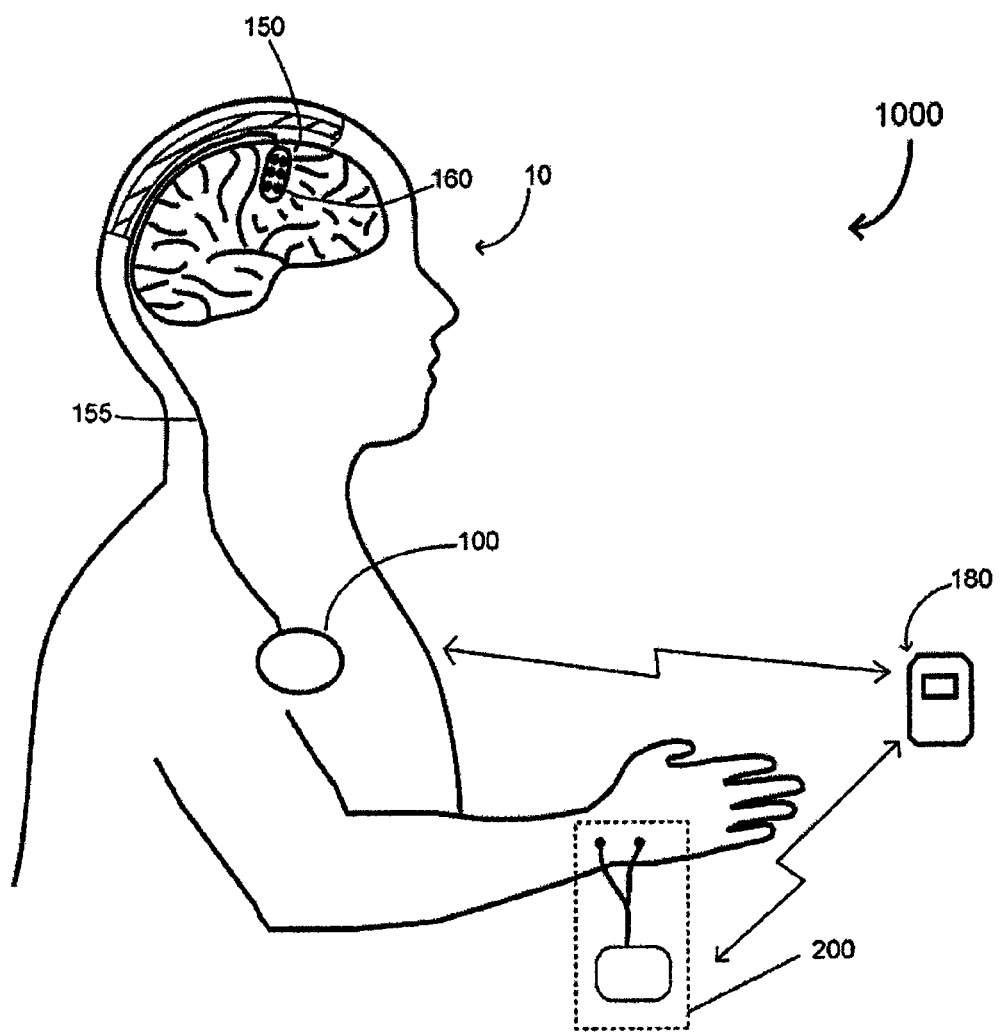
FIGS. 1A-1C are schematic illustrations of neural stimulation systems according to embodiments of the invention.

The following disclosure describes a system and method for affecting neural stimulation efficiency and/or efficacy. Various embodiments of systems and/or methods described herein may be directed toward controlling, adjusting, modifying, and/or varying one or more manners in which neural stimulation may be applied or delivered to a patient, thereby possibly 1) prolonging or extending the life and/or recharging interval associated with a power source such as a battery; and/or 2) influencing, affecting, maintaining, or improving neural stimulation efficacy. The neural stimulation may comprise electrical and/or magnetic stimulation signals, and may be defined in accordance with spatial, temporal, electrical, and/or magnetic signal parameters, properties, and/or characteristics.

The application of neural stimulation in accordance with particular embodiments of the invention may affect neural stimulation efficacy at one or more times through one or more mechanisms, which may be analogous, generally analogous, or somewhat analogous to Long Term Potentiation (LTP) and/or Long Term Depression (LTD). The application of neural stimulation in accordance with certain embodiments of the invention may additionally or alternatively affect neural stimulation efficacy at one or more times by affecting neural processes that are related or generally related to tolerance, adaptation, habituation, and/or sensitization. One or more effects associated with or arising from the application of neural stimulation in accordance with certain embodiments of the invention may correspond to neuroplastic, neuroregenerative, neuroprotective, and/or neurogenic effects.

In accordance with particular embodiments of the invention, the neural stimulation may correspond to transcranial, cortical, subcortical, cerebellar, deep brain, spinal column, cranial or other peripheral nerve, and/or other types of stimulation. Such stimulation can be provided, delivered, or achieved using a variety of devices and/or techniques. By way of example, the neural stimulation can be applied or delivered through the use of a neural stimulation device that can be, but does not necessarily have to be, implanted within the patient's body. Such a neural stimulation device may comprise a pulse generator coupled to at least one electrode assembly. In many cases, a main source of power for a neural stimulation device comprises a battery and/or a capacitor. Batteries that are employed for implantable neural stimulators can store a finite amount of charge or energy. The exact length of a battery's life depends upon battery usage, as well as the materials used to construct the battery.

In accordance with various embodiments of the invention, a treatment program may specify, define, and/or indicate one or more manners of treating, affecting, or influencing one or more types of neurologic dysfunction, functional deficits, conditions, and/or symptoms in an effective or adequate manner. A treatment program may comprise and/or be defined in accordance with one or more neural stimulation procedures; drug, growth factor, neurotrophic agent, and/or other chemical substance procedures; behavioral therapy procedures; and/or patient assessment procedures, as further described below.

The length or duration of one or more portions of a treatment program, and possibly the type(s) and/or location(s) of applied neural stimulation, may depend upon the nature, extent, and/or severity of the patient's condition, functional deficits, and/or neurologic dysfunction; a degree of patient recovery or functional development over time; and/or embodiment details. A treatment program in accordance with various embodiments of the present invention may facilitate and/or effectuate at least some degree of symptomatic relief and/or restoration or development of functional abilities in patients experiencing neurologic dysfunction arising from neurological damage, neurologic disease, neurodegenerative conditions, neuropsychiatric disorders, neuropsychological (e.g., cognitive or learning) disorders, and/or other conditions. Such neurologic dysfunction and/or conditions may correspond to Parkinson's Disease, essential tremor, Huntington's disease, stroke, traumatic brain injury (TBI), Cerebral Palsy, Multiple Sclerosis, a pain syndrome (e.g., associated with a central and/or peripheral pain condition, such as phantom limb pain, trigeminal neuralgia, trigeminal neuropathic pain, sympathetically maintained pain, postsurgical pain, or other conditions), a memory disorder, dementia, Alzheimer's disease, an affective disorder, depression, bipolar disorder, anxiety, obsessive/compulsive disorder, Post Traumatic Stress Disorder (PTSD), an eating disorder, schizophrenia, Tourette's Syndrome, Attention Deficit Disorder, a phobia, an addiction, autism, epilepsy, a sleep or sleep-related disorder, a hearing disorder, a language disorder, a speech disorder (e.g., stuttering), epilepsy, migraine headaches, dysfunction associated with an autonomic system or internal organ, and/or one or more other disorders, states, or conditions.

In some embodiments, a treatment program may be directed toward long term neural stimulation, for example, when directed toward treating significantly or severely progressed conditions. In certain embodiments, a treatment program may involve one or more types of neural stimulation across the duration of a patient's life. Alternatively, a treatment program may be directed toward limited duration neural stimulation. For example, a treatment program may be applied over one or more limited time intervals that correspond to an extent of the patient's recovery or functional gain(s). Alternatively or additionally, a treatment program may be applied over a predetermined number of days, weeks, months, and/or years; and/or a predetermined number of treatment sessions, for example, twenty, thirty, fifty, or some other number of treatment sessions in total. A treatment program may also temporally span an accumulated or aggregate amount of time that stimulation has been applied (e.g., in a continuous, generally continuous, or interrupted manner) or over some amount of time and/or some number of treatment sessions. Various aspects of limited duration treatment programs are described in U.S. application Ser. No. 10/606,202, entitled Methods and Apparatus for Effectuating a Lasting Change in a Neural-Function of a Patient, filed on Jun. 24, 2003, incorporated herein in its entirety by reference.

In certain embodiments, a limited duration treatment program may be applied to a patient; followed by an interruption period; followed by another limited duration treatment program; possibly followed by another interruption period, and so on. An interruption period may comprise one or more rest, neural consolidation, strengthening, and/or activity practice periods. The length or duration of any given interruption period may depend upon patient condition; the nature of prescribed, allowable, or acceptable patient activities corresponding to the interruption period; an extent to which one or more symptomatic benefits is maintained or improved; and/or other factors.

In particular embodiments, a limited duration treatment program and/or an interruption period may involve peripheral or functional electrical stimulation (FES), during which electrical signals are applied to peripheral nerves and/or muscles. For example, in accordance with one type of limited duration treatment program, a patient may undergo an FES session (e.g., for approximately 5-45 minutes) prior to a cortical, deep brain, spinal column, or vagal nerve stimulation session, which may occur in association or conjunction with a behavioral task or therapy. A limited duration treatment program may additionally or alternatively specify that central nervous system (CNS) stimulation and FES may be applied in a simultaneous, essentially simultaneous, or near simultaneous manner, for example, timed relative to each other in accordance with a measured or estimated central-peripheral neural signal conduction time.

In accordance with one type of interruption period, a patient may undergo periodic (e.g., daily) FES sessions before and/or after a given limited duration treatment program. The FES sessions may occur prior to patient performance or attempted performance of one or more muscular strengthening tasks or other activities. In general, the characteristics of any given limited duration treatment program and/or those of any particular interruption period may be based upon the nature and/or extent of a patient's neurologic dysfunction, an expected level of patient benefit, and/or embodiment details.

A method for treating a neurological condition of a patient in accordance with a particular aspect of the invention includes applying electromagnetic stimulation to a patient's nervous system over a first time domain with a first wave form having a first set of parameters. The method can further include applying electromagnetic stimulation to the patient's nervous system over a second time domain with a second wave form having a second set of parameters, wherein at least one parameter of the second set is different than a corresponding parameter of the first set. In one specific aspect, the second time domain can be sequential to the first time domain. In another specific aspect, multiple second time domains can be nested within the first time domain.

The method can further include interrupting the application of electromagnetic stimulation between the first and second time domains, and selecting the at least one parameter of the second set to reduce power consumption due to electrical stimulation during the second time domain, compared with power consumption due to electrical stimulation during the first time domain. In still further aspects, the electromagnetic stimulation during at least one of the time domains can be varied aperiodically, for example, chaotically, or otherwise.

Apparatuses in accordance with further aspects of the invention can include a stimulation device having at least one stimulator (e.g., an electrode) configured to be positioned in signal communication with neural tissue of a patient's nervous system. The apparatus can further include a signal generator and a signal communication link operatively coupled between the stimulation device and the signal generator. The apparatus can still further include a controller operatively coupled to the signal generator. In one particular aspect, the controller can be configured to provide instructions to the signal generator that direct an application of electromagnetic stimulation to the patient's nervous system over a first time domain with a first wave form having a first set of parameters, and over a second time domain with a second wave form having a second set of parameters. At least one parameter of the second set can be different than a corresponding parameter of the first set.

In other aspects, the controller can be configured to provide instructions to the signal generator to direct an application of electromagnetic stimulation to the patient in a manner that varies aperiodically, for example, in a chaotic or other fashion. In still another aspect, the controller can be configured to provide instructions to the signal generator to direct an application of electromagnetic stimulation to the patient in a manner that varies at least generally similarly to naturally occurring brain wave variations. For example, the controller can be configured to provide instructions to direct an application of electromagnetic stimulation having a burst frequency and an intra-burst frequency greater than the burst frequency. In particular embodiments, characteristics of the intra-burst stimulation may vary from one burst to another. In other embodiments, the inter-burst frequency can be generally similar to naturally occurring alpha, beta, gamma, delta, or theta brain wave frequencies.

Neural Stimulation Systems

FIG. 1A is a schematic illustration of a neural stimulation system 1000 according to an embodiment of the invention. One or more portions of a neural stimulation system 1000 may be implanted in a patient 10 and configured to supply, apply, and/or deliver electrical signals or pulses to one or more stimulation sites. In one embodiment, the neural stimulation system 1000 comprises at least one stimulation signal generator, which may communicate with a programming unit 180. In various embodiments, the stimulation signal generator may comprise an Implantable Pulse Generator (IPG) 100 and at least one electrode assembly 150 that are coupled by a set of electrically conductive lead wires 155 or another suitable signal communication link. Depending upon embodiment details, lead wires 155 may be implanted and/or positioned subcutaneously in a tunnel from a subclavicular region, along the back of the neck, and around a patient's skull 30. One or more electrode assemblies 150 may be surgically located, placed, or positioned relative to a set of stimulation sites, for example, at, within, and/or proximate one or more areas or regions to be stimulated. In other embodiments, the stimulation signal generator may comprise one or more microstimulators, such as a Bionic Neuron or BION™ (Advanced Bionics Corp., Sylmar, Calif.).

In general, a stimulation site may be defined as an anatomical location or region at which neural stimulation signals may be applied to a patient. Application of stimulation signals to a stimulation site may result in the application or delivery of such signals to and/or through one or more target neural populations, where such populations may correspond to a type of neurologic dysfunction. The number of stimulation sites under consideration at any given time may depend upon the nature of the patient's neurologic dysfunction and/or embodiment details. A stimulation site may correspond to a cortical, subcortical, deep brain, spinal column, cranial or other peripheral nerve, and/or other neural location, area, or region.

A set of target neural populations and/or stimulation sites may be identified based upon one or more structural neuroanatomical localization procedures; and/or spatial and/or temporal functional neuroanatomical localization procedures. Such procedures may involve Magnetic Resonance Imaging (MRI), functional MRI (fMRI), Diffusion Tensor Imaging (DTI), Perfusion Weighted Imaging (PWI), Electroencephalography (EEG), and/or other techniques. A set of target neural populations and/or stimulation sites may additionally or alternatively be identified based upon one or more anatomical landmark identification procedures, silent period analyses, coherence-based analyses, Transcranial Magnetic Stimulation (TMS) procedures, and/or other procedures. Sample manners of identifying a target neural population and/or a stimulation site are described in U.S. patent application Ser. No. 09/802,808, entitled "Methods and Apparatus for Effectuating a Lasting Change in a Neural-Function of a Patient," filed on Mar. 8, 2001; U.S. patent application Ser. No. 10/410,526, entitled "Methods and Apparatus for Effectuating a Lasting Change in a Neural-Function of a Patient," filed on Apr. 8, 2003; U.S. patent application Ser. No. 10/731,731, entitled "System and Method for Treating Parkinson's Disease and Other Movement Disorders," filed on Dec. 9, 2003; U.S. patent application Ser. No. 10/782,526, entitled "Systems and Methods for Enhancing or Optimizing Neural Stimulation Therapy for Treating Symptoms of Parkinson's Disease and/or Other Neurological Dysfunction," filed on Feb. 19, 2004; and U.S. patent application Ser. No. 10/731,892, entitled "Methods for Treating and/or Collecting Information Regarding Neurological Disorders, Including Language Disorders," filed on Dec. 9, 2003, each of which is incorporated herein by reference.

Figure 1B:
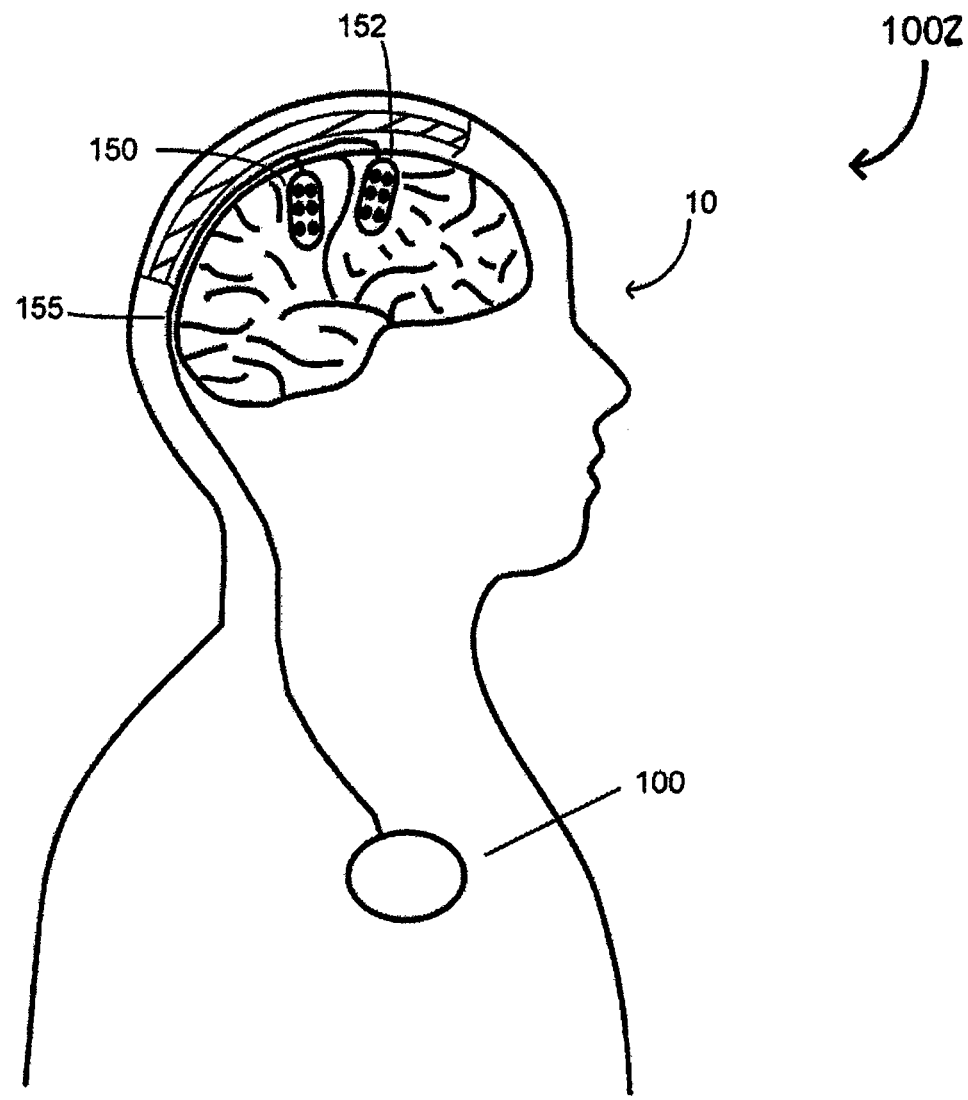

FIG. 1B is a schematic illustration of a neural stimulation system 1002 according to another embodiment of the invention. Relative to FIG. 1A, like reference numbers may indicate like or analogous elements. In one embodiment, the neural stimulation system 1002 comprises an IPG 100 coupled to a first electrode assembly 150 and a second electrode assembly 152. Each electrode assembly 150, 152 may correspond to a different stimulation site. For example, the first electrode assembly 150 may be positioned to apply or deliver stimulation signals to one or more portions of the primary motor cortex, while the second electrode assembly 152 may be positioned to apply stimulation signals to one or more portions of the premotor cortex, the supplementary motor area (SMA), Broca's area, and/or another neural area. As another example, the first electrode assembly 150 may be positioned to apply stimulation signals to one or more portions of the prefrontal cortex, while the second electrode assembly 152 may be positioned to apply stimulation signals to one or more portions of the motor cortex, the somatosensory cortex, the visual cortex, and/or another neural location.

FIG. 10 is a schematic illustration of a neural stimulation system 1004 according to another embodiment of the invention. Relative to FIGS. 1A and 1B, like reference numbers may indicate like or analogous elements. In one embodiment, the neural stimulation system 1004 comprises a first and a second electrode assembly 150, 152, which may be positioned in the same hemisphere or different hemispheres. In certain embodiments, the neural stimulation system 1004 may comprise additional electrode assemblies, for example, a third electrode assembly 154 and a fourth electrode assembly 156, which may be positioned in the same hemisphere or different hemispheres. Stimulation sites in different hemispheres may be homologous or nonhomologous, depending upon the nature of the patient's neurologic dysfunction and/or embodiment details. Depending upon embodiment details, the neural stimulation system 1004 may comprise at least a first IPG 100, and possibly a second IPG 102. The first IPG 100 may be coupled, for example, to the first and second electrode assemblies 150, 152, while the second IPG 102 may be coupled to the third and fourth electrode assemblies 154, 156. Accordingly, each IPG can direct signals to different electrode assemblies. In other embodiments different IPGs can direct signals over different time domains, which are described later.

In certain embodiments, one or more electrode assemblies 150 may additionally or alternatively be positioned and/or configured to sense, detect, or monitor neuroelectric activity corresponding to a set of monitoring sites. A monitoring site may be identical to or different from a stimulation site. In one embodiment, a single electrode assembly 150 may be configured both for applying stimulation signals and monitoring neuroelectric activity. In such an embodiment, stimulation and monitoring operations may typically occur in a sequential or temporally interrupted manner. In certain embodiments, an electrode assembly 150 may include one or more sensing elements to monitor, for example, thermal, neurochemical, and/or other types of neural and/or neural correlate activity.

An electrode assembly 150 may carry one or more electrodes or electrical contacts 160 configured to provide, deliver, and/or apply stimulation signals to neural tissue, for example, one or more cortical regions of the patient's brain 20 and/or neural populations synaptically connected and/or proximate thereto. Such electrical contacts 160 may additionally or alternatively sense, detect, or monitor neuroelectric activity. Examples of electrode assemblies 150 suitable for cortical and/or other types of stimulation are described in U.S. Patent Application No. 60/482,937, entitled "Apparatuses and Systems for Applying Electrical Stimulation to a Patient", filed Jun. 26, 2003; and U.S. patent application Ser. No. 10/418,796, entitled "Methods and Systems Employing Intracranial Electrodes for Neurostimulation and/or Electroencephalography," filed on Apr. 18, 2003, both of which are incorporated herein by reference.

Depending upon embodiment details, an electrode assembly 150 may comprise, include, and/or provide one or more stimulation signal return electrodes (i.e., electrodes that facilitate electrical continuity or provide a current return path) that may be positioned relative to a one or more locations within and/or upon the patient's body. A return electrode may be positioned at a remote location relative to a set of electrodes or electrical contacts 160 configured to apply or deliver stimulation signals to a target neural population, thereby facilitating the delivery of unipolar stimulation signals to a target neural population one or more times. Representative unipolar stimulation procedures and devices are described in U.S. application Ser. No. 10/910,775, entitled Apparatus and Method for Applying Neurostimulation to a Patient, filed on Aug. 2, 2004, incorporated herein by reference in its entirety. In general, the configuration, characteristics, and/or placement of an electrode assembly 150, a set of electrical contacts 160, and/or a return electrode may depend upon the nature of the patient's condition or underlying disorder(s), the type and/or severity of symptoms that the patient 10 experiences or exhibits, and/or embodiment details.

As shown in FIG. 1A, in some embodiments, a neural stimulation system 1000 may further include one or more patient monitoring devices, units, and/or systems 200 configured to detect, record, monitor, indicate, characterize, measure, calculate, and/or assess signals, data, or information corresponding to a patient state, condition, function, and/or the severity of particular types of patient symptoms. Depending upon embodiment details, one or more portions of a patient monitoring unit 200 may be external or internal to the patient 10. A patient monitoring unit 200 may be configured for communication with an external programming device 180. In one embodiment, portions of a patient monitoring unit 200 may be incorporated into an IPG 100.

A patient monitoring unit 200 may comprise, for example, one or more devices configured to measure, perform calculations upon, and/or analyze particular types of electrophysiological signals, such as EMG, EEG, and/or MEG signals. A patient monitoring unit 200 may alternatively or additionally comprise a cerebral bloodflow monitor. In certain embodiments, a patient monitoring unit 200 may comprise a neural imaging system, for example, an MRI-based system, a PET system, and/or an optical or other type of tomography system. In particular embodiments, a patient monitoring unit 200 may comprise one or more devices configured to provide neural stimulation, for example, a TMS device. In some embodiments, a patient monitoring unit 200 may comprise a set of devices configured to measure and/or calculate cerebro-muscular and/or cerebro-cerebral coherence and/or partial coherence; event-related desynchronization information; power and/or frequency spectra information; silent period (e.g., cortical and/or peripheral silent period) information; and/or other information.

A patient monitoring unit 200 may additionally or alternatively comprise one or more devices for facilitating characterization, assessment, and/or evaluation of particular symptoms and/or patient performance relative to one or more behaviors, tasks, and/or tests. Such devices may comprise, for example, motion sensors; accelerometers; force, torque, and/or strain sensors and/or gauges; and/or other devices. The collection of information indicative of the efficacy and/or efficiency of neural stimulation may aid in selecting, defining, modifying, updating, and/or adjusting one or more portions of a treatment program. In certain embodiments, a patient monitoring unit 200 may be implemented in one or more manners described in U.S. patent application Ser. No. 10/782,526, entitled "Systems and Methods for Enhancing or Optimizing Neural Stimulation Therapy for Treating Symptoms of Parkinson's Disease and/or Other Neurological Dysfunction," filed on Feb. 19, 2004, incorporated herein by reference.

In certain embodiments described herein, cortical stimulation is illustrated. However, various embodiments of the present invention may employ other or additional neural stimulation systems and/or devices, such as, but not limited to, systems and/or devices configured to apply transcranial electrical stimulation (TES); spinal column stimulation (SCS); vagal, cranial, and/or other peripheral nerve stimulation (VNS); cerebellar stimulation; and/or deep brain stimulation (DBS).

In such cases, an electrode assembly 150 may comprise one or more transcranial, nerve cuff, penetrating, depth, deep brain, and/or other types of electrodes or electrode assemblies (not shown). For example, in an alternate embodiment, the electrode assembly 150 may be configured to position electrodes, signal transfer devices, or electrical contacts 152 relative to the vagus and/or other cranial nerve; a spinal column region; and/or a subcortical and/or a deep brain region. In certain embodiments, a treatment program may additionally or alternatively involve TMS, in which case a neural stimulation system may comprise a coil-type arrangement for delivering magnetic stimulation signals to the patient 10.

Figure 2A:
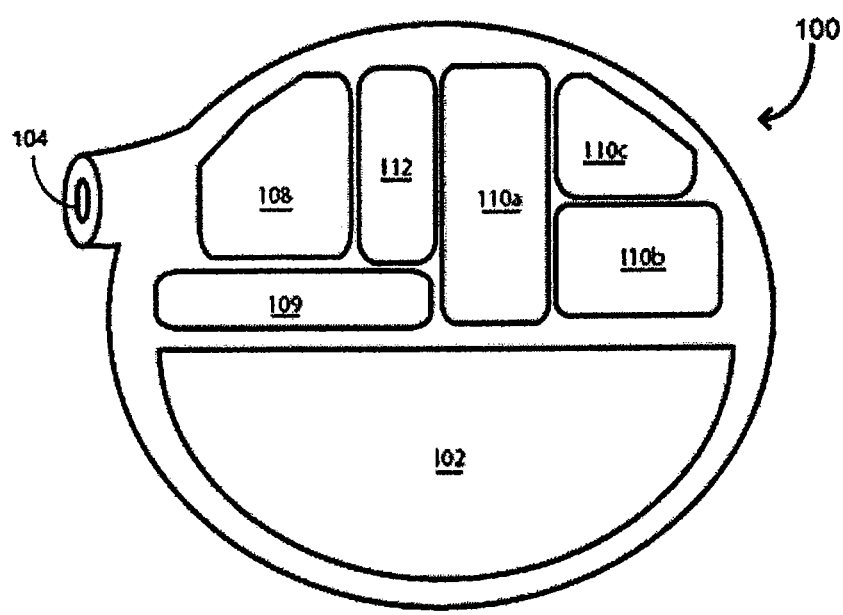
FIG. 2A is an internal block diagram of a stimulation signal generator or an implantable pulse generator (IPG) according to an embodiment of the invention.

FIG. 2A is an internal block diagram of a stimulation signal generator or an IPG 100 according to an embodiment of the invention. In one embodiment, the IPG 100 comprises a hermetically sealed housing 106 that houses a power source 102 as well as a controller 108, a telemetry and/or communication unit 110a, and at least one signal or pulse generating unit 110b. The IPG 100 may also comprise a switching unit 110c. Depending upon embodiment details, the IPG 100 may further comprise at least one programmable computer medium (PCM) 109, which may be coupled to the controller 108, the telemetry/communication unit 110a, the pulse generating unit 110b, and/or the switching unit 110c. The IPG 100 may additionally comprise at least one timing unit 112. Finally, in various embodiments the IPG 100 comprises at least one output or header structure 104 that facilitates electrical and mechanical coupling to an electrode lead structure.

The power source 102 typically comprises a charge storage device such as a battery. In some embodiments, the power source 102 may additionally or alternatively comprise another type of device for storing charge or energy, such as a capacitor. The controller 108, the PCM 109, the telemetry/communication unit 110a, the pulse generating unit 110b, the switching unit 110c, and/or the timing unit 112 may comprise integrated circuits and/or microelectronic devices that synergistically produce and manage the generation, output, and/or delivery of stimulation signals. In certain embodiments, one or more elements within the IPG 100 (e.g., the communication unit 110a, the pulse generating unit 110b, the switching unit 110c, and/or other elements) may be implemented using an Application Specific Integrated Circuit (ASIC).

The timing unit 112 may comprise a clock or oscillator and/or circuitry associated therewith configured to generate or provide a set of timing reference signals to the controller 108, the PCM 109, the telemetry/communication unit 110a, the pulse generating unit 110b, the switching unit 110c, and/or one or more portions, subelements, or subcircuits of the IPG 100. Such elements, subelements, and/or subcircuits may correlate or synchronize one or more operations to one or more timing reference signals, including the generation of other signals in a manner understood by those skilled in the art.

The controller 108 may control, manage, and/or direct the operation of elements within the IPG 100, possibly on a continuous, near-continuous, periodic, or intermittent basis depending upon embodiment details. The controller 108 may comprise one or more portions of an integrated circuit such as a processing unit or microprocessor, and may be coupled to a programmable computer medium (PCM) 109. The PCM 109 may comprise one or more types of memory including volatile and/or nonvolatile memory, and/or one or more data or signal storage elements or devices. The PCM 109 may store an operating system, program instructions, and/or data. The PCM 109 may store treatment program information, IPG configuration information, and stimulation parameter information that specifies or indicates one or more manners of generating and/or delivering stimulation signals in accordance with particular embodiments of the invention.

Figure 3A:
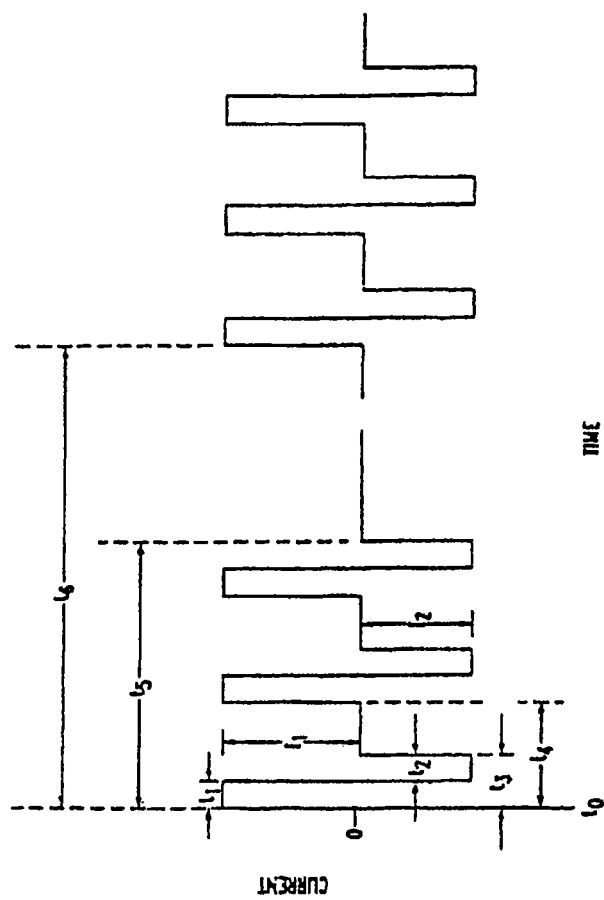
FIG. 3A is a graph illustrating several stimulation signal parameters that may at least partially describe, define, or characterize a stimulation signal or waveform according to an embodiment of the invention.

The pulse generating unit 110b may comprise hardware and/or software for generating and outputting stimulation signals. FIG. 3A is a graph illustrating several stimulation signal parameters that may at least partially describe, define, or characterize a stimulation signal or waveform according to an embodiment of the invention. A stimulus start time $t_0$ may define an initial point at which a stimulation signal is applied to one or more target neural populations. In one embodiment, the stimulation signal may be a symmetric or an asymmetric biphasic waveform comprising a set or series of biphasic pulses, and which may be defined, characterized, or defined by parameters including a pulse width $t_1$ for a first pulse phase; a pulse width $t_2$ for a second pulse phase; and a pulse width $t_3$ for a single biphasic pulse.

Stimulation signal parameters may also include a stimulus repetition rate $1/t_4$ corresponding to a pulse repetition frequency; a stimulus pulse duty cycle equal to $t_3$ divided by $t_4$; a stimulus burst time $t_5$ that defines a number of pulses in a pulse train; and/or a pulse train repetition rate $1/t_6$ that defines a stimulus burst frequency. Other parameters may include peak current amplitude $I_1$ for the first pulse phase and a peak current amplitude $I_2$ for a second pulse phase. Those skilled in the art will understand that pulse amplitude may decay during one or both pulse phases, and a pulse may be a charge-balanced waveform. Those skilled in the art will further understand that in an alternate embodiment, pulses can be monophasic or polyphasic. Moreover, in certain embodiments, a pulse train may comprise predetermined, pseudorandom, and/or aperiodic combinations of monophasic, biphasic, and/or polyphasic pulse sequences.

In some embodiments, a stimulation signal generator may generate or output a direct current (DC) signal. Such a signal may be applied transcranially at one or more times, either alone or in association with one or more other types of neural stimulation (e.g., VNS, cortical stimulation, or DBS). An example of a transcranial Direct Current Stimulation (tDCS) neural stimulation system is described by W. Paulus in "Transcranial Direct Current Stimualtion," chapter 26 of *Transcranial Magnetic Stimulation and Transcranial Direct Current Stimulation—supplements to Clinical Neurophysiology*, vol. 56, Edited by W. Paulus et al., Elsevier Science.

In various embodiments, a stimulation signal generator or pulse generator 110b may generate or output stimulation signals at one or more suprathreshold and/or subthreshold amplitudes, levels, intensities, or magnitudes at one or more times. The application of neural stimulation at a suprathreshold level may raise neural membrane potentials corresponding to a set of target neural populations such that the neural stimulation itself generates or elicits a sufficient or statistically significant number of action potentials capable of triggering a neural function corresponding to one or more such target neural populations. In contrast, the application of neural stimulation at a subthreshold level may raise or generally raise membrane potentials corresponding to a set of target neural populations while avoiding the generation of a sufficient or statistically significant number of action potentials capable of triggering a neural function corresponding to such target neural populations as a result of the subthreshold stimulation alone. Thus, the subthreshold stimulation by itself, in the absence of additional neural input (e.g., arising from neurofunctionally relevant patient behavior and/or additional stimulation signals), fails to drive a neural function corresponding to a target neural population or ensemble to which it is directed.

Depending upon embodiment details, a subthreshold stimulation amplitude may correspond to a particular fraction or percentage of a lowest or near lowest test stimulation signal amplitude at which a patient exhibits a particular type of response such as a movement, a sensation, and/or generation of an electrophysiological signal. For example, if a patient exhibits a movement in response to a test stimulation signal approximately equal to or just exceeding 6 mA, a treatment program may indicate a subthreshold stimulation amplitude of 3 mA, or approximately 50% of the patient's movement threshold. The magnitude of a subthreshold stimulation signal at any given time may depend upon the location and/or characteristics of a target neural population to which it is applied or directed.

In some embodiments, the pulse generating unit 110b may generate or output stimulation signals in accordance with one or more mathematical operations and/or functions upon or corresponding to particular stimulation signal parameters (e.g., a pulse width, a pulse repetition frequency, a peak amplitude, and/or a burst characteristic). Such functions or operations may facilitate the generation of stimulation signals exhibiting periodic, quasi-periodic, aperiodic, self-similar, chaotic, random, and/or pseudorandom characteristics at one or more times. In certain embodiments in which stimulation parameter values may vary, one or more parameter values may be limited or bounded in the event that the avoidance of unnecessary suprathreshold stimulation or suprathreshold stimulation exceeding a given level or duration is desirable. Appropriate limits or bounds may be determined experimentally, and/or estimated, e.g., through the use of one or more estimation functions (which may be based upon empirical and/or statistical information).

In certain embodiments, the pulse generating unit 110b may generate or output stimulation signals having particular parameter values (e.g., a pulse repetition frequency, a peak amplitude, and/or a burst characteristic) that are determined in accordance with a probability function or an occurrence distribution. An occurrence distribution may apply within or across one or more time intervals or domains, for example, a subseconds-based, seconds-based, minute-based, hours-based, or other type of time domain. In such embodiments, parameter values may be magnitude and/or range limited.

Figure 3B:
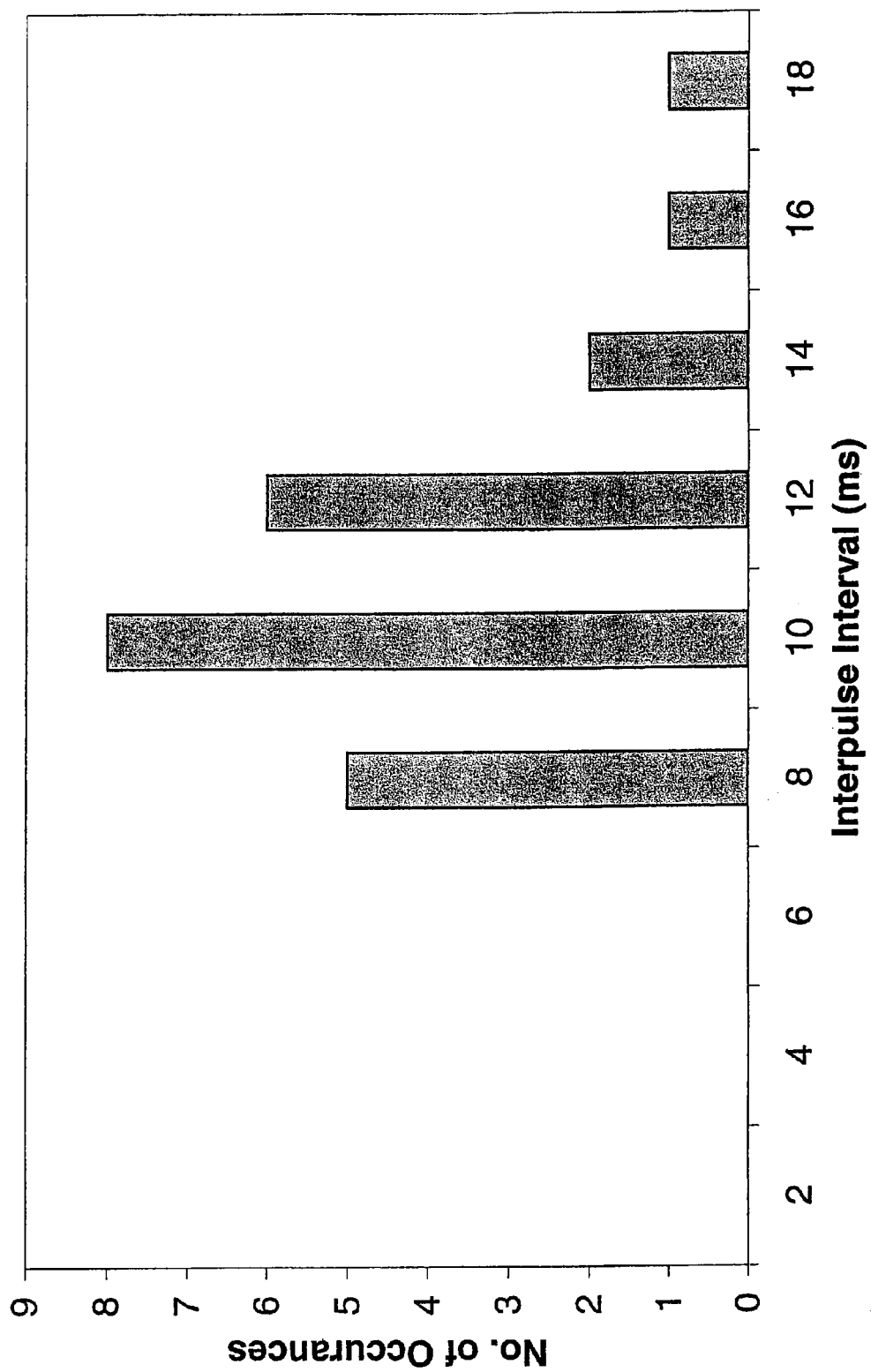
FIG. 3B is a graph illustrating an occurrence distribution that may correspond to a stimulation signal parameter according to an embodiment of the invention.

FIG. 3B is a graph illustrating an exemplary occurrence distribution that may correspond to a stimulation signal parameter according to an embodiment of the invention. An occurrence distribution may specify or indicate an occurrence frequency for one or more parameter values, possibly relative to corresponding parameter value ranges. Thus, for a stimulation parameter such as an interpulse interval, the occurrence distribution of FIG. 3B may specify a relative number of instances that particular interpulse intervals may occur within a given time interval or domain (e.g., approximately 0.25 seconds, 1 second, 15 minutes, 1 hour, or another time interval).

As indicated in FIG. 3B, within a time interval under consideration (e.g., 250 milliseconds), an interpulse interval of 8 milliseconds may occur 5 times; an interpulse interval of 10 milliseconds may occur 8 times; an interpulse interval of 12 milliseconds may occur 6 times; an interpulse interval of 14 milliseconds may occur 2 times; and interpulse intervals of 16 millliseconds and 18 milliseconds may each occur once. While the occurrence distribution shown in FIG. 3B is approximately binomial, the use of a particular type of occurrence distribution (e.g., a Poisson, geometric, hypergeometric, or other type of distribution) may depend upon embodiment details and/or the nature of a patient's neurologic dysfunction.

As previously indicated, the pulse generating unit 110b may generate stimulation signals exhibiting a set of random parameter characteristics or values at one or more times. Herein, random parameter values may correspond to signals that are random, pseudo-random, quasi-random, random-like, or partially random with respect to one or more stimulation signal parameters. In various embodiments, random parameter values may be magnitude limited or bounded, and/or weighted relative to an occurrence function or probability distribution. In one embodiment, the generation of random parameter values in accordance with an occurrence distribution may result in a known or approximately known number of instances that particular parameter values occur within any given time interval under consideration, but a quasi-random ordering of parameter values when one time interval is considered with respect to another time interval.

In certain embodiments, the pulse generating unit 110b may generate stimulation signals exhibiting a set of quasi-periodic or aperiodic parameter characteristics or values at one or more times. Herein, aperiodic parameter values may correspond to signals that are aperiodic, nonperiodic, essentially aperiodic, approximately aperiodic, aperiodic-like, or partially aperiodic relative to one or more stimulation signal parameters.

In one embodiment, a pulse generating unit 110b may be configured to output aperiodic stimulation signals based upon an iterative function, for example, a Mandelbrot or Julia set where an iterated value x at a time t may be determined by operating upon one or more parameter values corresponding to previous times. In one embodiment, an iterative function may have a form such as $x_t = F(x_{t-k}) + c$. Such an equation may exhibit periodic, self-similar, or chaotic behavior depending upon an initial or seed value of $x_0$ (that is, $x_t$ at a time defined as "0") and the value of the constant c. In an example embodiment, a series of aperiodic parameter values may be generated in accordance with the following Equation:

$$x_t = x^2_{t-1} - 1.90 \qquad [1]$$

where $x_0$ may correspond, for example, to a value between 0 and 1.90. In one embodiment, each successive value of $x_t$ may correspond to a stimulation parameter value in accordance with a mapping function and/or a relationship between established, limited, approximated, or estimated maximum and minimum values of $x_t$ and a desired stimulation parameter value range.

Figure 4:
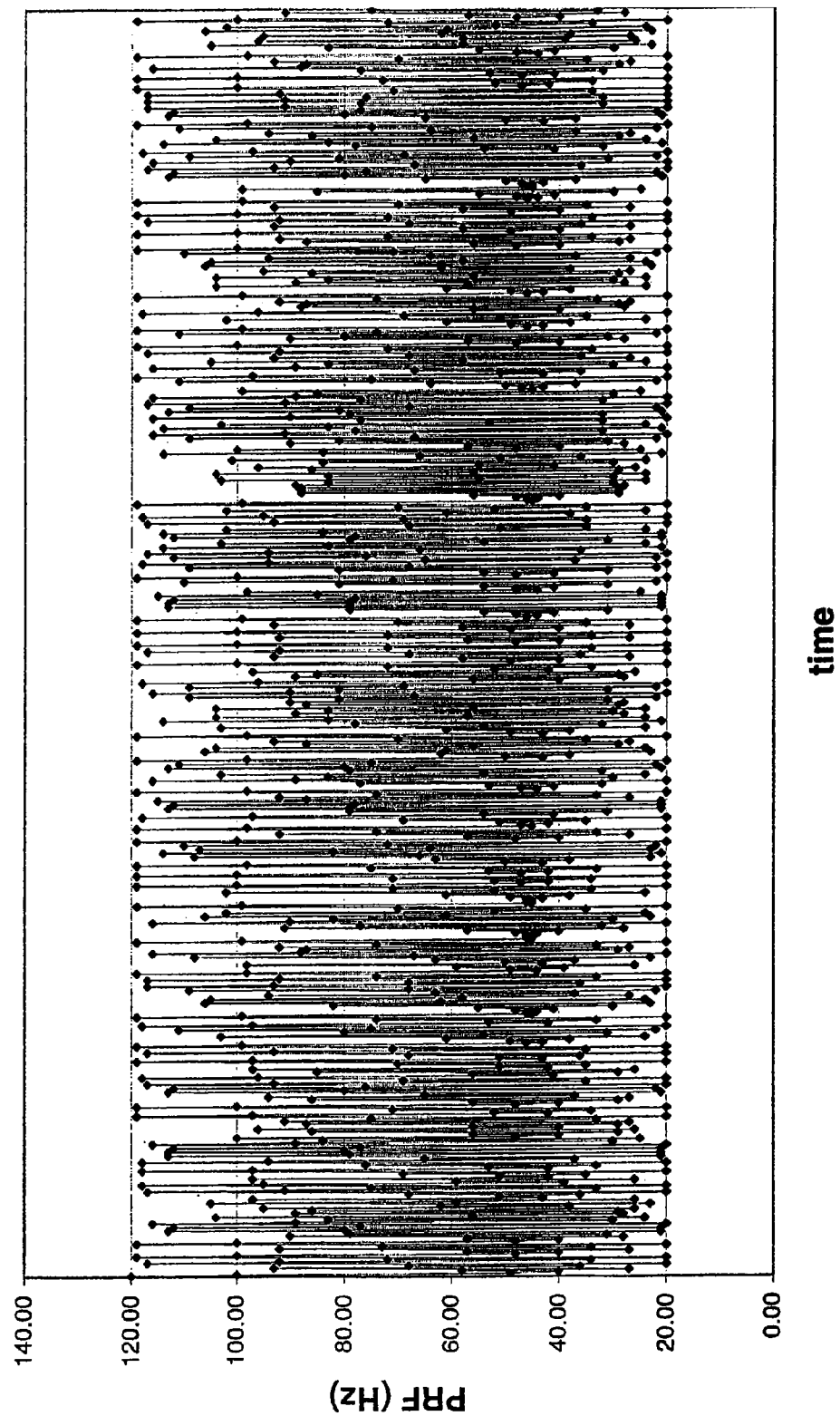
FIG. 4 is a graph illustrating a set of pulse repetition frequency values versus time generated based upon an iterative function in accordance with an embodiment of the invention.

FIG. 4 is a graph illustrating a representative set of pulse repetition frequency values versus time generated based upon Equation 1 using $x_0$ equal to 1.9, where $x_t$ values falling between −1.90 and 1.71 are mapped to pulse repetition frequencies between 20 and 120 Hertz. Certain embodiments may additionally or alternatively employ one or more other types of mappings to the same and/or different stimulation parameters. Those skilled in the art will understand that parameter value discretization in accordance with any given mapping may depend upon the nature of a patient's neurologic dysfunction and/or embodiment details (e.g., pulse generator capabilities).

An iterative function capable of exhibiting aperiodic behavior may facilitate the repeatable delivery of aperiodic stimulation signal sequences to one or more target neural populations without storing entire sequences of individual stimulation signal parameter values across time. An iterative function may facilitate the repeatable delivery of aperiodic stimulation signal sequences or subsequences based upon a minimal or near-minimal amount of stored information corresponding to a minimal or near-minimal number of previously applied parameter values, eliminating undesired or unnecessary parameter value storage. Relative to the representative example above, a given aperiodic stimulation signal sequence or subsequence may be reapplied to a target neural population based upon a seed or parameter value and a constant rather than an entire sequence of individually applied parameter values stored in memory. Similarly, continuation, resumption, or reapplication of an aperiodic stimulation signal sequence or subsequence may be based upon the retrieval of one or more stored stimulation signal parameter values and possibly an associated set of constants that correspond to a prior point in time (e.g., an interruption or termination time).

Different aperiodic pulse sequences may be generated using different values of $x_0$ and/or c. Depending upon embodiment details, successive $x_0$ and/or c values may be selected (e.g., from possible values within a prestored list) or generated in a predetermined, pseudo-random, or aperiodic manner, possibly in accordance with allowable value ranges and/or a probability distribution.

An aperiodic function may additionally or alternatively exhibit another form. In one embodiment, a stimulation parameter value may be generated based upon a set of partial sums corresponding to a type of Weierstrass function that may be defined, for example, in accordance with the following Equation:

$$x(t) = \sum_{n=0}^{q} a^n * \cos(b^n * t) \qquad [2]$$

where 0<a<1, b>1, ab≥1, and q may equal, for example, 10.

Particular neural populations may communicate at one or more times in a manner that corresponds to metastable attractor dynamics. In one embodiment, a set of stimulation parameter values may be generated based upon one or more attractors, for example, a Lorenz, Duffing, or Rossler attractor, which may be capable of exhibiting mathematically metastable, quasi-chaotic, or chaotic behavior. For example, the behavior of a Lorenz-type attractor may be approximated using the following set of Equations:

$$x_1(t+\Delta t) = x_1(t) - a*x_1(t)*\Delta t + a*x_2(t)*\Delta t \qquad [3a]$$

$$x_2(t+\Delta t) = x_2(t) + b*x_1(t)*\Delta t - x_2(t)*\Delta t - x_1(t)*x_3(t)*\Delta t \qquad [3b]$$

$$x_3(t+\Delta t) = x_3(t) + x_1(t)*x_2(t)*\Delta t - c*x_3(t)*\Delta t \qquad [3c]$$

where exemplary default values for a, b, and c may be 5.00, 15.00, and 1.00, respectively, and exemplary default values for $x_1(0)$, $x_2(0)$, and $x_3(0)$ may be 1.00, 0.50, and 2.00. Other exemplary default values for a, b, and c may be 10.00, 28.00, and 2.67, respectively. An exemplary default value for $\Delta t$ may be 20 milliseconds. As used herein, the term "exemplary" is taken to mean "representative" or "sample" or "example of" or "illustrative," as opposed to "ideal" or "archetypal."

Figure 5A:
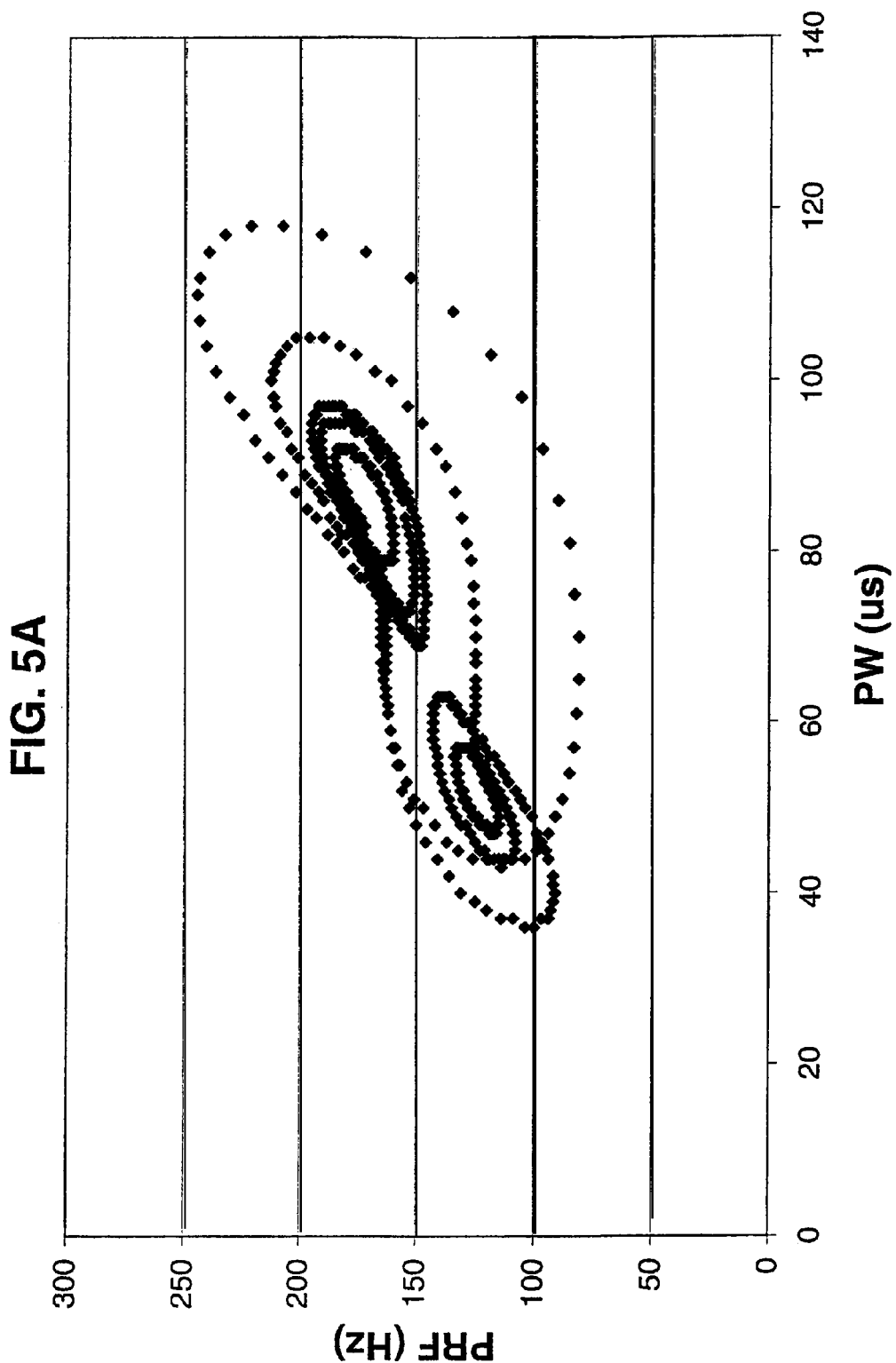
FIG. 5A is a scatter plot illustrating a mapping of equation values corresponding to a Lorenz type attractor to pulse particular repetition frequencies and pulse widths according to an embodiment of the invention.

Values of $x_1(t)$, $x_2(t)$, and/or $x_3(t)$ may be mapped to particular parameter values. FIG. 5A is an exemplary scatter plot corresponding to Equations 3a and 3b, where $x_1(t)$ is mapped to pulse particular repetition frequencies between approximately 20 and 120 Hertz, and $x_2(t)$ is mapped to particular pulse widths between approximately 50 and 150 microseconds using default values of a, b, and c of 5.00, 15.00, and 1.00, respectively. Such a mapping may specify, for example, pulse repetition frequency/pulse width value pairs for stimulation signals successively output by an IPG 100 across one or more time periods. The types of mappings described above may apply to other or additional stimulation signal parameters.

Figure 5B:
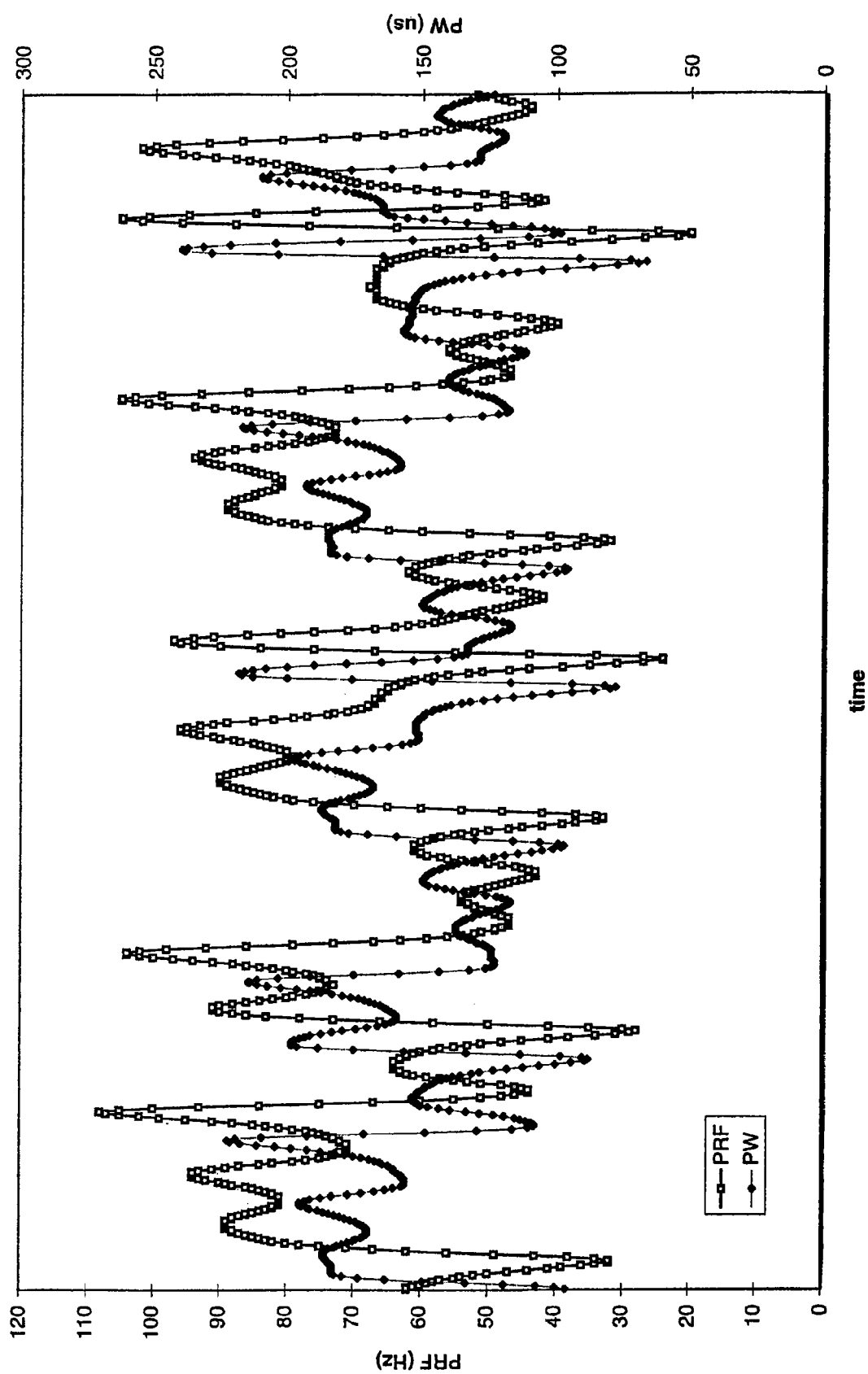
FIG. 5B is a graph illustrating a mapping of equation values corresponding to a Lorenz type attractor to pulse particular repetition frequencies and pulse widths according to another embodiment of the invention.

In one embodiment, mappings such as those described above may occur in accordance with one or more temporal offsets. FIG. 5B is an exemplary graph corresponding to Equations 3a and 3b, where $x_1(t)$ is mapped to pulse repetition frequencies between approximately 20 and 120 Hertz, and $x_2(t)$ is mapped to pulse widths between approximately 50 and 150 microseconds using default values of a, b, and c of 10.00, 28.00, and 2.67, respectively. At any given stimulation signal application time along the x axis of FIG. 5B, a temporal offset of $15*\Delta t$ exists relative to an $x_1(t)$ mapping to a pulse repetition frequency value and an $x_2(t)$ mapping to a pulse width. In such an embodiment, the pulse generating unit 110b may save previously generated values of $x_1(t)$, $x_2(t)$, and/or $x_3(t)$ to facilitate a temporally offset stimulation signal parameter mapping.

Certain embodiments of the invention may generate or output multiple stimulation parameter values based upon particular aperiodic, random, and/or other functions and/or operations in a simultaneous, generally simultaneous, sequential, or intermittent manner. For example, a peak amplitude may be mapped to values between 2.0-8.0 mA in accordance with an aperiodic function; a first phase pulse width may be mapped to values between 50-250 microseconds in an accordance with an aperiodic function or a pseudorandom operation; and/or a pulse repetition frequency may be generated based upon an aperiodic, random, sinusoidal, or other function to have values between 1-20 Hertz.

To aid ease of understanding, square waveforms and/or sinusoidal waveforms are employed for purpose of example in particular portions of the description below. However, various embodiments of the present invention may employ, generate, apply, or deliver stimulation signals exhibiting essentially any type of signal or waveform characteristic at one or more times (e.g., a biphasic waveform, a triangular waveform, and/or other types of waveforms) without departing from the scope of the invention.

Referring again to FIG. 2A, in certain embodiments, the switching unit 110c comprises a switch matrix and/or a set of signal routing or switching elements that facilitate the application, delivery, and/or routing of stimulation signals to one or more sets of electrode assemblies, electrical contacts, and/or signal transfer devices at any given time. In one embodiment, the switching unit 110c may facilitate the electrical activation of particular electrode assemblies, contacts, and/or signal transfer devices, possibly while other such elements remain electrically inactive or electrically float.

The switching unit 110c may additionally or alternatively facilitate the simultaneous or nearly simultaneous activation of different sets of electrode assemblies, contacts, and/or signal transfer devices in accordance with different stimulation parameter sets, possibly while one or more sets of electrode assemblies, contacts, and/or signal transfer devices remain electrically inactive. For example, the switching unit 110c may route a first set of stimulation signals characterized by a peak current amplitude of 3 mA to a first set of electrical contacts 160 carried by an electrode assembly 150, while routing a second set of stimulation signals characterized by a peak current amplitude of 6 mA to a second set of electrical contacts carried by the same or a different electrode assembly 150. As another example, the switching unit 110c may route a set of unipolar stimulation signals characterized by a peak amplitude of 4.5 mA and an aperiodic pulse repetition frequency to a first set of electrode assemblies, while routing a set of bipolar stimulation signals characterized by a peak amplitude of 7.5 mA and a 50 Hertz pulse repetition frequency to a second set of electrode assemblies. Depending upon embodiment details, such selective and/or simultaneous electrical activation may be facilitated with 1) a pulse generating unit 110b configured to simultaneously generate and/or output different sets or versions of stimulation signals; 2) a dual IPG system; and/or 3) an IPG 100 that includes more than one pulse generating unit 110b.

Figure 2B:
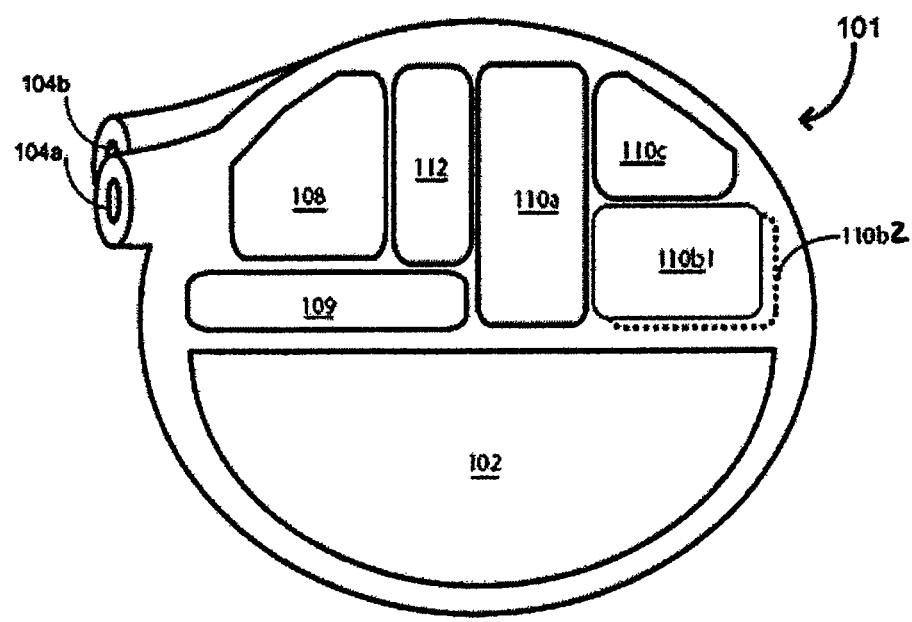
FIG. 2B is an internal block diagram of a stimulation signal generator or an IPG according to another embodiment of the invention.

FIG. 2B is an internal block diagram of a stimulation signal generator or IPG 101 according to another embodiment of the invention. Relative to FIG. 2A, like reference numbers may indicate like or analogous elements. In one embodiment, the IPG 101 comprises multiple pulse generating units 110b1, 110b2 and multiple outputs 104a, 104b. An IPG 101 of the type shown in FIG. 2B may be coupled to two or more electrode assemblies 150 to facilitate the stimulation of different target neural populations in one or more manners, which may depend upon the nature or extent of a patient's neurologic dysfunction and/or embodiment details. The different target neural populations may reside in a variety of anatomical locations. For example, a first and a second target neural population may reside a) in the same or different brain hemispheres; b) in the brain and in the spinal cord; c) at a central nervous system location and at a peripheral nervous system location; or d) at different peripheral nervous system locations. An IPG 101 having multiple pulse generating units 110b1, 110b2 may stimulate different neural populations simultaneously or separately, in an independent or correlated manner. One or both pulse generating units 110b1, 110b2 may generate stimulation signals in various manners described herein to facilitate reduced power consumption and/or improved or maintained neural stimulation efficacy.

Figure 6:
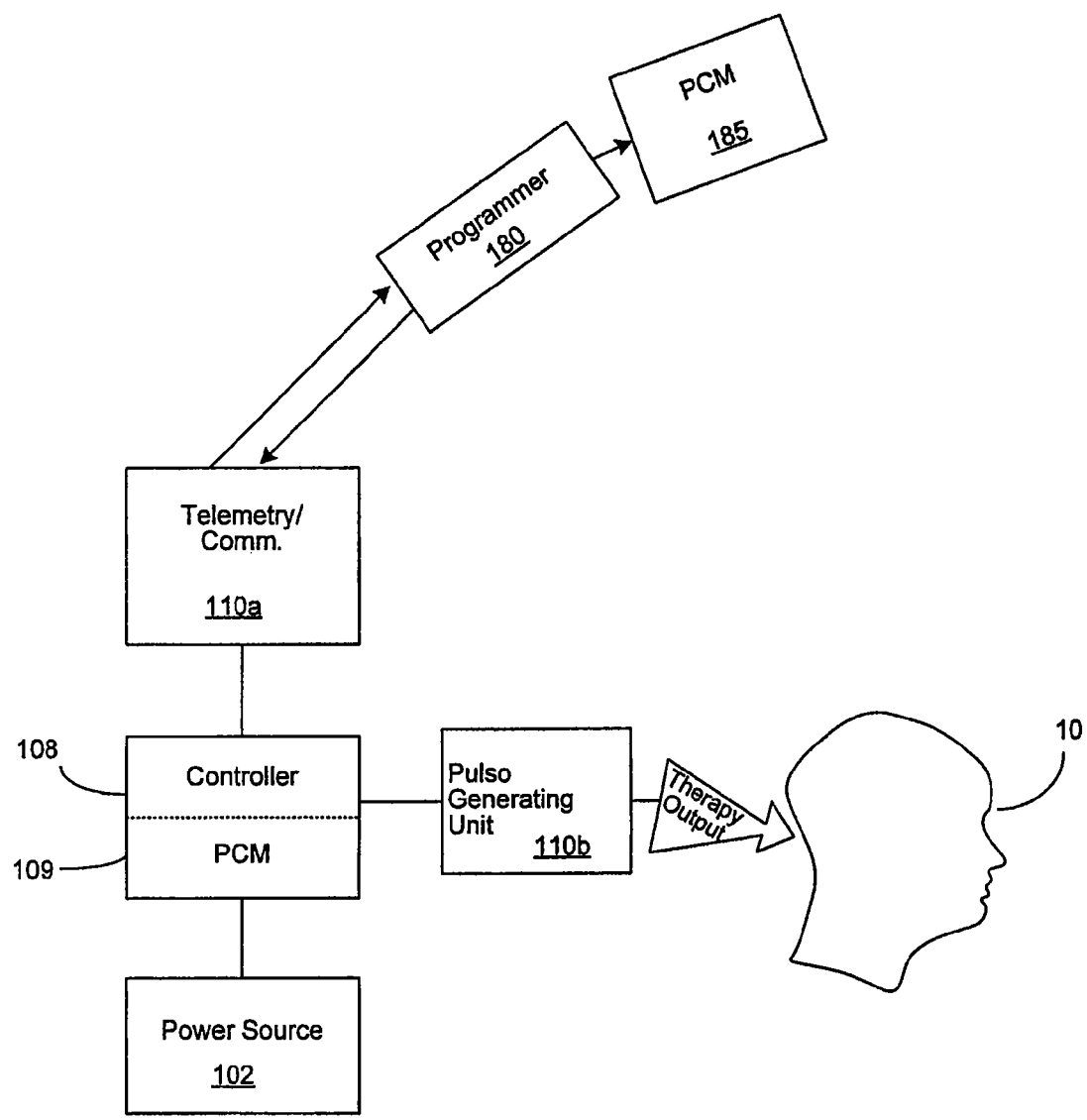
FIG. 6 is a block diagram illustrating particular communication modes that may be supported by a neural stimulation system according to an embodiment of the invention.

FIG. 6 is a block diagram illustrating particular communication modes that may be supported by a neural stimulation system 1000 according to an embodiment of the invention. In one embodiment, the telemetry/communication unit 110a may provide two-way communication for receiving signals from and transmitting signals to an external programmer 180. The telemetry/communication unit 110a may include a wire-based and/or wireless telemetry interface that employs magnetic, radio frequency (RF), optical, and/or other signaling techniques to communicate with the programmer 180. Passwords, handshakes, and parity checks can be employed for signal integrity and/or security purposes. The telemetry/communication unit 110a may additionally or alternatively include one or more wire-based and/or wireless interfaces that facilitate communication with another device such as a patient monitoring unit 200 or a computer (not shown).

In one embodiment, the programmer 180 may comprise a portable electronic device, such as but not limited to a personal digital assistant (PDA) or other type of computing device configured as an interface for communicating with the IPG 100. Such communication may involve the transfer or exchange of control signals, commands, configuration data, instructions, timing or time-base reference information, and/or other information by way of the communication unit 110a. In certain embodiments, the programmer 180 may additionally comprise a programming wand that facilitates telemetric communication with the IPG 100, in a manner understood by those skilled in the art.

The programmer 180 may also comprise and/or be configured for communication with one or more programmable computer media (PCM) 185. In various embodiments, a PCM 185 may comprise a memory and/or one or more other types of data storage devices. The PCM 185 may store stimulation signal definition information and/or treatment program information. In certain embodiments, the PCM 185 comprises a database that may include patient data, statistical information, and/or one or more types of treatment program information for one or more patients. This database may include stimulation waveform information corresponding to stimulation signal frequencies, durations, amplitudes, locations, and the like, and possibly measurement or monitoring results generated by a patient monitoring unit 200.

The programmer 180 may be operated by a physician, clinician, or therapist to communicate a set of neural stimulation parameters and/or associated information to the IPG 100. Programming capabilities may include the ability to specify and/or modify various waveform parameters and/or functions corresponding to a pulse generating unit 110b. Programming capabilities may further include an ability to perform diagnostics and/or store and/or retrieve telemetered data. It is to be appreciated by those of ordinary skill in the art that the IPG 100 can be programmed using a personal or other type of computer (not shown) employing appropriate software and a programming wand (not shown).

Adjusting or Affecting Power Consumption and/or Efficacy

In accordance with various embodiments of the present invention, power consumption may be improved or decreased and/or neural stimulation efficacy increased, preserved, or generally maintained by controlling, adjusting, modifying, and/or modulating a manner in which neural stimulation is applied or delivered to a patient. As indicated above, particular systems and/or methods described herein may apply or deliver neural stimulation at one or more subthreshold and/or suprathreshold amplitudes, levels, or intensities at one or more times. A subthreshold stimulation amplitude may correspond to a particular fraction or percentage of a lowest or near lowest test stimulation signal amplitude at which a patient exhibits a particular type of response. The response may correspond to an externally measurable or observable reaction such as a movement; an effect upon an internally measurable or observable signal such as an EEG signal; a patient-reported sensation; and/or another type of response.

Various systems and/or methods described herein may apply or deliver bipolar and/or unipolar, monopolar, or isopolar stimulation signals. Unipolar stimulation signals exhibit an identical polarity at any given time, and electrical continuity may be provided by a current return path or return electrode that is remotely positioned relative to a target neural population. Unipolar stimulation may potentially reduce power consumption, provide enhanced efficacy or efficiency stimulation, and/or mitigate collateral effects. Depending upon embodiment details, certain systems and/or methods may apply or deliver unipolar stimulation at one time and bipolar stimulation at another time. Some embodiments may provide unipolar stimulation one or more manners that are identical, essentially identical, or analogous to those described in U.S. application Ser. No. 10/910,775, previously incorporated herein by reference.

In certain embodiments, a neural stimulation system 1000 may be initially configured to provide or deliver optimum, near-optimum, or expected best stimulation to a patient relative to one or more patient states, symptoms, and/or functional deficits under consideration at a particular time. That is, a neural stimulation system 1000 may be configured to provide stimulation in a manner determined or expected to be most efficacious, most therapeutic, efficacious, or therapeutic. Such stimulation may correspond to an initial stimulation configuration.

A neural stimulation system 1000 may be subsequently configured or adjusted to provide or deliver effective, generally effective, adequate, acceptable, and/or sufficient stimulation at a reduced power level to one or more target neural populations relative to a set of patient states, conditions, symptoms, and/or functional deficits under consideration. A neural stimulation system 1000 may additionally or alternatively be configured to provide changing, varying, or neurologically novel or generally novel stimulation signals to one or more target neural populations in order to maintain or improve neural stimulation efficacy. Stimulation provided in the aforementioned manners may address, treat, and/or relieve one or more patient conditions, symptoms, and/or functional deficits in a manner that is similar or identical to or possibly better than stimulation provided in accordance with an initial stimulation configuration, and may correspond to an adjusted stimulation configuration. An adjusted stimulation configuration provided in accordance with various embodiments of the invention may extend battery life and/or a power source recharging interval, and/or improve, sustain, or generally maintain neural stimulation efficacy. To facilitate prolonged battery life or extend power source recharging intervals, various embodiments may apply neural stimulation in accordance with an adjusted stimulation configuration when a battery and/or other power source is essentially fully-charged, or prior to the occurrence of noticeable, moderate, appreciable, or significant power source depletion.

Depending upon embodiment details, power consumption and/or efficacy may affected by adjusting or varying one or more parameters associated with a treatment program. In several embodiments, such parameters may correspond to one or more neural stimulation procedures. A neural stimulation procedure may define, specify, and/or indicate one or more sets of stimulation period parameters, stimulation waveform parameters, stimulation modulation parameters, and/or stimulation location parameters. Stimulation period parameters may specify or indicate one or more active periods during which stimulation signals may be applied to a patient, and/or one or more quiescent periods during which neural stimulation may be avoided. Stimulation period parameters may correspond to subseconds-based, seconds-based, hours-based, and/or other time domains or scales.

Stimulation waveform parameters may define, describe, or characterize a stimulation signal in a manner identical, essentially identical, analogous, or generally analogous to that described above with respect to FIG. 3. In general, stimulation waveform parameters may define or describe a stimulation signal on a subseconds-based time domain, and/or possibly a seconds-based time domain.

Stimulation modulation parameters may define, specify, or indicate one or more manners of modulating or transforming neural stimulation signals. Depending upon embodiment details, stimulation modulation parameters may correspond to one or more mathematical operations or functions applied to particular stimulation signal parameters, possibly relative to one or more time scales. Stimulation modulation parameters may typically correspond to subseconds-based, seconds-based, hours-based, and/or other time domains.

Finally, stimulation location parameters may define or specify particular sets of signal transfer devices, electrode structures, electrode assemblies, and/or conductive elements to which stimulation signals may be applied or directed at one or more times.

Duty Cycle Modification

In various embodiments, power consumption may be decreased and/or neural stimulation efficacy maintained or increased by controlling, adjusting, or modifying a neural stimulation duty cycle. Duty cycle may be defined as a percentage of time a device is "ON," consuming power, or depleting a power source during or relative to a time domain under consideration. Various types of time domains may be defined, including an hours-based time domain, a seconds-based time domain, and a subseconds-based time domain as indicated above. Thus, in one embodiment, duty cycle may be defined as Duty Cycle=(time on)/(time on+time off)

relative to a given type of time domain.

In certain embodiments, instead of enabling, allowing, or providing for stimulation pulse or pulse train generation or delivery during an entire time domain in a continuous or uninterrupted manner, a neural stimulator such as an IPG 100 or particular elements therein (e.g., a pulse generator 108) may be selectively turned off or disabled during one or more portions or segments of one or more time domains under consideration. This reduces a neural stimulation duty cycle, thereby conserving power. In further aspects of these embodiments, a given series of electromagnetic stimulation signals may be interrupted and a stimulation parameter selected/adjusted to conserve power. The interruption and/or parameter selection/adjustment can occur well before the power provided to the pulse generator (e.g., by a battery) is significantly depleted, to provide a significant decrease in power consumption.

Figure 7A:
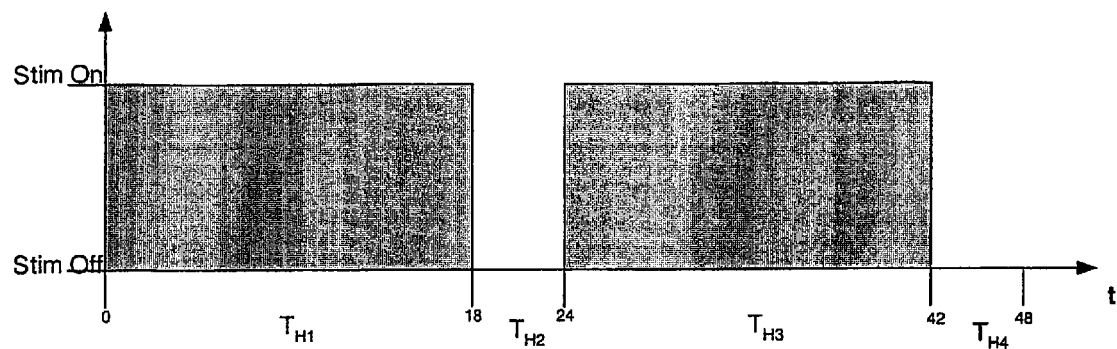
FIG. 7A is a graph illustrating an interruption, disabling, or cessation of stimulation signal generation, delivery, or application relative to an hours-based time domain according to an embodiment of the invention.

FIG. 7A is a graph illustrating an exemplary interruption, disabling, or cessation of stimulation signal generation relative to an hours-based time domain to effectuate a reduction in an hours-based duty cycle according to an embodiment of the invention. In accordance with FIG. 7A, a neural stimulator or particular elements therein may be configured in an "ON" state or enabled during a first hours-based time period $T_{H1}$, and configured in an "OFF" state or disabled during a second hours-based time period $T_{H2}$. The combined duration of $T_{H1}$ and $T_{H2}$ form an hours-based time domain $T_H$ under consideration. In an exemplary embodiment, $T_{H1}$ may be 18 hours, and $T_{H2}$ may be 6 hours. $T_{H1}$ may have a significant likelihood of corresponding to hours during which a patient is expected to be awake, and $T_{H2}$ may have a significant likelihood of corresponding to hours during which a patient is expected to be asleep. Such an operational scheme may be useful for patients suffering from movement disorders such as essential tremor or Parkinson's Disease because patient symptoms may be less severe during slumber.

In the foregoing example, a six-hour off time per day would result in

Duty Cycle$_H$=18/(18+6)=0.75 or a 75% hours-based duty cycle. In other words, a six-hour off time results in a 25% hours-based duty cycle reduction, thereby conserving power.

$T_{H2}$ may be a portion or fraction of $T_H$ that meets a reduced duty cycle target in view of an acceptable level of clinical efficacy. In general, $T_H$ may be comprised of multiple "ON" times and one or more "OFF" times (e.g., there may be a $T_{H3}$ that corresponds to an "ON" time, a $T_{H4}$ that corresponds to an "OFF" time, etc. . . . ). The duration of one or more "ON" and/or "OFF" times may be determined, established, programmably specified, and/or adjusted in a periodic, aperiodic, or random manner, possibly accordance with a target duty cycle relative to a given degree of clinical efficacy. In FIG. 7A, an hours-based time domain corresponds to a 24-hour period. One or more other types of hours-based time domains may be defined depending upon embodiment details, actual or expected patient state, and/or clinicial conditions.

Figure 7B:
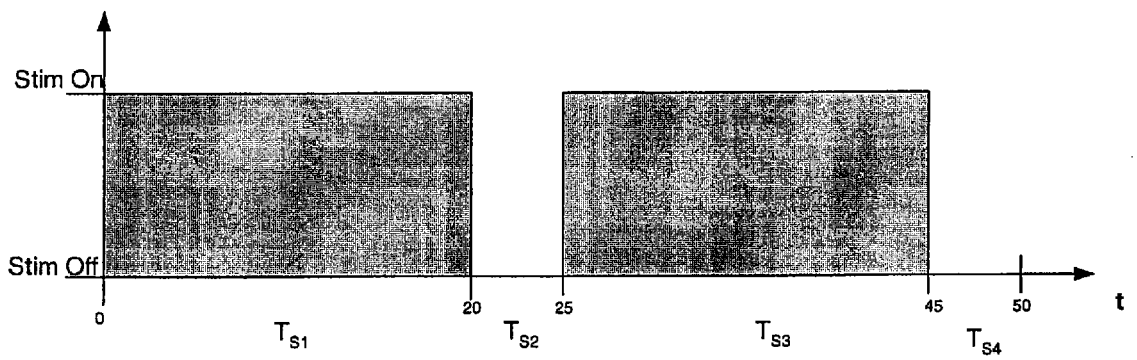
FIG. 7B is a graph illustrating an interruption, disabling, or cessation of stimulation signal generation in a seconds-based time domain according to an embodiment of the invention.

FIG. 7B is a graph illustrating an exemplary interruption, disabling, or cessation of stimulation signal generation in a seconds-based time domain to effectuate a reduction in a seconds-based duty cycle according to an embodiment of the invention. In accordance with FIG. 7B, a neural stimulator or particular elements therein may be configured in an "ON" state or enabled during a first seconds-based time period $T_{S1}$, and configured in an "OFF" state or disabled during a second seconds-based time period $T_{S2}$. The combined duration of $T_{S1}$ and $T_{S2}$ form a seconds-based time domain $T_S$ under consideration. In an exemplary embodiment, $T_{S1}$ may be 20 seconds, and $T_{S2}$ may be 5 seconds. Thus, if neural stimulation comprises the periodic or quasi-periodic application of stimulation signals or a pulse train for 20 seconds followed by a quiescent interval of 5 seconds, a seconds-based duty cycle may be defined as Duty Cycle$_S$=20/(20+5)=0.80 giving 80% seconds-based duty cycle, which provides a 20% seconds-based duty cycle reduction.

$T_{S2}$ may be a portion or fraction of $T_S$ that meets a reduced duty cycle target in view of an acceptable level of clinical efficacy. In general, $T_S$ may be comprised of multiple "ON" times and one or more "OFF" times (e.g., there may be a $T_{S3}$ that corresponds to an "ON" time, a $T_{S4}$ that corresponds to an "OFF" time, etc. . . . ). The duration of one or more "OFF" times may be determined, established, programmably specified, and/or adjusted in accordance with a target duty cycle relative to a given degree of clinical efficacy. In certain embodiments, $T_{S2}$ and/or one or more other "OFF" times may be determined in a random, quasi-random, or aperiodic manner, possibly with respect to a minimum duration $T_{S1}$ or total "ON" time within $T_S$.

Figure 7C:
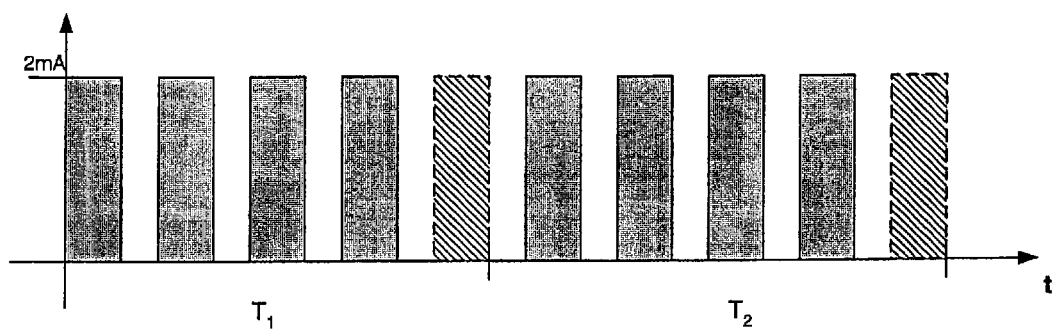
FIG. 7C is a graph illustrating an interruption, disabling, or cessation of stimulation signal generation in a subseconds-based time domain according to an embodiment of the invention.

FIG. 7C is a graph illustrating an exemplary interruption, disabling, or cessation of stimulation signal generation in a subseconds-based time domain to effectuate a reduction in a subseconds-based or seconds-based duty cycle according to an embodiment of the invention. In certain embodiments, a subseconds-based duty cycle may be reduced by omitting or skipping one or more pulses within a pulse train (indicated in FIG. 7C by cross hatching) during a subseconds-based or seconds-based time interval, possibly on a periodic, aperiodic, or quasi-random basis. In the embodiment shown in FIG. 7C, four pulses are delivered and a fifth pulse is skipped on a periodic basis. That is, a number of delivered pulses $P_D$ equals four, and a number of skipped pulses $P_S$ equals one. This results in a subseconds-based duty cycle of Duty Cycle$_{SS}$=4/(4+1)=0.80 or an 80% subseconds-based duty cycle, thereby providing a 20% subseconds-based duty cycle reduction. Depending upon embodiment details, a number of pulses skipped within or relative to a given subseconds-based or seconds-based time interval may be greater than one, possibly based upon a target subseconds-based duty cycle in view of an acceptable degree of clinical efficacy.

In certain embodiments, a neural stimulation duty cycle may be further reduced through duty cycle reductions in two or more time domains. An overall or effective duty cycle may be given by a product of individual duty cycles in the time domains under consideration. For example, combining the exemplary duty cycle reductions described above with respect to FIGS. 7A-7C gives rise to an effective duty cycle of $$\text{Duty Cycle}_{EFF} = (DC_H)(DC_S)(DC_{SS}) = (0.75)(0.80)(0.80) = 0.48$$

or a 48% effective duty cycle, which provides a 52% overall duty cycle reduction. Such a duty cycle reduction may significantly prolong battery life. Depending upon embodiment details, duty cycle reductions associated with essentially any plurality of time domains (e.g., a seconds-based time domain and a subseconds-based time domain; an hours-based time domain and a seconds-based time domain; or an hours-based time-domain and a subseconds-based time domain) may be combined in a manner identical or analogous to that described above Various other types of duty cycle variation or modification may be relevant depending upon embodiment details, the nature of a patient's neurologic dysfunction, and/or short-term or long-term patient response to neural stimulation. For a patient experiencing a movement disorder such as essential tremor, an amount of time a patient continues to experience symptomatic benefit during an OFF time may depend upon a cumulative or aggregate duration of recent ON times. As stimulation is applied over the course of more ON times, at least some symptomatic benefit may persist across a longer OFF time.

As a representative example, stimulation may be initially applied in accordance with a 5 minute ON time and a 2 minute OFF time. At each 30 minute interval after stimulation begins, the OFF time may be increased by 1 minute while the ON time may be maintained at 5 minutes, until reaching an OFF time of 5 minutes. Then, at each 1 hour interval after an ON/OFF duty cycle of 5 minutes/5 minutes is reached, the OFF time may be increased by 1 minute until reaching an OFF time of 10 minutes. One or more of the preceding time intervals may differ in length as a result of patient-specific factors.

In other representative examples, ON times may also be varied instead of or in addition to OFF times. Additionally or alternatively, particular ON and/or OFF times may be adjusted or limited based upon the measurement of a patient-specific parameter such as a tremor frequency (e.g., using accelerometers). Such adjustment may occur manually, or automatically using a closed-loop system.

Modification of Stimulation Frequency Characteristics

In various embodiments, power consumption may be decreased and/or neural stimulation efficacy affected by adjusting or modifying one or more types of stimulation frequency characteristics, possibly relative to one or more time domains under consideration. Depending upon embodiment details, modification of stimulation frequency characteristics may result in or correspond to a duty cycle modification. As a result, particular considerations described above may identically, analogously, or similarly apply to one or more embodiments described hereafter.

In certain embodiments, power consumption may be reduced and/or neural stimulation efficacy affected at one or more times through the application or delivery of stimulation signals characterized in accordance with one or more types of naturally or intrinsically occurring neural signaling patterns. For example, the application or delivery of stimulation signals to a set of target neural populations may be timed or approximately timed based upon one or more known cortical ensemble discharge frequency ranges or bands. Cortical ensemble discharge frequency bands are typically categorized as delta, theta, alpha, beta, and gamma frequency bands. In general, the delta frequency band corresponds to frequencies less than approximately 4 Hz; the theta frequency band corresponds to frequencies between approximately 4 Hz and approximately 8 Hz; the alpha frequency band corresponds to frequencies between approximately 8 Hz and 13 Hz; the beta frequency band corresponds to frequencies between approximately 13 Hz and 30 Hz; and the gamma frequency band corresponds to frequencies greater than approximately 30 Hz. Those skilled in the art will understand that the above frequency band delineations are approximate (e.g., alpha frequencies may be alternately defined as falling between approximately 3.0 or 3.5 Hz and 7.0, 7.5, or possibly even 10.0 Hz).

In various embodiments, stimulation signals that are generated, applied, or delivered in a manner that corresponds to an intrinsic neural signaling behavior may include or comprise a set or series of pulse bursts or pulse packets. An actual, average, or estimated number of pulse bursts or pulse packets generated, applied, or delivered per second may correspond or approximately correspond to a particular type of intrinsic neural signaling behavior, such as a delta, theta, alpha, beta, or gamma frequency.

A number of pulse bursts per second may be defined as an interburst frequency. In several embodiments, pulse bursts are temporally separated by a quiescent interval. In some embodiments, one or more pulse bursts may be temporally separated by nearly or approximately quiescent intervals, during which a set of additional, possibly reduced-amplitude and/or less frequent stimulation signals may be applied in a predetermined, pseudo-random, and/or aperiodic manner.

Depending upon embodiment details, an individual pulse burst or packet may comprise a set of pulses characterized by an actual, average, or estimated intraburst or intrapacket pulse repetition frequency, for example, an intraburst pulse repetition frequency between approximately 50 Hz and 500 Hz. In one embodiment, intraburst pulse repetition frequency may vary with time and/or packet count in a predetermined, quasi-random, or aperiodic manner.

Herein, neural stimulation that comprises a set of pulse bursts applied in a manner that corresponds to one or more types of intrinsic neural signaling behavior is defined as neuro-burst stimulation. Thus, relative to the aforementioned cortical ensemble discharge frequency bands, neuro-burst stimulation provided by various embodiments of the invention may include delta-burst, theta-burst, alpha-burst, beta-burst, and/or gamma-burst stimulation. Depending upon a patient's neurologic profile and/or embodiment details, neuro-burst stimulation may be applied and/or delivered to one or more target neural populations at one or more times on a continuous, quasi-continuous, periodic, quasi-random, or aperiodic basis, possibly in association with other types of stimulation signals.

Neuro-burst stimulation may be generated or applied at one or more amplitudes, levels, or intensities that correspond to subthreshold-level, threshold-level, and/or suprathreshold-level stimulation. Such amplitudes may remain constant, or vary from or within a given burst to another burst. In some embodiments, one or more intraburst stimulation parameters (e.g., intraburst pulse amplitude, intraburst frequency, and/or intraburst first-phase pulse width) may vary across a series of pulse bursts. Such variation may occur in a predetermined, quasi-random, and/or aperiodic (e.g., chaotic) manner.

One or more types of neuro-burst stimulation may facilitate enhanced neural stimulation efficacy and/or reduced power consumption. For example, theta-burst stimulation may facilitate enhanced functional recovery or development in patients experiencing neurologic dysfunction associated with stroke, TBI, learning and/or memory disorders, Alzheimer's disease, and/or other conditions. Theta-burst stimulation may facilitate neurological consolidation of newly or recently acquired functional gains, learned skills, and/or memories, possibly through one or more mechanisms corresponding or related to LTP, depotentiation, LTD, and/or synaptic plasticity. Moreover, theta-burst and/or one or more other types of neuro-burst stimulation may facilitate enhanced symptomatic relief associated with neurologic conditions involving maladaptive neuroplasticity, for example, tinnitus, auditory hallucinations, phantom limb pain or other chronic pain syndromes, and/or other conditions.

Representative manners in which theta-burst stimulation may affect neurologic processes are described in a) "Induction and Reversal of Long-Term Potentiation by Low- and High-Intensity Theta Pattern Stimulation," S. Barr et al., *The Journal of Neuroscience*, July 1995, 15(7): 5402-5410; b) "Reversal of LEP by Theta Frequency Stimulation," John Larson et al., *Brain Research*, 600(1993) 97-102; and c) "Theta-burst Stimulation of the Human Motor Cortex,"Ying-Zu Huang et al., *Neuron*, Vol. 45, 201-206, Jan. 20, 2005, each of which is incorporated herein by reference.

One or more types of neuro-burst stimulation (e.g., gamma-burst stimulation) may facilitate an interruption, disruption, shifting, modulation, desynchronization, and/or other type of alteration (e.g., the establishment of or a change in a neural entrainment pattern) of dysfunctional or undesired neural signaling behavior (e.g., oscillatory behavior and/or one or more types of neural signal coherence associated with a movement disorder). Such neuro-burst stimulation may involve subthreshold-level, near-threshold-level, threshold-level, and/or suprathreshold-level stimulation signals, where individual pulses or pulse packets corresponding to threshshold-level or suprathreshold-level stimulation may be brief, relatively brief, generally infrequent, and/or intermittent relative to subthreshold-level pulses or pulse packets.

Figure 8A:
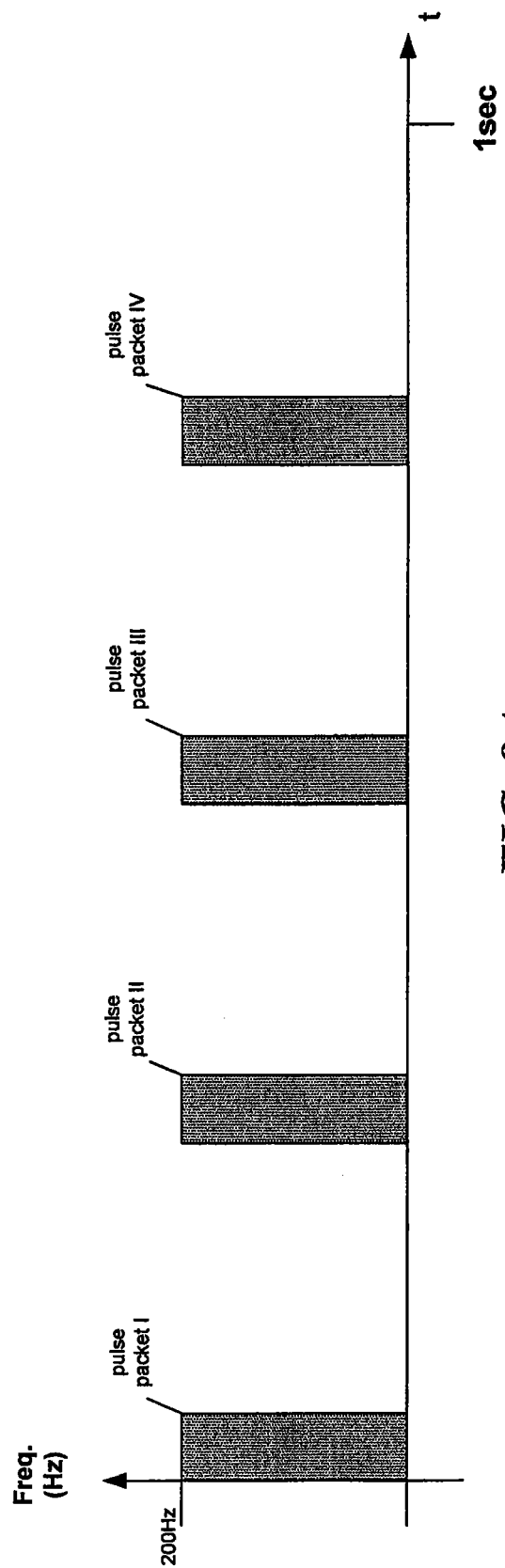
FIG. 8A is a graph illustrating a theta-burst stimulation pattern in accordance with an embodiment of the invention.

FIG. 8A is a graph illustrating an exemplary theta-burst stimulation pattern that may affect power consumption and/or neural stimulation efficacy according to an embodiment of the invention. In one embodiment, a theta-burst stimulation pattern may comprise 4 pulse bursts or packets per second, where each pulse packet comprises ten pulses characterized by an intrapacket pulse repetition frequency of 200 Hertz. Thus, each pulse packet comprises ten 200 Hz pulses, and a temporal reference point corresponding to any given pulse packet is separated from an equivalent reference point corresponding to a subsequent pulse packet by 200 ms.

Figure 8B:
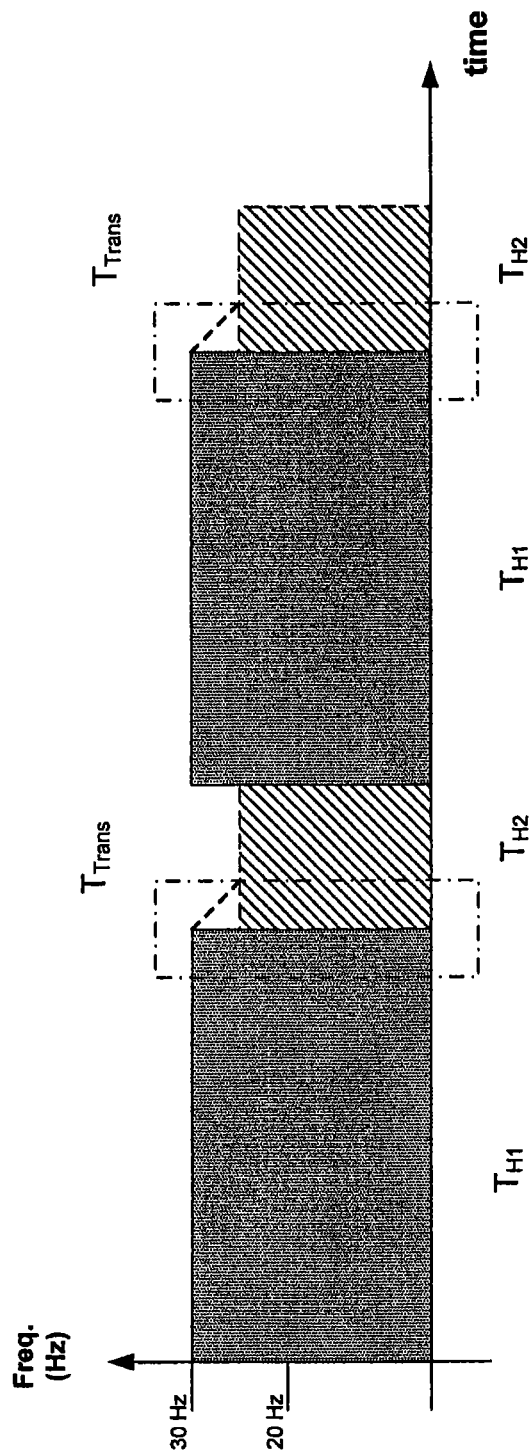
FIG. 8B is a graph illustrating a stimulation frequency modification relative to an hours-based time domain according to an embodiment of the invention.

Additional and/or alternate types of neural stimulation frequency modification may reduce power consumption and/or affect neural stimulation efficacy. FIG. 8B is a graph illustrating an exemplary stimulation frequency modification relative to an hours-based time domain $T_H$ to affect power consumption and/or neural stimulation efficacy according to an embodiment of the invention. In FIG. 8B, neural stimulation characterized by a first set of stimulation frequency characteristics $f_1$ may be applied to a patient during a first hours-based time period $T_{H1}$. Following $T_{H1}$, neural stimulation characterized by a second set of stimulation frequency characteristics $f_2$ may be applied to the patient during a second hours-based time period $T_{H2}$. Certain embodiments may include a transition period $T_{TRANS}$ between $T_{H1}$ and $T_{H2}$ and/or $T_{H2}$ and $T_{H1}$, wherein neural stimulation frequency characteristics are varied in a smooth, gradual, or generally gradual manner between $f_1$ and $f_2$. The transition period may correspond to a transition frequency function or envelope $f_{TRANS}$, which may comprise, for example, a linear or polynomial based change in frequency versus time.

Depending upon embodiment details, the first set of stimulation frequency characteristics $f_1$ may correspond to a stimulation signal frequency, frequency pattern, and/or frequency function that has been determined or is expected to be most effective, effective, or generally effective for treating one or more patient symptoms and/or facilitating one or more neurofunctional and/or patient outcomes. For example, $f_1$ may specify a 30 Hz or other pulse repetition frequency. The second set of stimulation frequency characteristics $f_2$ may correspond to a reduced stimulation signal frequency, frequency pattern, and/or frequency function that may be effective, generally effective, or adequate for treating one or more patient symptoms and/or facilitating particular patient outcomes. For example, $f_2$ may correspond to a 20 Hz or other pulse repetition frequency. In an exemplary embodiment in which $T_{H1}$ equals 18 hours, $f_1$ equals 30 Hz, $T_{H2}$ equals 6 hours, and $f_2$ equals 20 Hz, power consumption during $T_{H2}$ may be reduced by approximately 33% relative to that during $T_{H1}$. In the event that $T_{H2}$ corresponds to hours during which a patient is likely to be asleep or resting, patient symptoms may be less severe, and hence a lower pulse repetition frequency may be appropriate.

In an alternate embodiment, $f_1$ and/or $f_2$ may define, specify, or indicate one or more neuro-burst stimulation patterns. In one exemplary embodiment, $f_1$ may correspond to a 50 Hz pulse repetition frequency during an 18 hour $T_{H1}$ period. During a 6 hour $T_{H2}$ period, $f_2$ may correspond to a theta-burst pattern, for example, 5 pulse packets per second, where each pulse packet comprises five 100 Hz pulses. In such an embodiment, power consumption during $T_{H2}$ may be reduced relative to that during $T_{H1}$ by approximately 50% under equi-amplitude conditions.

An hours-based time domain may comprise other or multiple time periods characterized by modified (e.g., reduced, increased, and/or varying) frequency stimulation. Stimulation frequency characteristics may alternatively or additionally be modified before, during, and/or after one or more time periods corresponding to an adjunctive or synergistic therapy. An adjunctive therapy may comprise, for example, a drug therapy, a neurotrophic and/or growth factor therapy, and/or a behavioral therapy. Depending upon embodiment details, a behavioral therapy that is relevant to one or more types of neural stimulation in accordance with the present invention may comprise a physical therapy activity, a movement and/or balance exercise, a strength training activity, an activity of daily living (ADL), a vision exercise, a reading task, a speech task, a memory or concentration task, a visualization or imagination exercise, an auditory activity, an olfactory activity, a biofeedback activity, and/or another type of behavior, task, or activity that may be relevant to a patient's functional state, development, and/or recovery.

In one embodiment, one or more types of neuro-burst stimulation may be applied to a patient before, during, and/or after a behavioral therapy session. In an exemplary embodiment, during a behavioral therapy period $T_{BT}$ that may range between approximately one-half hour and several (e.g., four) hours, one or more periods or intervals characterized by theta-burst and/or other neuro-burst stimulation that is identical, essentially identical, or similar to or different from that described above may be applied to the patient. Outside $T_{BT}$, neural stimulation may be avoided, or applied to the patient in a variety of manners, including one or more manners described herein.

Figure 8C:
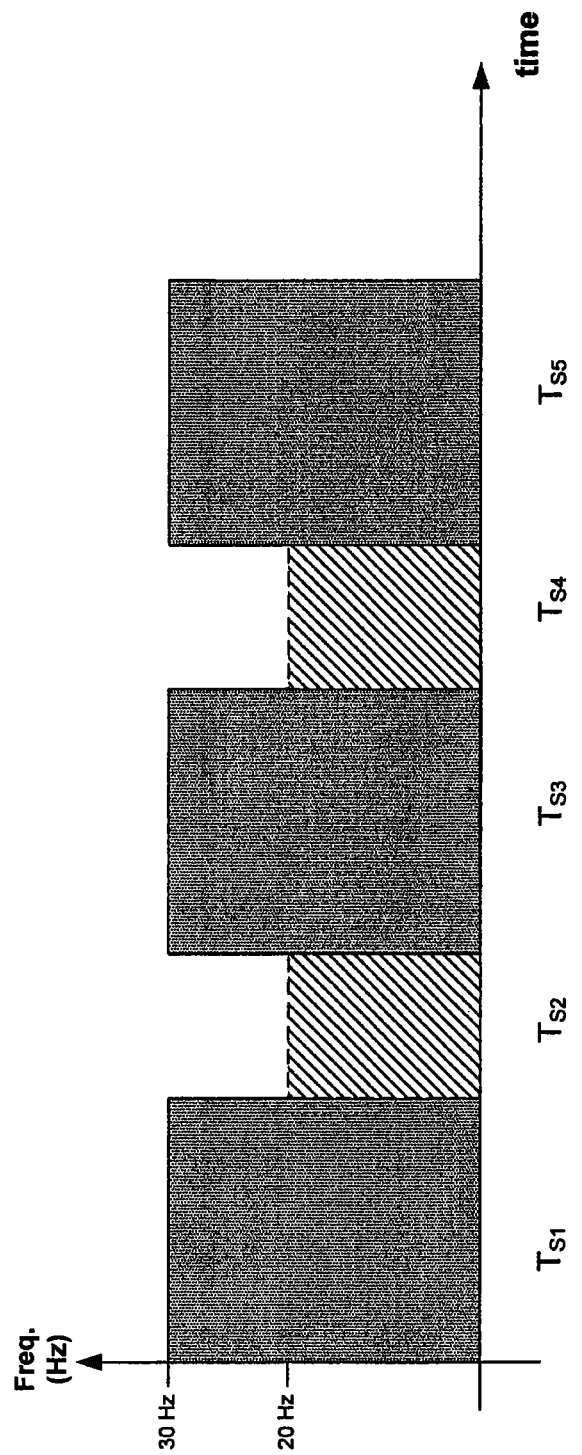
FIG. 8C is a graph illustrating a stimulation frequency modification relative to a seconds-based time domain according to an embodiment of the invention.

In various embodiments, stimulation frequency characteristics may alternatively or additionally be varied, modified, or modulated relative to a seconds-based and/or a subseconds-based time domain. FIG. 8C is a graph illustrating an exemplary stimulation frequency modification relative to a seconds-based time domain $T_S$ to power consumption and/or neural stimulation efficacy according to an embodiment of the invention. In one embodiment, neural stimulation characterized by a first set of stimulation frequency characteristics $f_1$ (e.g., a pulse repetition frequency of 30 Hz) may be applied to a patient during a first seconds-based time period $T_{S1}$ (e.g., 15 seconds). Neural stimulation characterized by a second set of stimulation frequency characteristics $f_2$ (e.g., a pulse repetition frequency of 20 Hz) may be applied to the patient during a second seconds-based time period $T_{S2}$ (e.g., 5 seconds). In such an embodiment, power consumed during $T_{S2}$ may be reduced relative to that during $T_{S1}$ by a factor of approximately 33%, which may reduce overall power consumption by approximately 8.3%.

Depending upon embodiment details, the first set of stimulation frequency characteristics $f_1$ may correspond to a stimulation signal frequency, frequency pattern, and/or frequency function that has been determined or is expected to be most effective or effective for treating one or more patient symptoms and/or facilitating one or more patient outcomes. The second set of stimulation frequency characteristics $f_2$ may correspond to a reduced stimulation signal frequency, frequency pattern, and/or frequency function that may be effective, generally effective, or adequate for treating one or more patient symptoms and/or facilitating particular patient outcomes. In certain embodiments, $f_1$ and/or $f_2$ may correspond to neuro-burst stimulation. From a given seconds-based time domain $T_S$ to another, some embodiments may establish $f_2$ in a variable, quasi-random, or aperiodic manner, possibly relative to a maximum and/or minimum acceptable $f_2$.

In general, the duration of $T_{S2}$ may be established or determined in a manner that meets or approximately meets a power consumption target in view of an acceptable level of clinical efficacy. In certain embodiments, a seconds-based time domain $T_S$ may comprise other or multiple periods characterized by reduced frequency neural stimulation. The total duration of such periods may be determined in a random, quasi-random, or aperiodic manner, possibly with respect to a minimum duration $T_{S1}$ and/or minimum level of clinical efficacy.

In some embodiments, stimulation frequency characteristics may vary in accordance with a time dependent function f(t), for example, a sinusoid. In one embodiment, a maximum frequency $f_{max}$ may correspond to a frequency determined or expected to be most effective or effective frequency for treating one or more patient symptoms. A minimum frequency $f_{min}$ may correspond to a lowest frequency suitable for adequately treating one or more patient symptoms. In general, f(t) may comprise a function bounded by $f_{max}$ and $f_{min}$. Furthermore, f(t) may be characterized by an average or RMS frequency that may be effective, generally effective, or adequate for treating a set of patient symptoms.

Figure 8D:
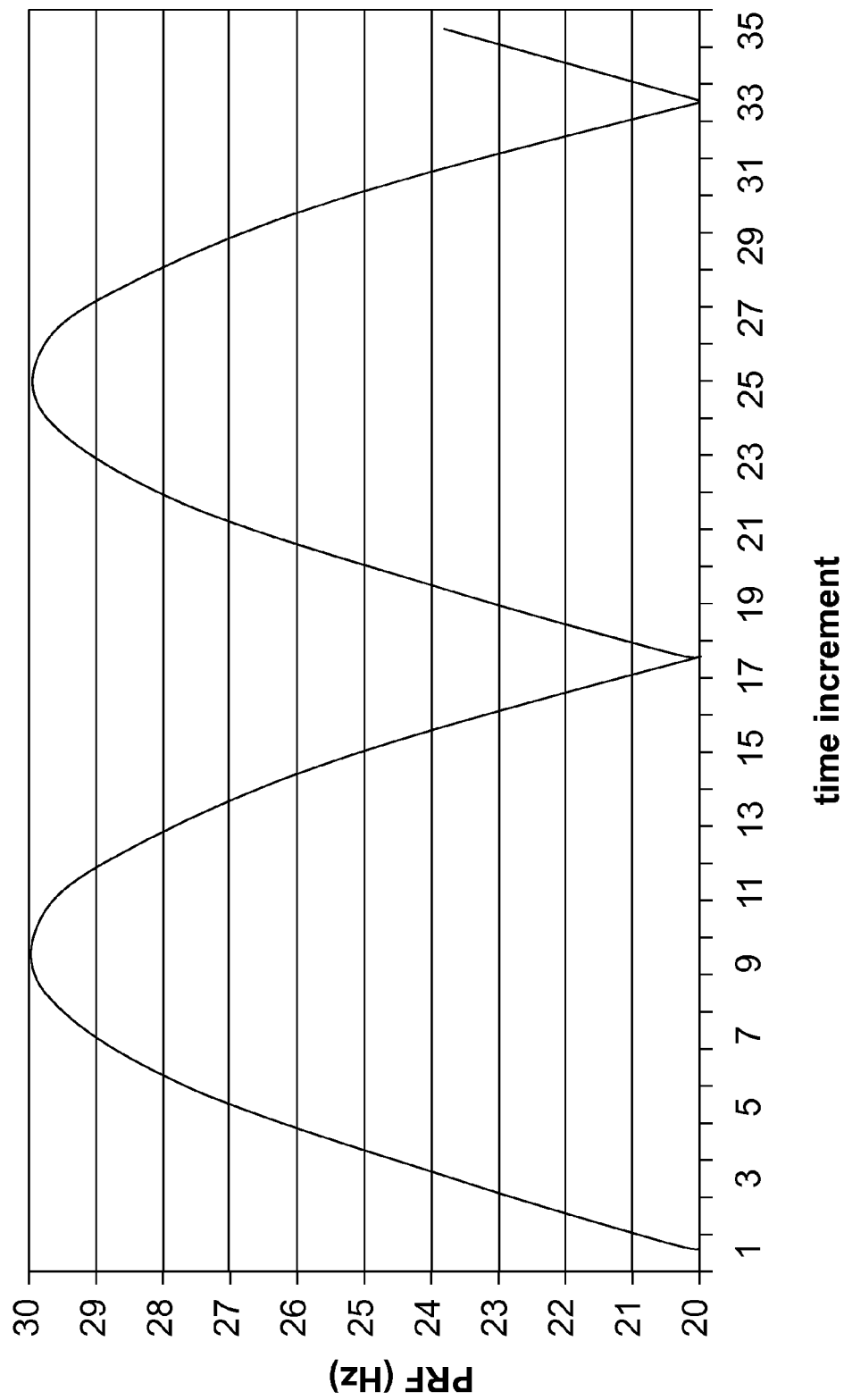
FIG. 8D is a graph illustrating a stimulation frequency function applied in a seconds-based time domain according to an embodiment of the invention.

FIG. 8D is a graph illustrating an exemplary stimulation frequency function applied in a seconds-based time domain to effectuate a reduction in power consumption according to an embodiment of the invention. In one embodiment, f(t) comprises a sinusoidal frequency function that varies between an $f_{max}$ pulse repetition frequency of 50 Hz and an $f_{min}$ pulse repetition frequency of 20 Hz. Stimulation in accordance with such a function may result in an average pulse repetition frequency of 35 Hz, which may maintain or improve neural stimulation efficacy and/or reduce power consumption by approximately 30%. In other embodiments, f(t) may comprise another type of function (e.g., a square wave or a triangle wave) and/or a function that is skewed or weighted relative to a particular frequency target.

Figure 8E:
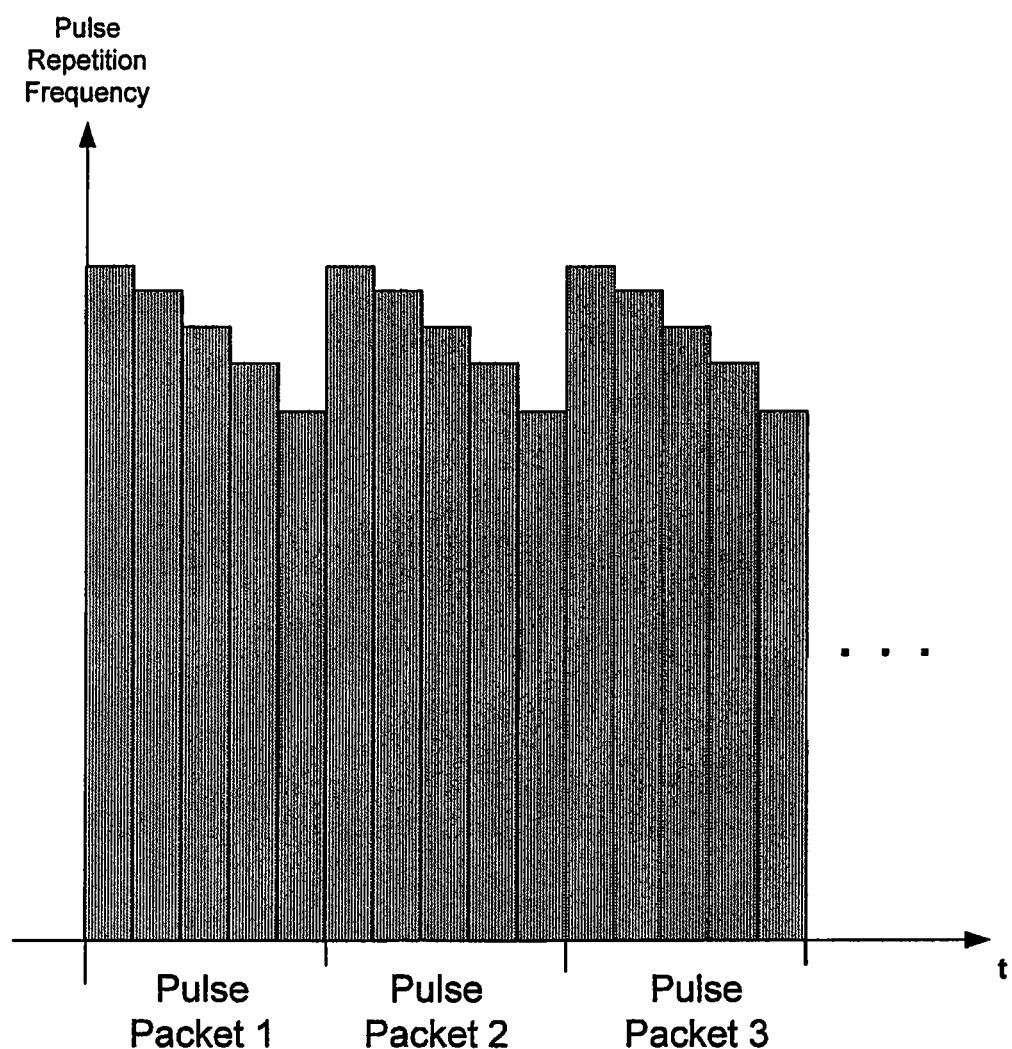
FIG. 8E is a graph illustrating a stimulation frequency modification relative to a subseconds-based time domain according to an embodiment of the invention.

In some embodiments, stimulation signal frequency may be modified relative to a subseconds-based time domain in accordance with a discretized linear or nonlinear frequency chirp pattern or function. FIG. 8E is a graph illustrating an exemplary discretized frequency chirp pattern according to an embodiment of the invention. In one embodiment, a frequency chirp pattern corresponds to a series of pulse packets across and/or within which pulse repetition frequency decreases and/or increases with time or pulse count. For example, each pulse packet may comprise a plurality of biphasic or polyphasic pulses, where an amount of time elapsed between different pulses as referenced with respect to matching pulse phase reference points increases or decreases from one pulse to the next. In another embodiment, a degree, extent, or magnitude of chirping may differ from a given pulse packet to another; and/or chirped pulse packets may be separated by or interspersed with non-chirped pulse packets.

Modification of Stimulation Amplitude Characteristics

In various embodiments, power consumption and/or neural stimulation efficacy may be affected by modifying one or more stimulation amplitude characteristics (e.g., a peak current and/or a peak voltage level) relative to one or more time domains under consideration. In various embodiments, stimulation amplitude characteristics may be varied relative to an hours-based time domain, a seconds-based time domain, a subseconds-based time domain, and/or another type of time domain.

In one embodiment, neural stimulation efficacy may be sustained or improved through the application or delivery of one or more suprathreshold or near-suprathreshold pulses or bursts during a neural stimulation procedure that is primarily characterized by subthreshold stimulation. Such suprathreshold pulses or bursts may occur in a predetermined, aperiodic, or random manner. For example, during a subthreshold stimulation procedure that applies stimulation signals at a current level corresponding to 50% of a movement, EMG, or sensation threshold, a threshold-level or suprathreshold-level pulse or pulse set may be applied at a current level corresponding to 100%, 105%, or 110% of such a threshold once every 3 minutes, or at random or aperiodic times that fall between a minimum and a maximum allowable duration time period.

Figure 9A:
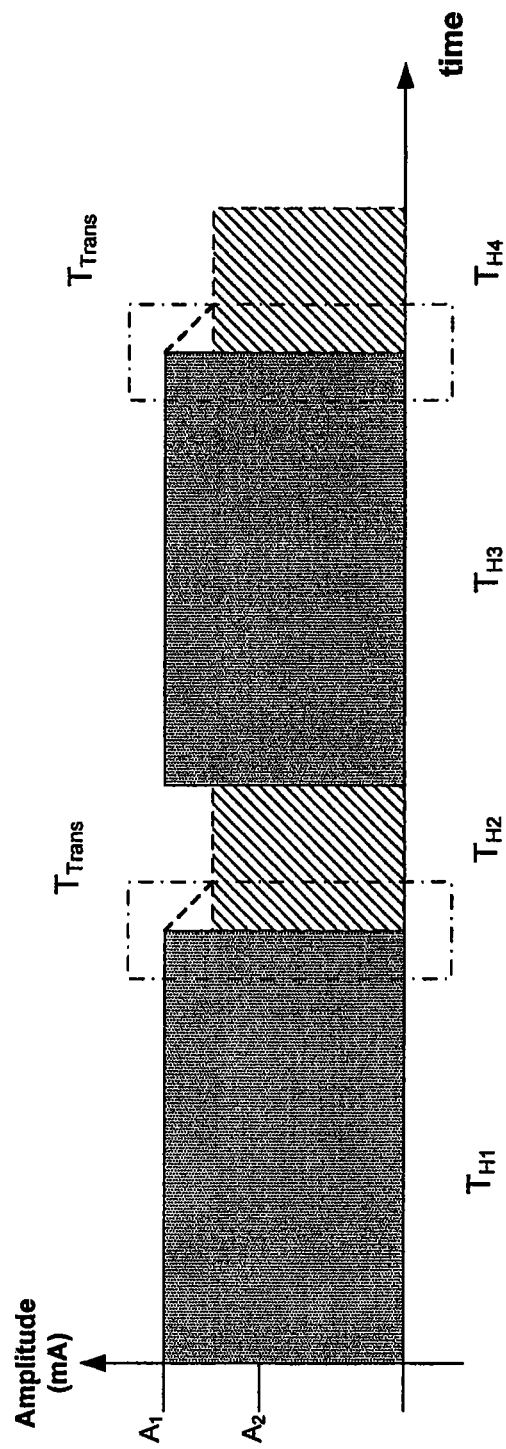
FIG. 9A is a graph illustrating a stimulation level, amplitude, or magnitude modification relative to an hours-based time domain according to an embodiment of the invention.

FIG. 9A is a graph illustrating an exemplary stimulation signal level, amplitude, or magnitude adjustment relative to an hours-based time domain $T_H$ to affect power consumption and/or neural stimulation efficacy according to an embodiment of the invention. In some embodiments, during a first time hours-based period $T_{H1}$, a stimulation signal may have an amplitude $A_1$ that may treat one or more patient symptoms in a most effective, expected most effective, or effective manner. During a second hours-based time period $T_{H2}$, a stimulation signal may have a reduced amplitude $A_2$ that may treat one or more patient symptoms in an effective, generally effective, or adequate manner. Certain embodiments may include a transition period $T_{TRANS}$ between $T_{H1}$ and $T_{H2}$ and/or $T_{H2}$ and $T_{H1}$, wherein neural stimulation amplitude characteristics are varied in a smooth, gradual, or generally gradual manner between $A_1$ and $A_2$. The transition period may correspond to a transition amplitude function or envelope $A_{TRANS}$, which may comprise, for example, a linear or polynomial based change in amplitude versus time.

Depending upon embodiment details, $A_2$ may range from approximately 5% to 95% of $A_1$. In certain embodiments, $A_2$ may be a function of time, possibly varying in a predetermined, quasi-random, or aperiodic manner. Reduced amplitude stimulation may be appropriate, for example, during times that a patient is expected to be asleep or resting. In the event $T_1$ equals approximately 18 hours, $T_2$ equals approximately 6 hours, and $A_1$ is approximately 50% of $A_2$, power consumption may be reduced by approximately 12.5% relative to ongoing stimulation characterized by amplitude $A_1$.

Figure 9B:
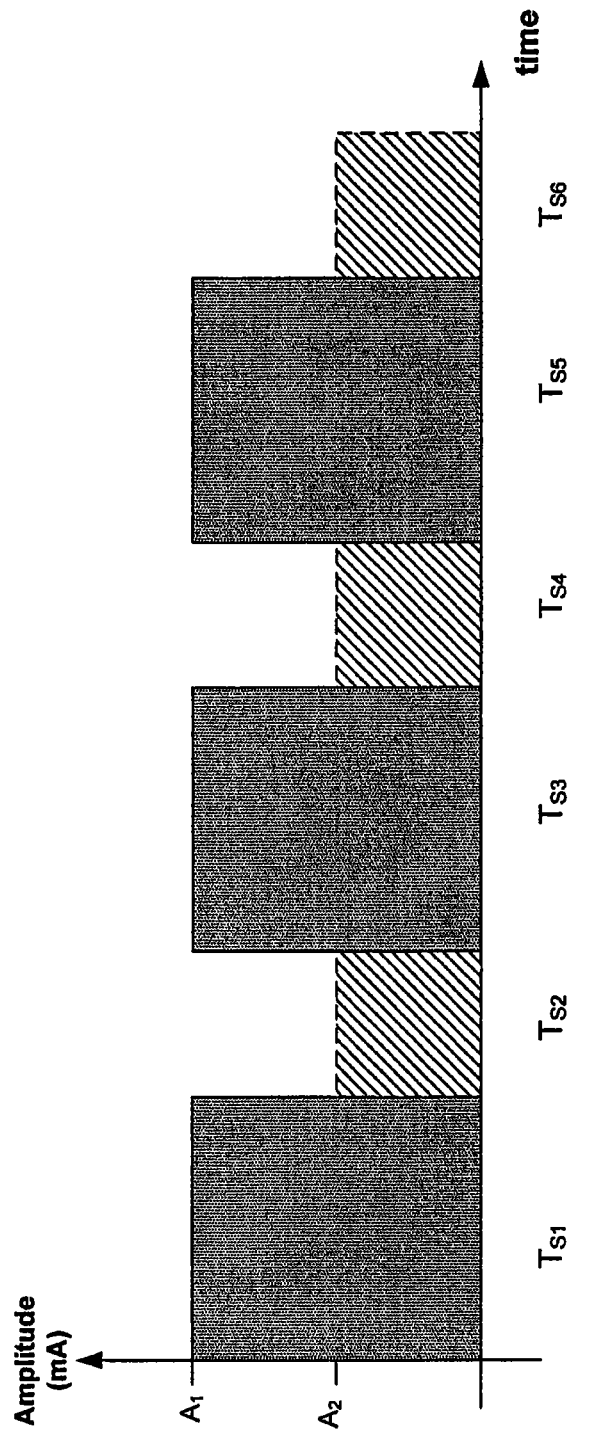
FIG. 9B is a graph illustrating a stimulation level, amplitude, or magnitude modification relative to a seconds-based time domain according to an embodiment of the invention.

FIG. 9B is a graph illustrating an exemplary stimulation signal amplitude adjustment or modification relative to a seconds-based time domain $T_S$ to affect power consumption and/or neural stimulation efficacy according to an embodiment of the invention. In some embodiments, during a first seconds-based time period $T_{S1}$, for example, 20 seconds, a stimulation signal may have an amplitude $A_1$ that may treat one or more patient symptoms in a most effective, expected most effective, or effective manner. During a second time period $T_{S2}$, for example, 10 seconds, a stimulation signal may have a reduced amplitude $A_2$ that may treat one or more patient symptoms in an effective, generally effective, or adequate manner. Depending upon embodiment details, $A_2$ may range from approximately 5% to 95% of $A_1$. In the event that $T_{S1}$ equals approximately 20 seconds, $T_{S2}$ equals approximately 10 seconds, and $A_2$ is approximately 25% of $A_1$, power consumption may be reduced by approximately 7.5% relative to ongoing stimulation characterized by amplitude $A_1$. In certain embodiments, a seconds-based time domain $T_S$ may comprise other and/or multiple reduced amplitude time periods. Additionally or alternatively, an amplitude reduction may be determined in a variable, quasi-random, or aperiodic manner, possibly relative to a minimum and/or maximum amplitude reduction and/or an acceptable level of clinical efficacy.

Figure 9C:
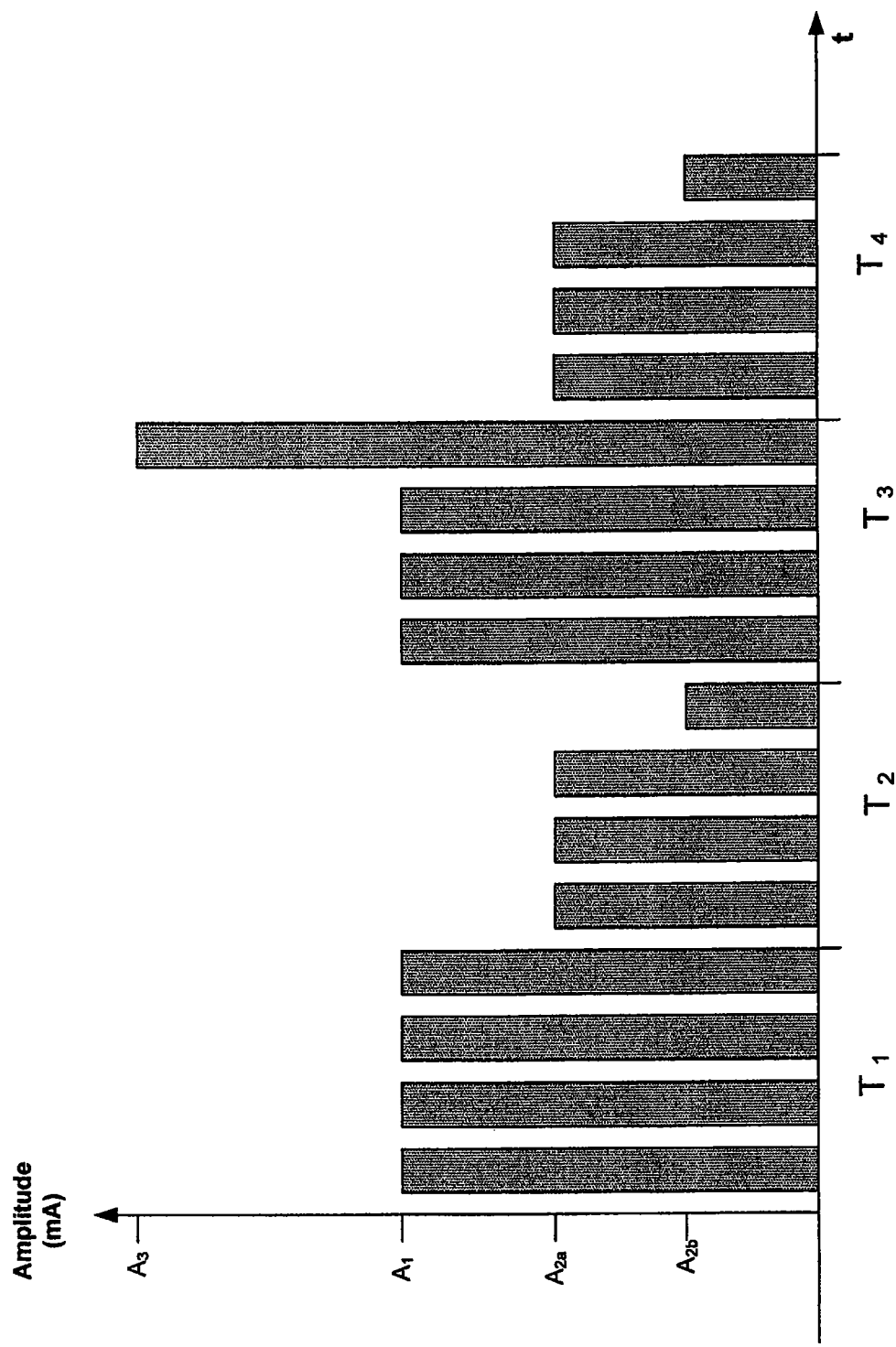
FIG. 9C is a graph illustrating a stimulation level, amplitude, or magnitude modification relative to a subseconds-based time domain according to an embodiment of the invention.

FIG. 9C is a graph illustrating an exemplary stimulation signal amplitude adjustment or modification relative to a subseconds-based time domain $T_{SS}$ to affect power consumption and/or neural stimulation efficacy according to an embodiment of the invention. In one embodiment, a first number of pulses $P_1$ may have an amplitude or average amplitude $A_1$ that is determined or expected to be most effective, effective, or generally effective for treating one or more patient symptoms. In various embodiments, amplitude A1 corresponds to subthreshold-level stimulation, for example, a given percentage (e.g., between 25% and 75%) of a movement or EMG threshold. A second number of pulses $P_2$ may have one or more amplitudes $A_{2A}$, $A_{2B}$ determined or expected to be effective, generally effective, or adequate for treating one or more patient symptoms. In an exemplary embodiment in which $P_1$ equals 6, $P_2$ equals 2, $A_{2A}$ is approximately 50% of $A_1$, and $A_{2B}$ is approximately 25% of $A_1$, power consumption may be reduced by approximately 15.625%. In general, a number of reduced amplitude pulses and/or the amplitudes associated therewith with may depend upon embodiment details, and may depend upon a reduced power consumption target in view of an acceptable level of clinical efficacy.

In one embodiment, neural stimulation efficacy may be maintained or improved through the application or delivery of one or more suprathreshold-level or near-suprathreshold-level pulses or bursts in association with a neural stimulation procedure that includes or is primarily characterized by subthreshold-level stimulation, for example, in a manner indicated in FIG. 9C. Such suprathreshold-level pulses or bursts may occur in a predetermined, aperiodic, or random manner. For example, during a subthreshold-level stimulation procedure that applies stimulation signals at a current level corresponding to 50% of a movement, EMG, or sensation threshold, a suprathreshold-level pulse or pulse set may be applied at a current level corresponding to approximately 100% of such a threshold once every j seconds, twice every k minutes, or at random times that fall between a minimum and a maximum allowable length time period. While FIG. 9C depicts a single threshold-level or suprathreshold-level pulse, in various embodiments neural stimulation may involve additional threshold-level and/or suprathreshold-level pulses, where at least some of such pulses may have different peak amplitudes.

From a patient treatment perspective, the effect(s) associated with an amplitude variation may be identical, essentially identical, analogous, similar, or generally similar to the effect(s) associated with a duty cycle variation and/or a pulse repetition frequency variation in view of an amount of electric charge delivered during a specific pulse phase or pulse subinterval.

Stimulation Intensity Modification

A neurostimulator may be viewed as a device capable of imparting energy to one or more neural populations in a controllable and/or therapeutic manner. Such energy may comprise electrical and/or magnetic stimulation signals that may influence, affect, or alter neural membrane potentials. As described above, stimulation signals may comprise a set or series of pulses or pulse trains. In certain embodiments, an extent or average extent to which neural stimulation affects neural tissue and/or membrane potentials associated therewith may be defined as a neural stimulation intensity.

Neural stimulation intensity may be a function of pulse amplitude; pulse width; interpulse interval, pulse repetition and/or pulse train repetition frequency; pulse count; pulse polarity; and/or one or more other parameters. In certain embodiments, power consumption and/or neural stimulation efficacy may be affected by adjusting, modifying, or modulating a neural stimulation intensity. Such intensity-based modulation may occur relative to one or more time domains described above, for example, a subseconds-based and/or a seconds-based time domain. Particular neural stimulation intensity modification or modulation examples are provided hereafter.

Figure 10A:
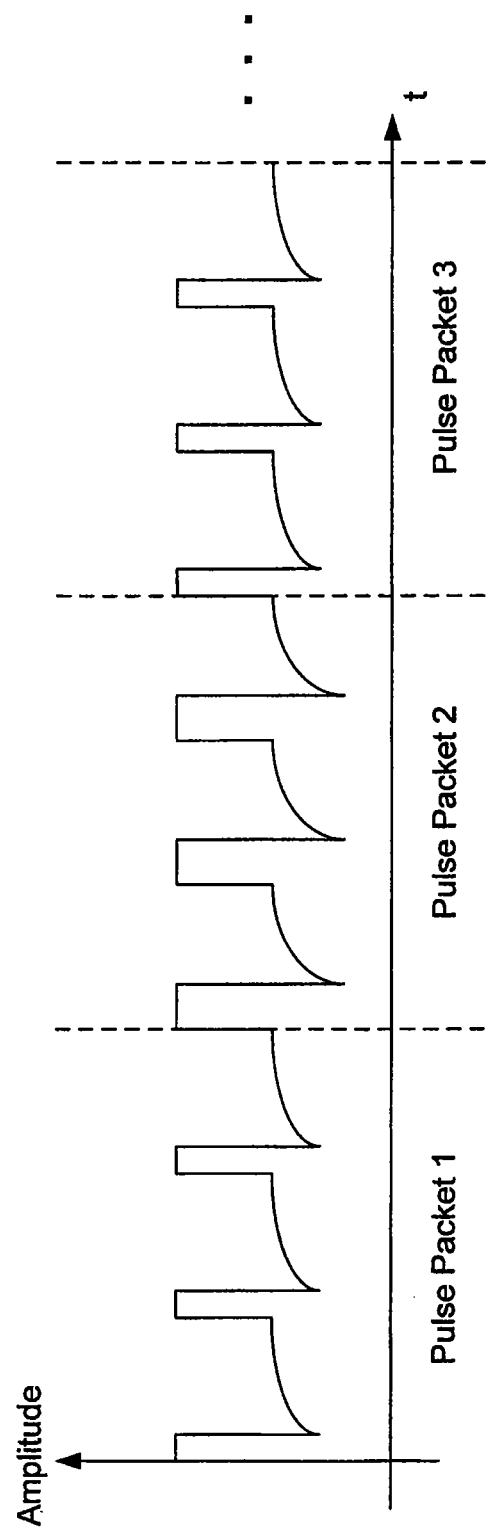
FIG. 10A is a graph illustrating a neural stimulation intensity modulation according to an embodiment of the invention.

FIG. 10A is a graph illustrating an exemplary neural stimulation intensity modulation to affect power consumption and/or neural stimulation efficacy according to an embodiment of the invention. In one embodiment, the neural stimulation may comprise a plurality of pulses that exhibit one or more types of pulse-width variation from a given or particular pulse to another pulse. For instance, pulses within a first pulse packet may have a first-phase pulse width that is a multiple or fraction (e.g., approximately one-half) of a first-phase pulse width of pulses within a second pulse packet. A third pulse packet may be identical or essentially identical to or different from the first or second pulse packet. Depending upon embodiment details, pulse-width variation may occur in a periodic, aperiodic, or pseudo-random manner across or within a set of pulse packets. Those skilled in the art will understand that the pulses shown in FIG. 10A are not to scale. Those skilled in the art will also understand that a second pulse phase may vary in duration in the event that a peak magnitude associated with the second pulse phase reaches a limit or bound.

From a patient treatment perspective, the effect(s) associated with a pulse width variation may be identical, essentially identical, analogous, or similar to the effect(s) associated with an amplitude or other type of variation because both pulse width variation and amplitude variation may alter an amount of electrical charge delivered to the patient during a specific pulse phase or pulse subinterval.

Figure 10B:
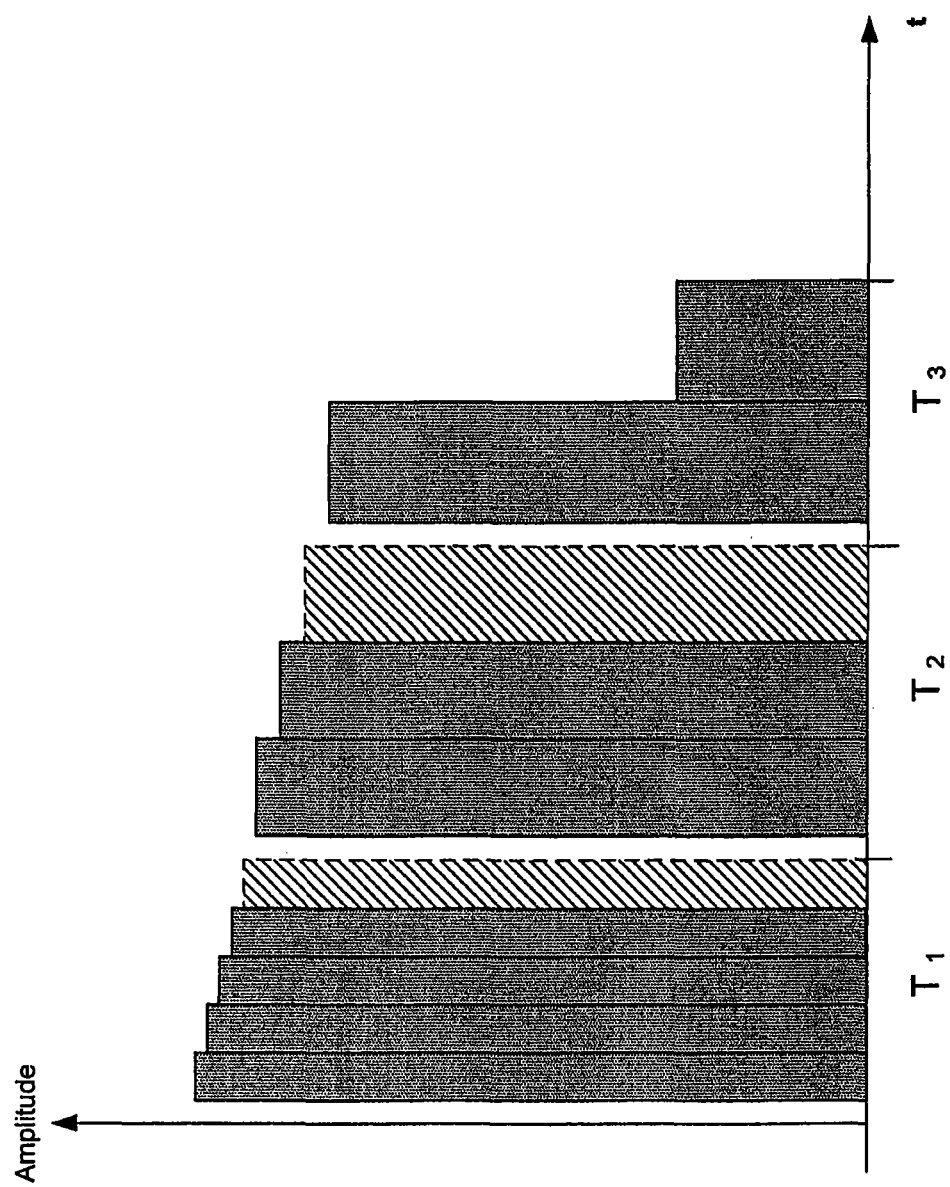
FIG. 10B is a graph illustrating a neural stimulation intensity modulation according to another embodiment of the invention.

FIG. 10B is a graph illustrating an exemplary neural stimulation intensity modulation to affect power consumption and/or neural stimulation efficacy according to another embodiment of the invention. In one embodiment, the neural stimulation may comprise an alternating series of pulse packets, wherein neural stimulation intensity varies from one pulse packet to another. For example, a first pulse packet or group may comprise a first number of pulses characterized by a first pulse repetition frequency and a first peak amplitude; and a second and a third pulse packet or group may comprise a second and a third number of pulses, respectively characterized by at least one reduced pulse repetition frequency and at least one reduced peak amplitude. Additionally or alternatively, one or more pulses may be omitted or skipped within particular pulse packets, and/or one or more first-phase pulse widths may differ between or within pulse packets.

Modification of Spatiotemporal Stimulation Characteristics

In some embodiments, the neural stimulation may be applied in one or more spatiotemporally varying manners to affect power consumption and/or neural stimulation efficacy. Depending upon embodiment details, particular electrode assemblies and/or electrical contacts may be selectively activated in accordance with their type, location, and/or orientation. Such selective activation may occur in a predetermined, aperiodic, or random manner. A wide variety of spatiotemporal activation patterns may exist, possibly depending upon the nature of a patient's neurologic dysfunction, stimulation site locations, desired efficacy characteristics, and/or embodiment details.

Figure 1C:
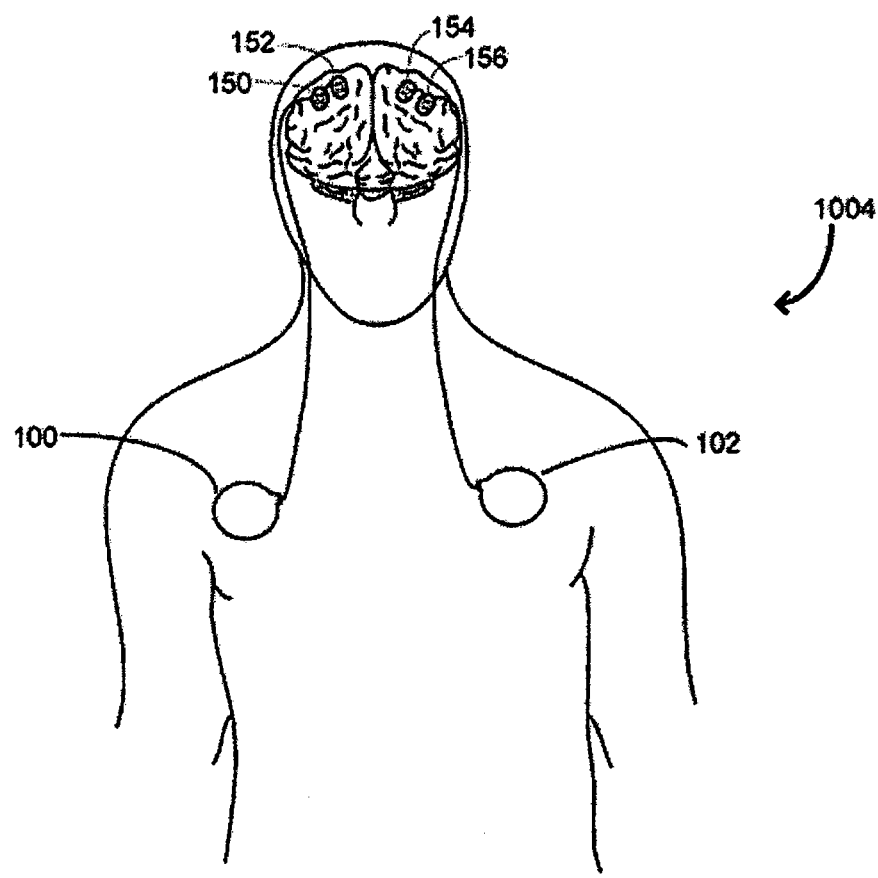
Figure 11A:
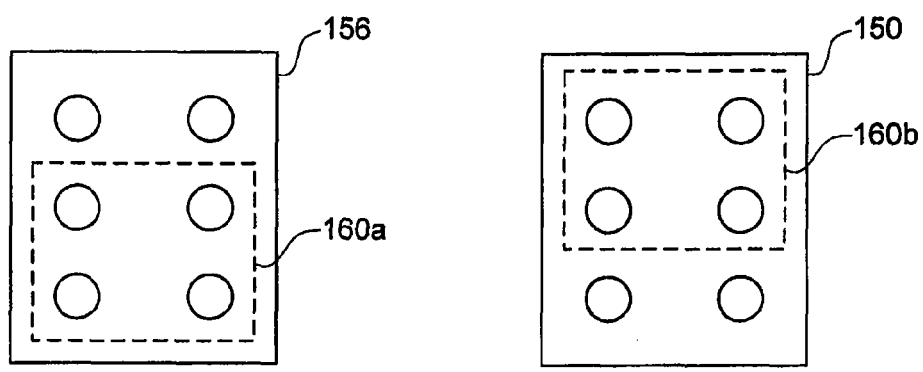
FIG. 11A is a schematic illustration corresponding to a set of spatiotemporal electrical contact activation patterns according to an embodiment of the invention.
Figure 11A:
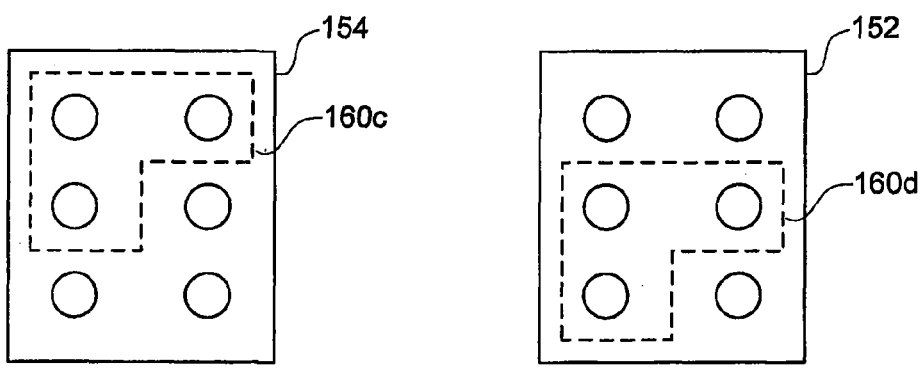

Referring again to FIGS. 1A through 1C, like reference numbers indicate like or analogous elements. In one exemplary spatiotemporal activation pattern, electrical contacts 160 carried by an electrode assembly 150 may be pairwise activated in a predetermined or pseudo-random manner. FIG. 11A illustrates another exemplary spatiotemporal activation pattern 300 according to an embodiment of the invention. A first set of electrical contacts 160a carried by a left hemisphere electrode assembly 154, 156 may be activated during a first seconds-based time domain; after which a first set of electrical contacts 160b carried by a right hemisphere electrode assembly 150, 152 may be activated during a second seconds-based time domain; after which a second set of electrical contacts 160c carried by the left hemisphere electrode assembly 154, 156 may be activated during a third seconds-based time domain; after which a second set of electrical contacts 160d carried by the right hemisphere electrode assembly 150, 152 may be activated during a fourth seconds-based time domain. Such varying activation patterns may continue on a predetermined, aperiodic, or quasi-random basis depending upon embodiment details.

Figure 11B:
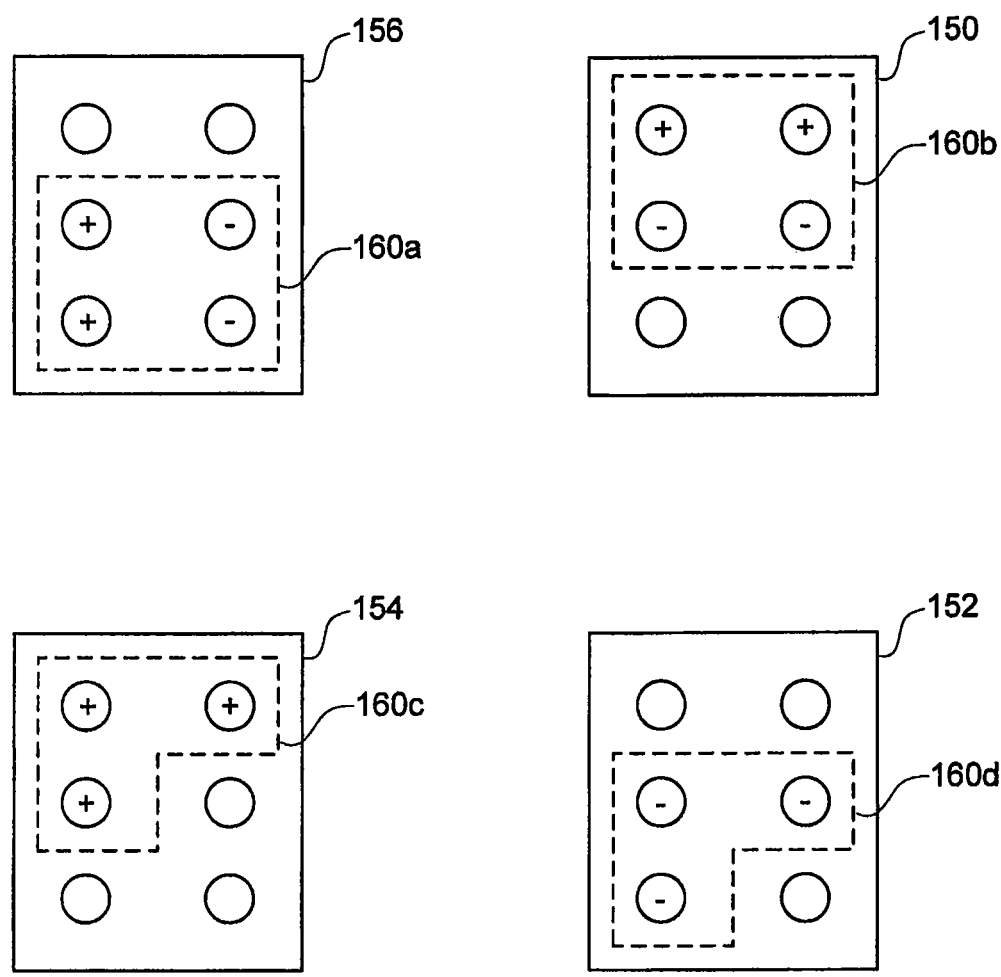
FIG. 11B is a schematic illustration corresponding to a set of spatiotemporal stimulation signal polarity variations according to another embodiment of the invention.

Stimulation signal polarity variations may be considered in the context of spatiotemporal characteristics. FIG. 11B illustrates exemplary stimulation signal polarity variations corresponding to the spatiotemporal activation pattern shown in FIG. 11A. In particular, FIG. 11B illustrates different bipolar stimulation configurations(top of Figure), and a cathodal unipolar and anodal unipolar stimulation configuration (bottom of Figure), each of which may involve circuit completion using a remote electrode assembly that is biased at a polarity opposite or neutral with respect to the polarities shown at the bottom of FIG. 11B. Those skilled in the art will understand that a wide variety of other stimulation signal polarity variations are possible.

Combined Approaches

Two or more of the approaches described above for affecting power consumption and/or neural stimulation efficacy may be simultaneously or sequentially combined. Any given combination may serve to preserve or increase neural stimulation efficacy, and/or reduce power consumption. For example, in association with a spatiotemporal activation pattern 300 such as that described above with reference to FIGS. 11A and 11B, one or more electrical contacts 160 may periodically, aperiodically, or randomly apply or deliver a set of threshold-level and/or suprathreshold-level pulses at one or more times, possibly during a treatment program that primarily involves subthreshold-level stimulation. Additionally or alternatively, left and right hemisphere stimulation pulse repetition frequencies may alternate between 30 Hertz and 80 Hertz; left and right hemisphere stimulation signal polarity may alternate to apply unipolar and bipolar stimulation in a successive, aperiodic, or random manner; and/or the durations of the first, second, third, and fourth seconds-based time domains, and therefore a set of left hemisphere and right hemisphere duty cycles, may be equal or unequal, and/or possibly varying.

As another example, a treatment program may comprise a continuous or generally continuous stimulation period characterized by a varying neural stimulation intensity; and a set of quiescent or nearly quiescent periods, where one or more quiescent periods may correspond to an interruption period as described above. In such an example, the continuous stimulation period and/or one or more quiescent periods may be defined relative to a seconds-based, an hours-based, and/or other type of time domain. Moreover, particular portions of the continuous stimulation period may exhibit different peak current or voltage amplitudes.

As yet another example, a treatment program may involve a set of neuro-burst and possibly other types of stimulation periods, where one or more interburst and/or intraburst stimulation parameters may vary with time in a predetermined, pseudo-random, and/or aperiodic manner. For instance, during a given neuro-burst stimulation period, an interburst frequency may vary within a lower bound and an upper bound corresponding to a type of neuro-burst stimulation under consideration. Additionally or alternatively, one or more pulse or burst polarities may vary in accordance with cathodal unipolar, anodal unipolar, and bipolar polarity configurations. Also, a series of intraburst pulse repetition frequencies may vary with time (e.g., between 100 Hz and 200 Hz in a periodic, aperiodic, or random manner).

Essentially any of the above approaches for reducing power consumption and/or affecting neural stimulation efficacy may be combined in a variety of manners. The resulting neural stimulation may address one or more patient states, conditions, symptoms, and/or functional deficits in an effective, generally effective, adequate, or generally acceptable manner.

Preprogrammed or Programmably Selectable Parameter Variation Modes

Multiple types of stimulation signal parameter variation modes may be preprogrammed in a stimulation device such as an IPG, and/or programmably selected during a programming session. In certain modes, particular stimulation signal parameter variations may be based upon or occur relative to a set of baseline or previously established parameter values, which may be patient-specific.

FIG. 16 provides a list of representative types of stimulation signal parameter variation or modulation modes that may be programmably selected in association with an IPG programming session. As indicated in Table 1, such modes may provide for multiple types of pulse width variation, duty cycle variation, pulse repetition frequency variation, and/or polarity variation. Other types of stimulation parameter modulation modes may also be provided in addition to or instead of those indicated in FIG. 16, possibly depending upon stimulation device capabilities. Certain modes may involve multiple or combined types of stimulation signal parameter variation in a manner analogous to that described above.

Additional Neural Stimulation Efficacy and/or Power Consumption Considerations

Neural stimulation efficacy may depend upon one or more stimulation parameter values. For instance, neural stimulation efficacy may be pulse repetition frequency dependent. Moreover, depending upon the nature of a patient's neurologic dysfunction, neural stimulation efficacy may degrade or wane over time in a manner that depends upon pulse repetition frequency. Thus, a first pulse repetition frequency or pulse repetition frequency range may be associated with rapid or generally rapid onset of symptomatic benefit, but a short or relatively brief benefit duration or half-life. A second pulse repetition frequency or pulse repetition frequency range may be associated with a slower or delayed onset of symptomatic benefit, but a longer benefit duration or half-life. The neural stimulation efficacy corresponding to the first and second pulse repetition frequencies may be essentially identical or different.

As an example, a patient exhibiting symptoms of Parkinson's Disease may experience rapid or reasonably rapid (e.g., approximately 10 to 30 minutes after initiation of neural stimulation) and/or significantly effective relief from one or more symptoms for approximately 1.5 to 2.5 hours in response to neural stimulation characterized by a pulse repetition frequency of approximately 30 Hertz. Neural stimulation efficacy may progressively taper off if 30 Hertz stimulation continues. Approximately 1.0 hours after initiation of the 30 Hertz neural stimulation, application of neural stimulation characterized by a pulse repetition frequency of approximately 10 Hertz or less may result in longer lasting or more sustained symptomatic benefit, although in some situations such benefit may be less effective relative to the magnitude of symptomatic relief. The 10 Hertz stimulation may also reduce power consumption.

Figure 12:
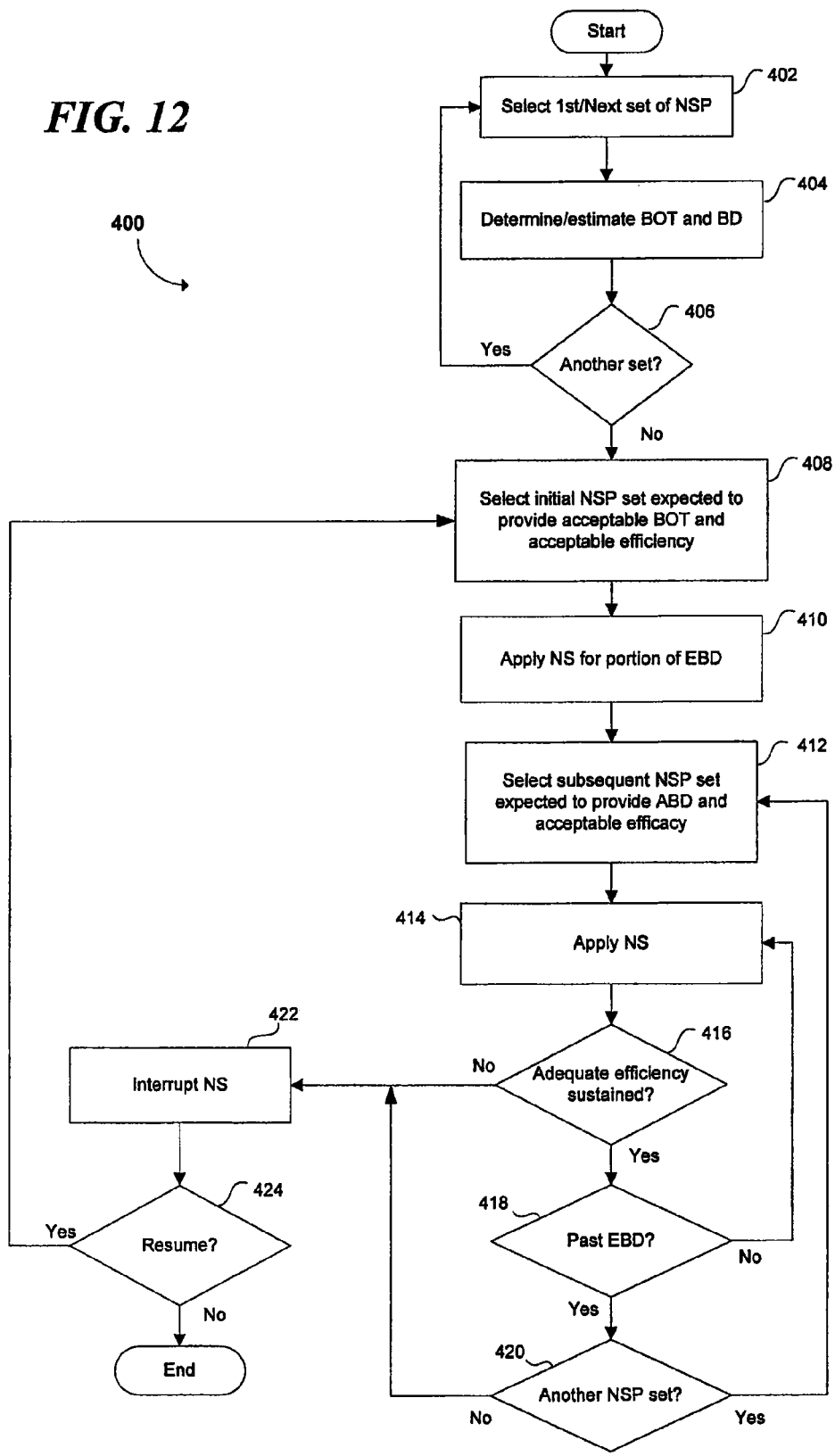
FIG. 12 is a flowchart illustrating various methods for reducing power consumption and/or affecting neural stimulation efficacy.

FIG. 12 is a flowchart illustrating various methods for reducing power consumption and/or affecting neural stimulation efficacy. In one embodiment, a method 400 comprises a first selection procedure 402 that involves selecting, identifying, and/or retrieving a set of neural stimulation parameters (NSPs); and a first determination procedure 404 that involves determination, measurement, and/or estimation of a benefit onset time (BOT) and/or a benefit duration (BD) corresponding to the set of neural stimulation parameters currently under consideration. The method 400 may additionally comprise a second determination procedure 406 that involves returning to the first selection procedure 402 in the event that consideration of one or more additional neural stimulation parameter sets is desired.

In one embodiment, the method 400 comprises a second selection procedure 408 that involves selection of a set of neural stimulation parameters that is expected to provide or result in a rapid, reasonably rapid, or acceptable benefit onset time and an acceptable level of efficacy. The method 400 may further comprise a first application procedure 410 that involves the application of neural stimulation signals to the patient in accordance with the neural stimulation parameter set under consideration, for a portion of an expected or estimated benefit duration (EBD) associated with such a parameter set. The expected benefit duration may correspond, for example, to an expected benefit half-life.

The method 400 may also comprise a third selection procedure 412 that involves selection of a set of neural stimulation parameters that is expected to provide or result in a prolonged, good, or acceptable benefit duration and an acceptable level of efficacy. The method 400 may correspondingly comprise a second application procedure 414 that involves the application of neural stimulation signals to the patient in accordance with the stimulation parameter set currently under consideration.

In one embodiment, the method 400 may comprise a first evaluation procedure 416 that involves determining whether a good, acceptable, or adequate level of efficacy is maintained or sustained relative to the neural stimulation parameter set currently under consideration. If not, the method 400 may comprise an interruption procedure 422 that involves temporarily interrupting or pausing the application of neural stimulation signals to the patient; and a second evaluation procedure 424 that involves determining whether to resume or terminate the neural stimulation. If resumption of neural stimulation is desired, the method 400 may return to the second selection procedure 408 in one embodiment; otherwise, the method 400 may comprise a termination procedure.

In the event that a good, acceptable, or adequate level of efficacy is maintained in view of the neural stimulation parameter set currently under consideration, the method 400 may comprise a second evaluation procedure 418 that involves determining whether the neural stimulation has been applied beyond a time that may correspond to an expected benefit duration, for example, an expected or estimated benefit half-life. If the neural stimulation has not been applied beyond such a time, the method 400 may return to the second application procedure 414.

If the neural stimulation has been applied or delivered beyond a time that corresponds to an expected benefit duration, the method 400 may comprise a third determination procedure 420 that involves determining whether consideration of another neural stimulation parameter set is desired. If so, the method 400 may return to the second application procedure 412; otherwise, the method 400 may return to the interruption procedure 422.

In general, neural stimulation efficacy may be maintained or enhanced when portions of one or more target neural populations or neural ensembles perceive applied stimulation signals as novel or generally novel. Neural stimulation efficacy may be maintained or enhanced through the application of stimulation signals that vary in one or more manners described above. In certain embodiments, such variation may occur in a progressive, cyclical, and/or ongoing manner. Progressively increasing novelty or ongoing change may occur by successively varying greater numbers of stimulation parameters and/or varying one or more given stimulation parameters in a more unpredictable or complex manner with time. In some embodiments, once the simultaneous or sequential variation of a given number of stimulation parameters has occurred, a reduction in a number of varied parameters and/or a simplification in variation complexity may occur. Additionally or alternatively, neural stimulation may be temporarily interrupted or discontinued to increase a likelihood a) that the absence of neural stimulation is a novel condition for a neural population; and/or b) the application of stimulation signals exhibiting progressively increasing novelty can resume again starting with a small number and/or simple types of stimulation signal parameter variations. In some embodiments, stimulation parameter variation may be based upon an extent to which symptomatic benefit has waned or degraded over time.

Figure 13:
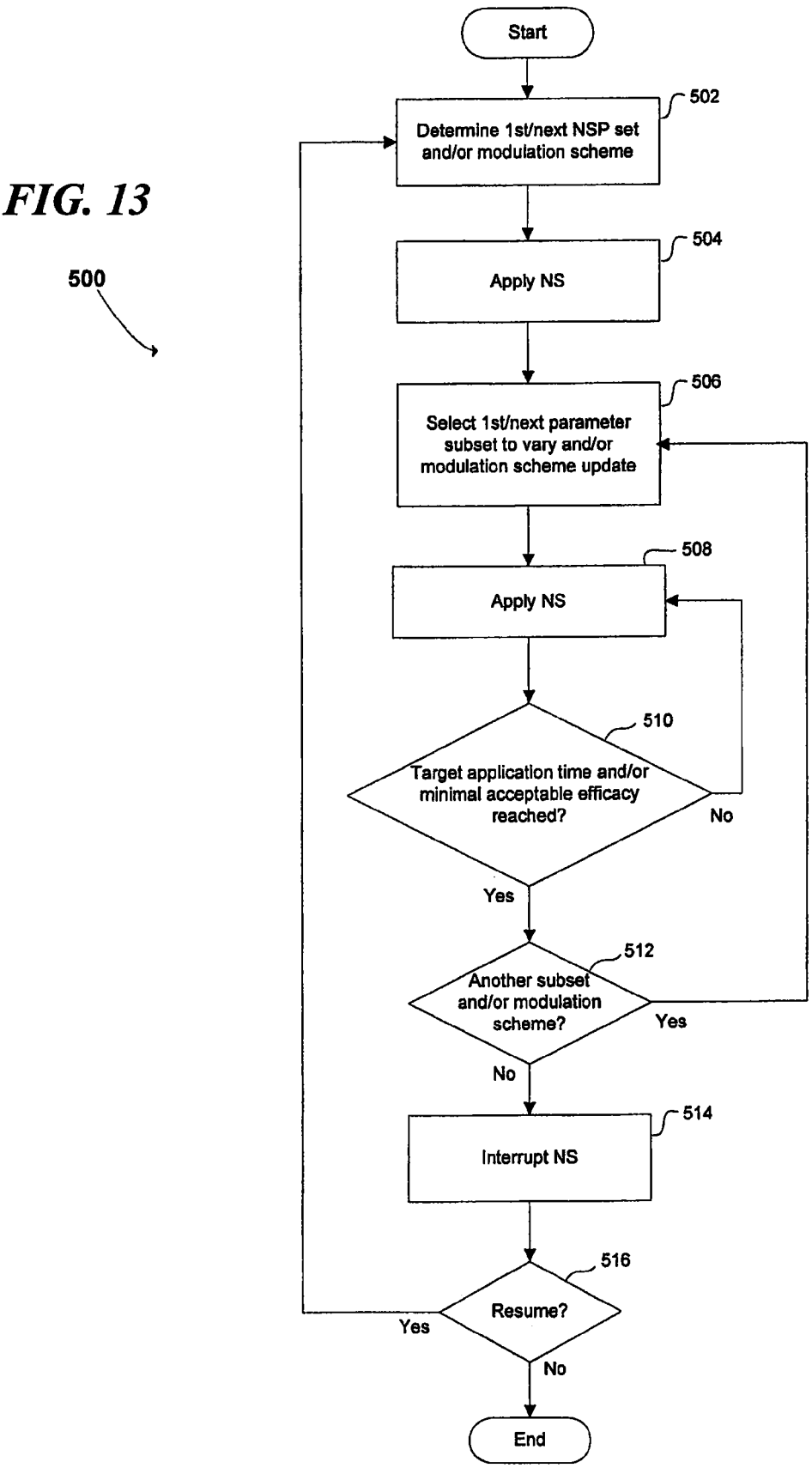
FIG. 13 is a flowchart illustrating various other and/or additional methods affecting power consumption and/or neural stimulation efficacy.

FIG. 13 is a flowchart illustrating various other and/or additional methods for affecting power consumption and/or neural stimulation efficacy. Particular methods corresponding to FIG. 13 may facilitate or effectuate the application of stimulation signals to particular neural populations in a manner that may be characterized by progressively increased, augmented, and/or supplemental novelty.

In one embodiment, a method 500 comprises a first selection procedure 502 that involves selection, determination, identification, and/or retrieval of a first or next neural stimulation parameter set and/or a first or next stimulation parameter modulation function, procedure, or scheme; and a first application procedure 504 that involves the application or delivery of neural stimulation signals to the patient in accordance with the neural stimulation parameter set and/or modulation scheme currently under consideration.

The method 500 may further comprise a second selection procedure 506 that involves the selection of a first, next, updated, additional, or different subset of neural stimulation parameters to change, adjust, vary, or modify, and/or the selection of a first, next, updated, additional, or different stimulation parameter modulation scheme; and a second application procedure 508 that involves application of neural stimulation signals to the patient in accordance with the adjusted parameter subset and/or modulation scheme. Depending upon that nature and/or extent of a patient's neurologic dysfunction, patient condition, and/or embodiment details, the adjustment or modification of a selected stimulation parameter subset may involve one or more types of neural stimulation parameter adjustment, modification, and/or variation described above.

In one embodiment, the method 500 may additionally comprise a first evaluation procedure 510 that involves determining whether a target stimulation signal application time (which may correspond, for example, to an expected or estimated benefit duration) and/or a minimum acceptable level of efficacy have been reached. If not, the method 500 may return to the second application procedure 508. In the event that a target stimulation signal application time and/or a minimum acceptable efficacy level have been reached, the method 500 may comprise a determination procedure 512 that involves determining whether adjustment or modification of the same or a different stimulation parameter subset and/or modulation scheme is desired or warranted. If so, the method 500 may return to the second selection procedure 506.

In certain embodiments, the method 500 may also comprise an interruption procedure 514 that involves temporarily interrupting or pausing the application of stimulation signals and/or one or more other portions of a treatment program. The method 500 may further comprise a second evaluation procedure 516 that involves determining whether to resume the application of stimulation signals and/or one or more portions of the treatment program to the patient. If so, the method 500 may return to the first selection procedure 500; otherwise, the method may comprise a termination procedure.

Stimulation Adjustment Based upon Lasting Neurofunctional Change

Neural stimulation provided, applied, or delivered in accordance with certain embodiments of the present invention may aid and/or give rise to one or more cumulative, persistent, and/or semipersistent neurofunctional effects and/or may facilitate and/or effectuate neuroplastic changes within a patient's brain (e.g., within one or more cortical regions). Depending upon embodiment details and/or the nature of a patient's neurologic dysfunction, condition, and/or treatment history, one or more of such effects and/or changes may be permanent, essentially permanent, lasting, generally lasting, persistent, and/or somewhat persistent in the absence of neural stimulation. Additionally or alternatively, one or more of such effects and/or changes may exist to a limited extent and/or for a limited time interval after neural stimulation is interrupted or discontinued, possibly such that the extent and/or interval of existence increases during and/or following the course of a treatment program. A neurofunctional effect that persists for a limited or increasing time period following the interruption or cessation of neural stimulation may increase a likelihood that subsequent reduced power or less frequent neural stimulation may provide good or adequate symptomatic benefit. Moreover, in certain situations, a persistent or generally persistent neurofunctional effect may aid in countering undesirable neural adaptation or neural accommodation to stimulation signals, particularly since symptomatic benefit may be achieved with less intense and/or less frequent stimulation as a persistent neurofunctional effect develops.

As an example, cortical stimulation may facilitate or enhance at least partial functional recovery of a deficit associated with stroke, traumatic brain injury, cerebral palsy, movement disorders, and/or other types of neurologic dysfunction on a generally lasting or long term basis, possibly through mechanisms involving neuroplastic change. Neural stimulation may be particularly effective at facilitating or effectuating lasting, persistent, and/or semipersistent neurofunctional change when stimulation is applied in conjunction or association with one or more types of adjunctive or synergistic therapy (e.g., a behavioral therapy that is neurofunctionally relevant with respect to one or more patient states, conditions, and/or symptoms).

Neural stimulation systems and/or methods directed toward providing a lasting or long term reduction in one or more neurofunctional deficits are described in U.S. application Ser. No. 09/802,808, entitled "Methods and Apparatus for Effectuating a Lasting Change in a Neural Function of a Patient," filed on Mar. 8, 2001, incorporated herein by reference. Cortical stimulation directed toward treating a set of movement disorder symptoms and/or symptoms corresponding to one or more other types of neurologic dysfunction may facilitate a reduction in the severity or magnitude of one or more symptoms even in the absence of such stimulation. Cortical stimulation systems and/or methods for treating Parkinson's Disease and/or other movement disorders are described in detail in U.S. patent application Ser. No. 10/731,731, entitled "System and Method for Treating Parkinson's Disease and Other Movement Disorders," filed on Dec. 9, 2003; and U.S. patent application Ser. No. 10/782,526, entitled "Systems and Methods for Enhancing or Optimizing Neural Stimulation Therapy for Treating Symptoms of Parkinson's Disease and/or Other Neurological Dysfunction," filed on Feb. 19, 2004.

Evidence of a lasting, persistent, or semipersistent change in a patient state, condition, and/or functional deficit may indicate that one or more portions of a treatment program associated with a treatment program may be modified or varied in a manner that affects power consumption and/or neural stimulation efficacy while retaining 1) a high or an acceptable degree of efficacy relative to one or more patient states, conditions, and/or functional deficits; and/or 2) a likelihood that the modified neural stimulation may facilitate or effectuate further lasting, persistent, or semipersistent change. In certain embodiments, modification of a treatment program based upon evidence of a lasting change may comprise modification of one or more neural stimulation procedures and/or adjunctive therapy procedures (e.g., a drug-related procedure and/or a behavioral therapy procedure).

A lasting change in a patient state, condition, and/or functional deficit may identified, monitored, and/or measured through the acquisition and/or analysis of patient state information at one or more times, possibly in association with an interruption of or a parametric modification corresponding to one or more neural stimulation and/or adjunctive therapy procedures. Such a parametric reduction may comprise, for example, a reduction in a neural stimulation dose and/or a drug dose across one or more time domains.

Acquisition of patient state information may involve one or more patient monitoring units 200 and/or human observation. In certain embodiments, patient state information may comprise and/or be based upon one or more types of electrophysiological signals such as EMG, EEG, ECoG, MEG, evoked potential, neural conduction latency, and/or other signals. Patient state information may additionally or alternatively comprise and/or be based upon one or more types of functional and/or behavioral correlate signals and/or behavioral assessment data. Functional or behavioral correlate signals may comprise, for example, accelerometer signals, force and/or strain gauge signals, data and/or results corresponding to tests of patient performance or capability, and/or other types of signals.

In some embodiments, patient state information may comprise cerebro-muscular and/or cerebro-cerebral coherence information; cerebro-muscular and/or cerebro-cerebral partial coherence information; event-related desynchronization information; power and/or frequency spectra information; silent period (e.g., cortical and/or peripheral silent period) information; neural imaging (e.g., MRI, fMRI, DTI, and/or PET scan) information; and/or other measured and/or calculated information or signals. Particular manners of acquiring and/or interpreting coherence-related information are described in "The cerebral oscillatory network of parkinsonian resting tremor," Lars Timmermann et al., *Brain* (2003), Vol. 126, p. 199-212.

Depending upon embodiment details, acquisition of patient state information may occur prior to and/or at the start of a treatment program; at one or more time periods or intervals (e.g., at or every 3 weeks; 3 months; 6 months; or 1 or more years) during or following the course of a treatment program; and/or in response to patient attainment of a given level of functional performance or improvement. In various embodiments, functional performance may be assessed and/or scored in accordance with one or more types of standardized tests, for example, the Unified Parkinson's Disease Rating Scale (UPDRS).

Evidence of a lasting change may indicate that further lasting or possibly lasting change and/or improved, maintained, or altered neural stimulation efficacy may be facilitated and/or effectuated in association with one or more treatment program modifications. Such treatment program modifications may comprise procedures involving the determination of a new or updated initial stimulation configuration; and/or the determination of one or more new or updated adjusted stimulation configurations, which may involve one or more types of stimulation parameter or characteristic adjustments or variations described above, and/or one or more types of procedures described above.

Figure 14:
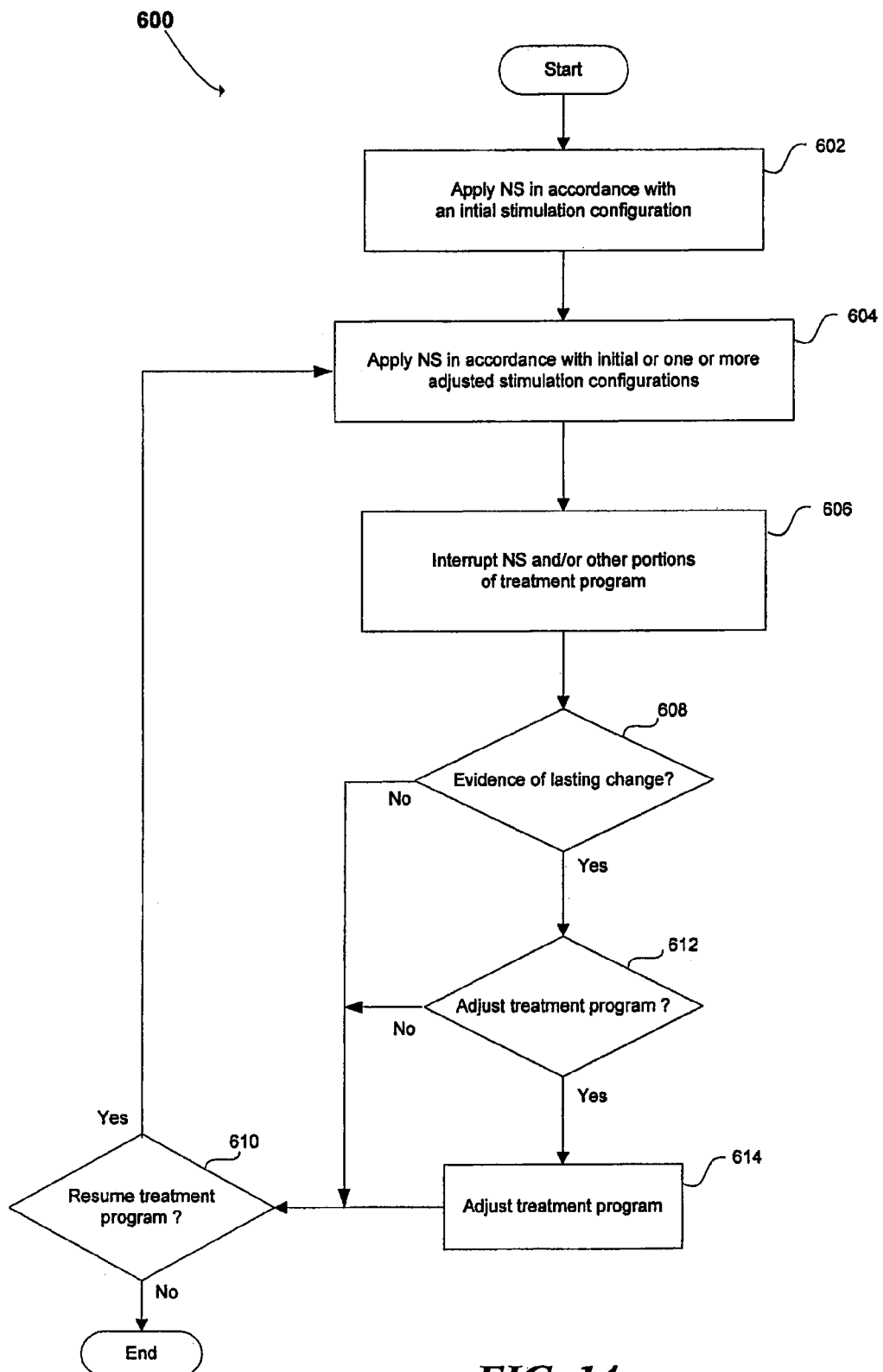
FIG. 14 is a flowchart illustrating various methods for adjusting, modifying, or updating a treatment program based upon evidence of a cumulative, persistent, or semipersistent neurofunctional effect.

FIG. 14 is a flowchart illustrating various methods for adjusting, modifying, or updating a treatment program based upon evidence of a cumulative, persistent, or semipersistent neurofunctional effect. In one embodiment, a method 600 comprises an initial stimulation procedure 602 that may involve applying neural stimulation to a patient in accordance with an initial stimulation configuration associated with a treatment program. The method 600 may further comprise an adjusted stimulation procedure 604 that involves application of neural stimulation procedures to the patient in accordance with one or more adjusted stimulation configurations associated with the treatment program. The method 600 may additionally comprise an interruption procedure 606 that involves interrupting one or more portions of the treatment program. Depending upon embodiment details, the interruption procedure 606 may result in a temporary interruption of the neural stimulation, a temporary interruption of a drug-related procedure, and/or another type of temporary treatment program interruption.

In one embodiment, the method 600 also comprises a monitoring procedure 608 that involves determining whether evidence of a cumulative, persistent, or semipersistent neurofunctional effect exists. If not, the method 600 may comprise a resumption decision procedure 610 that involves determining whether to resume the treatment program. If treatment program resumption is desired, the method 600 may return to the adjusted stimulation procedure 604 in certain embodiments; otherwise, the method 600 may comprise a termination procedure.

In the event that evidence of a cumulative, persistent, or semipersistent neurofunctional effects exists, the method 600 may comprise an adjustment decision procedure 612 that involves determining whether to adjust, modify, or vary one or more portions of the treatment program. If treatment program adjustment is not desired or warranted, the method 600 may return to the resumption decision procedure 610.

If treatment program is adjustment is desired or warranted, the method 600 may comprise an adjustment procedure 614 that involves adjusting, modifying, or varying the treatment program in one or more manners. An adjustment procedure 614 may comprise, for example, a reduction in a neural stimulation amplitude, a pulse repetition frequency, and/or a duty cycle; specification, definition, or identification of a different or modified set of mathematical functions or operations corresponding to one or more neural stimulation parameters; specification or identification of a different or modified set of electrode assemblies, electrical contacts, and/or signal transfer elements that may be activated an any given time; a reduction in a drug dose and/or specification of a different drug; and/or a reduction or increase in a number of behavioral therapy sessions and/or specification of another and/or an additional behavioral therapy. Following the adjustment procedure 614, in one embodiment the method 600 returns to an initial stimulation procedure.

One or more techniques or procedures for applying, varying, and/or adjusting neural stimulation to affect power consumption and/or neural stimulation efficacy in accordance with the present invention may be initiated or performed in view of a patient's drug or chemical substance therapy. In some situations, there may be a delay between drug administration and a drug onset time associated with noticeable or significant symptomatic benefit. Moreover, since drug levels within the body decrease following drug administration as a drug is metabolized, patient symptoms will become more noticeable or unacceptable over time.

Figure 15:
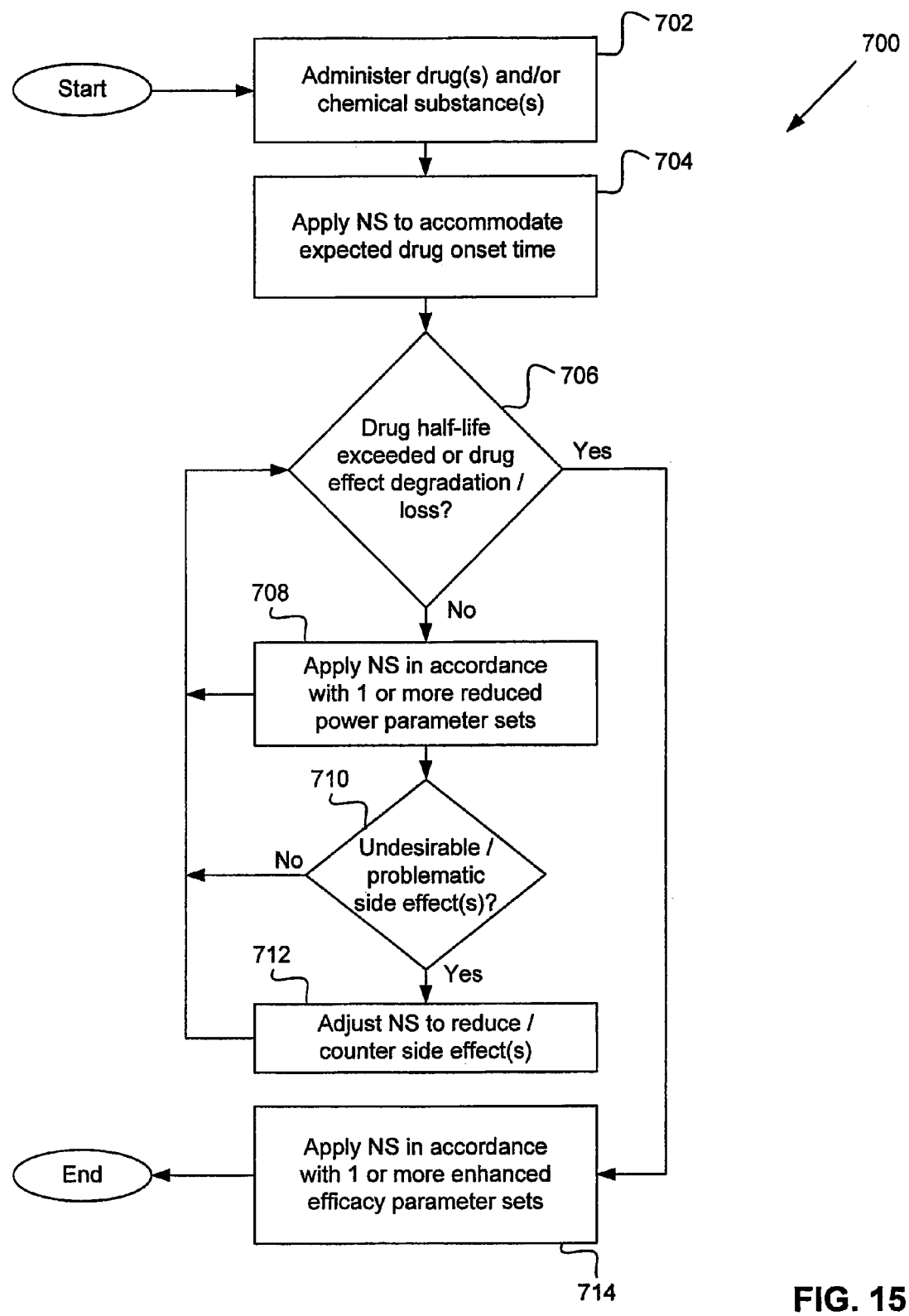
FIG. 15 is a flow chart illustrating methods for adjusting power consumption in accordance with further embodiments of the invention.

FIG. 15 is a flowchart illustrating various methods for affecting power consumption and/or neural stimulation efficacy in view of a drug and/or chemical substance therapy. In one embodiment, a method 700 comprises a drug and/or chemical substance administration procedure 702 that involves the injection, ingestion, and/or other type of application of one or more relevant substances. Such a procedure may involve, for example, self-administration of Levodopa or dopamine agonists.

The method 700 may further comprise an initial stimulation procedure 704 that involves applying neural stimulation to the patient in a manner that accommodates an expected drug onset time and/or an actual or expected initial or peak level of drug benefit. The initial stimulation procedure 704 may be time referenced or approximately synchronized to an actual or approximate drug administration time. Depending upon embodiment details, the initial stimulation procedure 704 may be directed toward providing reduced or significantly reduced power consumption if the drug(s) under consideration provide significant symptomatic benefit in the absence of neural stimulation.

The method 700 may also comprise a first evaluation procedure 706 that involves determining whether a) an actual or expected drug half-life time has been reached or exceeded; and/or b) one or more patient symptoms has reappeared to an extent that is undesirable problematic. One or more portions of the first evaluation procedure 706 may be performed automatically, for example, based upon a clock or timer; and/or in response to receipt and/or analysis of a set of signals received from a patient monitoring device 200 that is operatively coupled to an IPG or stimulation signal generator. A representative patient monitoring device 200 may comprise, for example, a motion sensor or one or more accelerometers.

In the event that a drug half-life has not been reached or exceeded, and/or a drug effect maintained at a desirable or acceptable level, the method 700 may comprise a first adjustment procedure 708 that involves applying neural stimulation in accordance with one or more reduced-power stimulation parameter sets. Thus, while patient symptoms are adequately controlled or managed by the patient's drugs, an undesirable or unnecessary amount of power consumption may be avoided.

The method 700 may additionally comprise a second evaluation procedure 710 that involves determining whether one or more undesirable or problematic drug-related side effects is present. One or more portions of the second evaluation procedure 710 may be performed manually or automatically, in manners analogous to those indicated above. In the event that an undesirable or problematic side effect is present, the method 700 may comprise a second adjustment procedure 712 directed toward varying, adjusting, or modifying the neural stimulation in a manner that at least partially counters the side effect.

In the event that a drug half-life has been reached or exceeded and/or a drug effect has degraded to an undesirable extent, the method 700 may comprise a third adjustment procedure 714 that involves applying neural stimulation in accordance with one or more stimulation parameter sets directed primarily toward providing enhanced or maximal efficacy, possibly with power consumption as a secondary consideration.

In various embodiments, one or more adjustment procedures 708, 712, 714 may be initiated and/or terminated in response to a signal received from a patient-controlled input device (e.g., a patient magnet or a reduced-functionality external programming device). An adjustment procedure 708, 712, 714 may involve switching to, stepping through, or otherwise testing particular stimulation parameter sets in a manual, semi-automatic, or automatic manner. Some of such parameter sets may be prestored in or on a programmable computer medium, for example, one or more parameter sets that were previously effective for treating patient symptoms. In several embodiments, previously effective parameter sets may be further modified on a manual, semi-automatic, or automatic basis, possibly in association with patient and/or patient monitoring unit input, to enhance a likelihood of achieving or preserving symptomatic benefit.

From the foregoing, it will be appreciated that specific embodiments of the invention have been described herein for purposes of illustration, but that various modifications may be made without deviating from the invention. For example, several aspects of the invention have been described in the context of cortical electromagnetic stimulation devices, and in other embodiments, stimulation may be provided by subcortical devices. Aspects of the invention described in the context of particular embodiments may be combined or eliminated in other embodiments. For example, methods described in the context of particular neurostimulation devices may be applied to other neurostimulation devices in other embodiments. Further, while advantages associated with certain embodiments of the invention have been described in the context of those embodiments, other embodiments may also exhibit such advantages, and not all embodiments need necessarily exhibit such advantages to fall within the scope of the invention. Accordingly, the invention is not limited except as by the appended claims.

We claim:

1. A method of treating Parkinson's disease (PD) in a patient, the method comprising:
   receiving one or more signals from a patient-controller input device that is indicative of self-administration of Levodopa or other dopamine agonist;
   in response to the receiving, communicating one or more signals by the patient-controller input device to an implantable pulse generator to initiate a pre-defined stimulation protocol to accommodate for metabolization of the administered Levodopa or dopamine agonist, wherein the pre-defined stimulation protocol comprises:
   (a) applying a first stimulation program after a first time delay, the first stimulation program including stimulation parameters selected to provide an optimal stimulation therapy after a drug-onset time of the administered Levodopa or dopamine agonist;
   (b) applying a second stimulation program after a second time delay, the second stimulation program including stimulation parameters selected to provide an optimal stimulation therapy for a drug half-life of the administered Levodopa or dopamine agonist; and
   (c) applying a third stimulation program after a third time delay, the third stimulation program including stimulation parameters selected to provide an optimal stimulation therapy for drug level substantially below a level expected for the drug half-life of the administered Levodopa or dopamine agonist;
   wherein the applying the first, second, and third stimulation programs occurs automatically by the implantable pulse generator implanted in the patient in response to the implantable pulse generator receiving the one or more signals from the patient-controller input device.

2. The method of claim 1 wherein the first stimulation program causes the implantable pulse generator to applying lower-power stimulation to the patient.

3. The method of claim 1 wherein the drug-onset time corresponds to an expected peak level of therapeutic benefit of the administered Levodopa or dopamine agonist.

4. The method of claim 1 wherein the first, second, and third stimulation programs employ different burst rates for stimulation pulses applied during the first, second, and third stimulation programs.

5. The method of claim 1 wherein the stimulation pulses of the first, second, and third stimulation programs include timing-variations between successive bursts of pulses during the application of pulses of the first, second, and third stimulation programs.

* * * * *